(12) United States Patent
Carniato et al.

(10) Patent No.: US 9,877,962 B2
(45) Date of Patent: Jan. 30, 2018

(54) PIPERAZINYL DERIVATIVES FOR THE TREATMENT OF CANCER

(71) Applicant: Marc-Henry Pitty, Boulogne-Billancourt (FR)

(72) Inventors: Denis Carniato, Marcoussis (FR); Jean-Francois Briand, Saclay (FR); Mathieu Gutmann, Vaugrigneuse (FR); Olivier Busnel, Allennes les Marais (FR); Cécile Bougeret, Nevers (FR); Benoit Deprez, Lille (FR); Karine Jaillardon, Saint Michel s/Orge (FR)

(73) Assignee: Marc Henry Pitty, Boulogne-Billancourt (FR)

( * ) Notice: Subject to any disclaimer, the term of this patent is extended or adjusted under 35 U.S.C. 154(b) by 0 days.

(21) Appl. No.: 15/135,994

(22) Filed: Apr. 22, 2016

(65) Prior Publication Data
US 2016/0237042 A1 Aug. 18, 2016

Related U.S. Application Data

(63) Continuation-in-part of application No. 14/369,407, filed as application No. PCT/EP2012/077059 on Dec. 28, 2012, now Pat. No. 9,321,778.

(30) Foreign Application Priority Data

Dec. 30, 2011 (FR) .................................... 11 62586

(51) Int. Cl.
*A61K 31/495* (2006.01)
*A61K 31/496* (2006.01)
*C07D 241/04* (2006.01)
*A61K 45/06* (2006.01)
*C07D 409/06* (2006.01)
*C07D 487/04* (2006.01)
*C07D 487/08* (2006.01)
*A61K 31/4985* (2006.01)

(52) U.S. Cl.
CPC .......... *A61K 31/496* (2013.01); *A61K 31/495* (2013.01); *A61K 31/4985* (2013.01); *A61K 45/06* (2013.01); *C07D 241/04* (2013.01); *C07D 409/06* (2013.01); *C07D 487/04* (2013.01); *C07D 487/08* (2013.01)

(58) Field of Classification Search
CPC ................ A61K 31/496; A61K 31/495; A61K 31/4985; C07D 241/04
USPC ..................................... 544/121; 514/252.12
See application file for complete search history.

(56) References Cited

FOREIGN PATENT DOCUMENTS

WO     2009150248 A1    12/2009
WO  WO 2009150248 A1 *  12/2009 ........... C07C 237/22
(Continued)

OTHER PUBLICATIONS

Saab et al, Anticancer Research (2013), vol. 33, pp. 3027-3032.*
(Continued)

*Primary Examiner* — Kathrien Cruz
*Assistant Examiner* — Janet L Coppins
(74) *Attorney, Agent, or Firm* — Banner & Witcoff, Ltd.

(57) ABSTRACT

Piperazinyl derivatives of formula (I) and their use as a drug, particularly for the treatment of cancer, are disclosed. Also disclosed are pharmaceutical compositions comprising the piperazinyl derivatives, and methods for synthesizing the piperazinyl derivatives.

20 Claims, 5 Drawing Sheets

(56) References Cited

FOREIGN PATENT DOCUMENTS

| WO | 2012009678 | A1 | 1/2012 |
| WO | 2012129452 | A2 | 9/2012 |

OTHER PUBLICATIONS

Laura Gatti et al., "Overview of Tumor Cell Chemoresistance Mechanisms", Methods in Molecular Medicine, vol. 111: Chemosensitivity: vol. 2: In Vivo Models, Imaging and Molecular Regulators, pp. 127-148, 2005.

Matthew D. Hall et al., Synthesis, activity and pharmacophore development for isatin-b-thiosemicarbazones with selective activity towards multidrug resistant cellsa, J Med. Chem., 52(10): 3191-3204, 2009.

Kohno et al., "Transcription factors and drug resistance", European Journal of Cancer 41 (2005) 2577-2586.

DB Longley et al., "Molecular mechanisms of drug resistance", Journal of Pathology, J Pathol 2005; 205; 275-292.

Bruce C. Baguley, "Multiple Drug Resistance Mechanisms in Cancer", Mol Biotechnol (2010) 46:308-316, published online Aug. 18, 2010.

Jan. 31, 2013 (PCT) International Search Report in corresponding International Application No. PCT/EP2012/077059.

* cited by examiner

PIPERAZINYL DERIVATIVES FOR THE TREATMENT OF CANCER

CROSS-REFERENCE TO RELATED APPLICATIONS

This application is a continuation-in-part of U.S. application Ser. No. 14/369,407, filed Jun. 27, 2014, now allowed, which is a U.S. national stage application under 35 U.S.C. §371 of International Application PCT/EP2012/077059 (published as WO 2013/098393), filed Dec. 28, 2012, which claims priority to Application FR 1162586, filed Dec. 30, 2011. Benefit of the filing date of each of these prior applications is hereby claimed. Each of these prior applications is hereby incorporated by reference in its entirety.

FIELD OF THE INVENTION

The present invention concerns piperazinyl compounds particularly useful in the treatment of cancer, compositions containing the same and their method of preparation.

BACKGROUND OF THE INVENTION

With lengthening lifetimes cancer, one of the leading causes of mortality in the world, affects an increasingly greater number of persons and remains difficult to treat.

The developing resistance to anticancer agents is a serious problem which considerably curbs the treatment of numerous types of cancer. Lowered tolerance to an agent is often accompanied by cross-resistance to a variety of other agents. This multiple resistance to anticancer agents known as Multidrug Resistance, MDR, is caused by numerous mechanisms of which only a very small number have been well characterized. These mechanisms include an increase in drug efflux, an increase in cell detoxifying capability, alteration of molecular targets affected by these anticancer agents, modification of the DNA repair system and modification of apoptotic routes (Baguley, Mol. Biotechnol., 2010, 46, 308-316; Gatti et al., Methods Mol. Med. 2005, 111, 127-148; Longley et al., J. Pathol. 2005, 205, 275-292; Kohno et al., Eur. J. Cancer 2005, 41, 2577-2586).

The development of anticancer treatments able to avoid these resistance mechanisms is a major challenge and up until the present time the initiated trials have given few results.

Anticancer agents more particularly intended for the treatment of chemotherapy-resistant cancer are described in WO 2009/150248. They meet the following general formula:

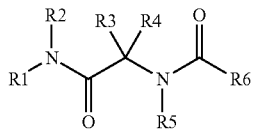

where R1 and R2, together with the nitrogen atom which carries them, may form a heterocycle such as a piperazinyl group optionally substituted, the only exemplified compounds being optionally substituted on the nitrogen atom of the piperazine.

SUMMARY OF THE INVENTION

The inventors of this patent application have surprisingly discovered that the insertion of a substituent X at alpha position of the second nitrogen atom of piperazine (see formula (I) below) allows an improvement in the physico-chemical properties of the compounds, in particular their solubility, their pharmacokinetic properties and biological activities.

The subject of the present patent application is therefore more particularly a substituted piperazinyl compound of following general formula (I):

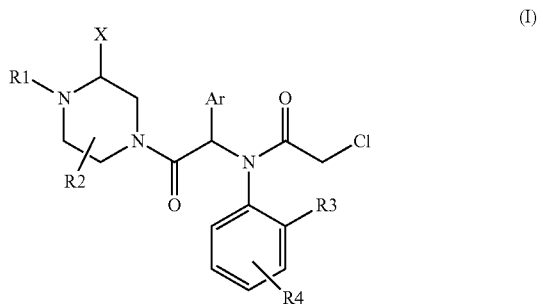

and the pharmaceutically acceptable salts thereof, its stereoisomers or mixtures of stereoisomers in any proportion, in particular an enantiomer mixture and notably a racemic mixture, where:

X is a $(C_1-C_6)$ alkyl, phenyl, benzyl, C(O)OR5 or C(O)NHR5 group;
R1 is a hydrogen atom or a C(O)H, C(O)R6 or C(O)OR6 group;
R2 is a hydrogen atom or a $(C_1-C_6)$alkyl group;
or R2 together with R1 or X forms a saturated hydrocarbon chain to form a 5 or 6-membered ring, in particular a 5-membered ring;
R3 is a hydrogen or halogen atom or a $(C_1-C_6)$alkyl or $(C_1-C_6)$alkoxy group;
R4 is a hydrogen or halogen atom, CN, $NO_2$, or a $(C_1-C_6)$alkyl, $(C_1-C_6)$alkoxy, aryloxy, benzyloxy or heteroaryloxy group, the said group optionally being substituted by one or more halogen atoms;
Ar is a thiophenyl group or a phenyl group optionally substituted by one or more halogen atoms; and
R5 and R6 independently of one another are a $(C_1-C_6)$ alkyl, aryl-$(C_1-C_6)$alkyl or aryl group, the said group optionally being substituted by one or more halogen atoms.

By <<halogen>> in the meaning of the present invention is meant a fluorine, bromine, chlorine or iodine atom. Advantageously it is a fluorine, bromine or chlorine atom.

By <<alkyl>> group in the meaning of the present invention is meant any saturated, straight-chain or branched hydrocarbon group, advantageously having 1 to 6, preferably 1 to 4 carbon atoms. These may particularly be methyl, ethyl, n-propyl, iso-propyl, n-butyl, isobutyl, sec-butyl, tert-butyl, n-pentyl, neopentyl or n-hexyl groups. Advantageously it is a methyl, ethyl, isopropyl, tert-butyl or isobutyl group.

In some cases, the alkyl group may optionally be substituted by one or more halogen atoms, in particular bromine, chlorine and fluorine and advantageously fluorine. In this case the group will particularly be the $-CF_3$ group.

By <<alkoxy>> group in the meaning of the present invention is meant an alkyl group such as defined above linked to the remainder of the molecule via an oxygen atom.

Examples of alkoxy group are the methoxy, ethoxy, isopropoxy or tert-butoxy groups. Advantageously it is the methoxy or tert-butoxy group, and further advantageously the methoxy group.

In some cases, the alkoxy group can be substituted by one or more fluorine atoms. In this case, it is advantageously the —OCHF$_2$ or —OCF$_3$ group, in particular —OCF$_3$.

By <<aryl>> group in the meaning of the present invention is meant an aromatic group preferably having 5 to 10 carbon atoms and comprising one or more fused rings. Advantageously it is the phenyl group.

By <heteroaryl>> group in the meaning of the present invention is meant any aryl group such as defined above in which one or more carbon atoms have been replaced by one or more heteroatoms, advantageously 1 to 4 and more advantageously 1 to 2, such as sulfur, nitrogen or oxygen atoms for example. Advantageously it is a furyl, thiophenyl, pyridinyl, pyrimidyl, quinolinyl, 1,2,3-thiadiazolyl benzoimidazolyl, indazolyl or 1,2,3-benzotriazolyl group.

By <aryloxy group in the meaning of the present invention is meant an aryl group such as defined above linked to the remainder of the molecule via an oxygen atom. It is advantageously a phenyloxy group.

By <<heteroaryloxy>> group in the meaning of the present invention is meant a heteroaryl group such as defined above linked to the remainder of the molecule via an oxygen atom. It is advantageously a pyridinyloxy group.

By <<aryl-(C$_1$-C$_6$)alkyl group in the meaning of the present invention is meant an aryl group such as defined above linked to the remainder of the molecule via an alkyl group such as defined above comprising 1 to 6 carbon atoms. Advantageously it is a benzyl or 1-phenethyl group, and more advantageously benzyl.

In the present invention by <<pharmaceutically acceptable>> is meant that which is useful for the preparation of a pharmaceutical composition that is generally safe, non-toxic and neither biologically nor otherwise undesirable and is acceptable for veterinary use and human pharmacopeia use.

By <<pharmaceutically acceptable salts of a compound in the present invention is meant salts which are pharmaceutically acceptable as defined herein and which have the desired pharmacological activity of the parent compound. Such salts comprise:
(1) hydrates and solvates;
(2) acid addition salts formed with inorganic acids such as hydrochloric acid, hydrobromic acid, sulfuric acid, nitric acid, phosphoric acid and similar; or formed with organic acids such as acetic acid, benzenesulfonic acid, benzoic acid, camphorsulfonic acid, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphtalenesulfonic acid, propionic acid, salicylic acid, succinic acid, dibenzoyl-L-tartaric acid, tartaric acid, p-toluenesulfonic acid, trimethylacetic acid, trifluoroacetic acid and similar, advantageously it is hydrochloric acid; and
(3) the salts formed when an acid proton present in the parent compound is either replaced by a metal ion e.g. an alkaline metal ion (Na$^+$, K$^+$ or Li$^+$ for example), an alkaline-earth metal ion (such as Ca$^{2+}$ or Mg$^{2+}$) or an aluminium ion; or it is coordinated with an organic or inorganic base. Acceptable organic bases comprise diethanolamine, ethanolamine, N-methylglucamine, triethanolamine, tromethamine and similar. Acceptable inorganic bases comprise aluminium hydroxide, calcium hydroxide, potassium hydroxide, sodium carbonate and sodium hydroxide.

In the present invention by <<stereoisomers>> it is meant to designate diastereoisomers or enantiomers. They are therefore optical isomers. The stereoisomers which are not images of one another in a mirror are therefore designated as <<diastereoisomers>>, and the stereoisomers which are non-superimposable images in a mirror are designated as <<enantiomers>>.

A carbon atom linked to four non-identical substituents is called a chiral centre.

An equimolar mixture of two enantiomers is called a racemic mixture.

The compounds of the present invention can in particular meet the following formula (I-bis):

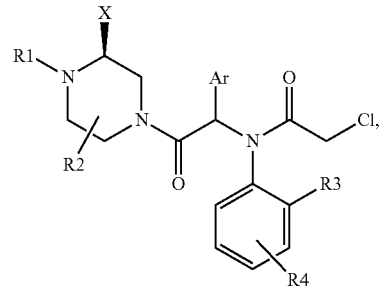

(I-bis)

the nitrogen atom carrying the X group then being of (S) configuration.

Advantageously X is a (C$_1$-C$_6$)alkyl, in particular (C$_1$-C$_4$)alkyl, phenyl or benzyl group.

Advantageously R1 is a hydrogen atom or a C(O)R6 or C(O)OR6 group, in particular a hydrogen atom.

Advantageously R2 is a hydrogen atom or a (C$_1$-C$_6$)alkyl group e.g. methyl.

Advantageously R3 is a hydrogen atom or a (C$_1$-C$_6$)alkyl group e.g. methyl.

Advantageously R4 is a hydrogen or halogen atom, or a (C$_1$-C$_6$)alkyl, (C$_1$-C$_6$)alkoxy or aryloxy group, the said group optionally being substituted by one or more halogen atoms, fluorine in particular.

Advantageously Ar is a thiophenyl group or a phenyl group substituted by one or more fluorine atoms such as 4-fluoro-phenyl.

According to one particular embodiment of the invention, X is a (C$_1$-C$_6$)alkyl, phenyl, benzyl, C(O)OR5, C(O)NHR5 group; R1 is a hydrogen atom; R2 is a hydrogen atom or a (C$_1$-C$_6$)alkyl group, advantageously (C$_1$-C$_4$)alkyl or together with R1 or X forms a saturated hydrocarbon chain to form a 5-membered ring; R3 is a hydrogen or halogen atom or a (C$_1$-C$_6$)alkyl group, in particular (C$_1$-C$_3$)alkyl, or a (C$_1$-C$_6$)alkoxy e.g. methoxy; R4 is a halogen atom, CN, NO$_2$ or a (C$_1$-C$_6$)alkyl, (C$_1$-C$_6$)alkoxy, aryloxy, benzyloxy or heteroaryloxy group, the said group optionally being substituted by one or more halogen atoms; Ar is a thiophenyl group or a phenyl group optionally substituted by a halogen; and R5 and R6 independently of one another are a (C$_1$-C$_6$) alkyl, aryl-(C$_1$-C$_6$)alkyl or aryl group, the said group optionally being substituted by one or more halogen atoms.

More advantageously, X is a (C$_1$-C$_6$)alkyl, phenyl, benzyl, C(O)OR5, C(O)NHR5 group; R1 is a hydrogen atom; R2 is a hydrogen atom or a C$_1$-C$_6$)alkyl group, advantageously (C$_1$-C$_4$)alkyl; R3 is a hydrogen or halogen atom or a (C$_1$-C$_6$)alkyl group, in particular (C$_1$-C$_3$)alkyl, or a (C$_1$-

$C_6$)alkoxy, e.g. methoxy; R4 is a halogen atom or a ($C_1$-$C_6$) alkyl, ($C_1$-$C_6$)alkoxy, aryloxy, benzyloxy or heteroaryloxy group, the said group optionally being substituted by one or more halogen atoms; Ar is a thiophenyl group or phenyl group optionally substituted by a halogen; and R5 and R6 independently of one another are a ($C_1$-$C_6$)alkyl, aryl-($C_1$-$C_6$)alkyl or aryl group, the said group optionally being substituted by one or more halogen atoms.

Further advantageously, X is a ($C_1$-$C_6$)alkyl, phenyl or benzyl group; R1 and R2 are a hydrogen atom; R3 is a hydrogen or halogen atom or a ($C_1$-$C_6$)alkyl group, in particular ($C_1$-$C_3$)alkyl; R4 is a halogen atom or a ($C_1$-$C_6$) alkyl, ($C_1$-$C_6$)alkoxy, aryloxy or benzyloxy group, the said group optionally being substituted by one or more halogen atoms; Ar is a thiophenyl group or a phenyl group optionally substituted by a halogen; and R5 and R6 independently of one another are a ($C_1$-$C_6$)alkyl, aryl-($C_1$-$C_6$)alkyl or aryl group, the said group optionally being substituted by one or halogen atoms.

Preferably X is a ($C_1$-$C_6$)alkyl, phenyl or benzyl group; R1 and R2 are a hydrogen atom; R3 is a hydrogen atom or a ($C_1$-$C_6$)alkyl group, in particular ($C_1$-$C_3$)alkyl; R4 is a halogen atom or a ($C_1$-$C_6$)alkyl, ($C_1$-$C_6$)alkoxy, aryloxy or benzyloxy group, the said group optionally being substituted by one or more halogen atoms; Ar represents a thiophenyl group or a phenyl group optionally substituted by a fluorine atom such as 4-fluoro-phenyl; and R5 and R6 independently of one another are a ($C_1$-$C_6$)alkyl, aryl-($C_1$-$C_6$)alkyl or aryl group, the said group optionally being substituted by one or more fluorine atoms.

In particular it is one of the compounds in Examples I-1a to I-63 described in the experimental part below, or one of the pharmaceutically acceptable salts thereof, their stereoisomers or mixtures of stereoisomers in any proportion, in particular an enantiomer mixture and especially a racemic mixture.

The present invention also concerns a compound of formula (I) such as defined above for use thereof as drug intended in particular for the treatment or prevention of cancer, and particularly to treat chemotherapy-resistant cancer.

The present invention also concerns the use of a compound of formula (I) such as defined above to produce a drug particularly intended to treat or prevent cancer, in particular to treat chemotherapy-resistant cancer.

The present invention also concerns a method for treating or preventing cancer, in particular chemotherapy-resistant cancer, comprising the administration of a sufficient amount of formula (I) compound such as defined above to a patient in need thereof.

The cancer may be more particularly selected from breast cancer, leukaemia (such as acute promyelocytic leukaemia), colon cancer (such as colon adenocarcinoma), pancreatic cancer, ovarian cancer, melanoma, lung cancer, central nervous system (CNS) cancer, prostate cancer, renal cancer, head and neck cancer and hepatocarcinoma, and more particularly a chemotherapy-resistant cancer.

A further subject of the invention is a pharmaceutical composition comprising at least one formula (I) compound such as defined above in association with one or more pharmaceutically acceptable excipients.

In one particular embodiment, this composition may comprise at least one other active ingredient.

In particular this or these active ingredient(s) may be anticancer agents conventionally used to treat cancer. These anticancer agents can be selected in particular from among cisplatin and the derivatives thereof such as carboplatin and oxalyplatin; taxanes such as taxol, taxotere, paclitaxel and docetaxel; vinca alkaloids such as vinblastine, vincristine and vinorelbine; purine analogues such as mercaptopurine, thioguanine, pentostatin and 2-chlorodeoxyadenosine; topoisomerase I inhibitors such as camptothecin compounds e.g. irinotecan and topotecan; topoisomerase II inhibitors such as epipodophyllotoxin, podophyllotoxin and the derivatives thereof e.g. etoposide and teniposide; anti-tumour nucleoside derivatives such as 5-fluorouracil, leucovorin, gemcitabine or capecitabine; alkylating agents such as nitrogen mustards e.g. cyclophosphamide, mechlorethamine, chlorambucil and melphalan, nitroso-ureas such as carmustin, lomustin and streptozocin, alkylsulfonates such as busulfan, ethylenimines and methylmelamines such as thiotepa and hexamethylmelamine, and tetrazines such as dacarbazine; derivatives of anti-tumour anthracyclines such as daunorubicin, adriamycin, doxil, idarubicin and mitoxantrone; molecules targeting the IGF-I receptor such as picropodophyllin; derivatives of tetracarcin such as tetrocarcin A; corticosteroids such as prednisone; antibodies such as trastuzumab (anti-HER2 antibody), rituximab (anti-CD20 antibody), gemtuzamab, cetuximab, pertuzumab and bevacizumab; antagonists or selective modulators of oestrogen receptors such as tamoxifen, fulvestrant, toremifene, droloxifene, faslodex and raloxifene; aromatase inhibitors such as exemestane, anastrozole, letrozole and vorozole; differentiating agents such as retinoids e.g. retinoic acid and vitamin D and agents blocking the metabolism of retinoic acid such as accutane; DNA methyl-transferase inhibitors such as azacytidine and decitabine; antifolates such as permetrexed disodium; antibiotics such as antinomycin D, bleomycin, mitomycin C, actinomycin D, carminomycin, daunomycin and plicamycin; antimetabolites such as chlofarabine, aminopterin, cytosine arabinoside, floxuridine and methotrexate; apoptosis-inducing agents and anti-angiogenic Bcl-2 inhibitors such as YC 137, BH 312, ABT 737, gossypol, HA 14-1, TW 37 and decanoic acid; agents binding to tubulin such as combrestatin, derivatives of colchicine and nocodazole; kinase inhibitors such as flavoperidol, imatinib mesylate, erlotinib and gefitinib; farnesyl transferase inhibitors such as tipifarnib; inhibitors of histone-deacetylases such as sodium butyrate, suberoylanilide hydroxamic acid, depsipeptide, NVP-LAQ824, R306465, JNJ-26481585 and trichostatin A; inhibitors of the ubiquitin-proteasome system such as MLN.41, bortezomib and yondelis; and telomerase inhibitors such as telomestatin.

The compounds of the invention can be given via oral, sublingual, parenteral, sub-cutaneous, intramuscular, intravenous, transdermal, local or rectal route.

In the pharmaceutical compositions of the present invention for oral, sublingual, parenteral, sub-cutaneous, intramuscular, intravenous, transdermal, local or rectal route, the active ingredient can be administered in unit administration forms, in a mixture with conventional pharmaceutical carriers, to animals or to human beings. Suitable unit administration forms include forms via oral route such as tablets, capsules, powders, granules and oral solutions or suspensions, sublingual and buccal administration forms, parenteral, sub-cutaneous, intramuscular, intravenous, intranasal or intraocular administration forms, and rectal administration forms.

When a solid composition is prepared in tablet form, the main active ingredient is mixed with a pharmaceutical carrier such as gelatin, starch, lactose, magnesium stearate, talc, gum arabic or analogues. It is possible to coat the tablets with sucrose or other suitable materials, or they can be treated so that they have sustained or delayed release and continuously release a predetermined amount of active ingredient.

A capsule preparation is obtained by mixing the active ingredient with a diluent and pouring the mixture obtained into soft or hard capsules.

A preparation in syrup or elixir form can contain the active ingredient together with a sweetener, an antiseptic and taste enhancer and suitable colouring agent.

Water-dispersible powders or granules can contain the active ingredient in a mixture with dispersing agents or wetting agents, or suspending agents, and also with taste enhancers or sweeteners.

For rectal administration, recourse is made to suppositories prepared with binders which melt at rectal temperature e.g. cocoa butter or polyethylene glycols.

For parenteral, intranasal or intraocular administration use is made of aqueous suspensions, of saline isotonic solutions or sterile, injectable solutions which contain pharmacologically compatible dispersing agents and/or wetting agents.

The active ingredient can also be formulated in microcapsule form optionally with one or more additive carriers.

The compounds of the invention can be used at doses of between 0.01 mg and 1000 mg per day, given in a single daily dose or in several doses throughout the day e.g. twice daily in equal doses. The daily administered dose is advantageously between 5 mg and 500 mg, more advantageously between 10 mg and 200 mg. It may be necessary to use doses outside these ranges which persons skilled in the art will know how to determine.

A further subject of the invention is a pharmaceutical composition comprising:

(i) at least one formula (I) compound such as defined above; and (ii) at least one other active ingredient as combination products for simultaneous, separate or time-staggered use.

It is effectively frequent for cancer to be treated with bi- or tri-therapy. It may be useful in particular to associate the molecules of the invention with one or more anticancer compounds first allowing treatment of the cancer and secondly preventing the onset of resistant cancer cells.

In particular, this or these active ingredient(s) may be anticancer agents usually used to treat cancer. These anticancer agents can be selected in particular from among cisplatin and its derivatives such as carboplatin and oxalyplatin; taxanes such as taxol, taxotere, paclitaxel and docetaxel; vinca alkaloids such as vinblastine, vincristine and vinorelbine; purine analogues such as mercaptopurine, thioguanine, pentostatin and 2-chlorodeoxyadenosine; topoisomerase I inhibitors such as camptothecin compounds e.g. irinotecan and topotecan; topoisomerase II inhibitors such as epipodophyllotoxin, podophyllotoxin and the derivatives thereof such as etoposide and teniposide; anti-tumour nucleoside derivatives such as 5-fluorouracil, leucovorin, gemcitabine or capecitabine; alkylating agents such as nitrogen mustards e.g. cyclophosphamide, mechlorethamine, chlorambucil and melphalan, nitroso-ureas such as carmustin, lomustin and streptozocin, alkylsulfonates such as busulfan, ethylenimines and methylmelamines such as thiotepa and hexamethylmelamine, and tetrazines such as dacarbazine; anti-tumour anthracycline derivatives such as daunorubicin, adriamycin, doxil, idarubicin and mitoxantrone; molecules targeting the IGF-I receptor such as picropodophyllin; tetracarcin derivatives such as tetrocarcin A; corticosteroids such as prednisone; antibodies such as trastuzumab (anti-HER2 antibody), rituximab (anti-CD20 antibody), gemtuzamab, cetuximab, pertuzumab and bevacizumab; antagonists or selective modulators of oestrogen receptors such as tamoxifen, fulvestrant, toremifene, droloxifene, faslodex and raloxifene; aromatase inhibitors such as exemestane, anastrozole, letrozole and vorozole; differentiating agents such as retinoids e.g. retinoic acid and vitamin D and agents blocking the metabolism of retinoic acid such as accutane; DNA methyl-transferase inhibitors such as azacytidine and decitabine; antifolates such as permetrexed disodium; antibiotics such as antinomycin D, bleomycin, mitomycin C, actinomycin D, carminomycin, daunomycin and plicamycin; antimetabolites such as chlofarabine, aminopterin, cytosine arabinoside, floxuridine and methotrexate; apoptosis-inducing agents and anti-angiogenic agents of Bcl-2 inhibitors such as YC 137, BH 312, ABT 737, gossypol, HA 14-1, TW 37 and decanoic acid; agents binding to tubulin such as combrestatin, derivatives of colchicine an nocodazole; kinase inhibitors such as flavoperidol, imatinib mesylate, erlotinib an gefitinib; farnesyl transferase inhibitors such as tipifarnib; inhibitors of histone-deacetylases such as sodium butyrate, suberoylanilide hydroxamic acid, depsipeptide, NVP-LAQ824, R306465, JNJ-26481585 and trichostatin A; inhibitors of the ubiquitin-proteasome system such as MLN.41, bortezomib and yondelis; and telomerase inhibitors such as telomestatin.

A further subject of the invention is a pharmaceutical composition such as defined above, for use thereof as drug to treat or prevent cancer in particular, and particularly chemotherapy-resistant cancer.

The cancer may be more particularly selected from breast cancer, leukaemia (such as acute promyelocytic leukaemia), colon cancer (such as colon adenocarcinoma), pancreatic cancer, ovarian cancer, melanoma, lung cancer, central nervous system (CNS) cancer, prostate cancer, renal cancer, head and neck cancer and hepatocarcinoma, and more particularly a chemotherapy-resistant cancer.

The present invention also concerns a method for preparing a formula (I) compound such as defined above comprising the following successive steps:

a) reacting an amine of following formula (II):

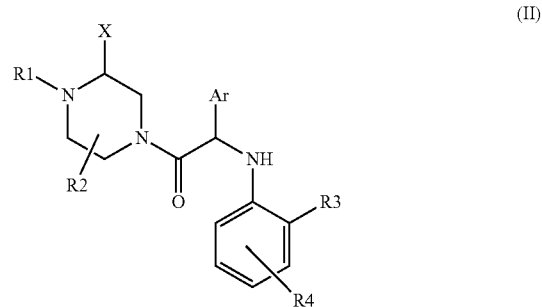

where X, R1, R2, R3, R4 and Ar are such as previously defined, R1 not representing a hydrogen atom;

with chloroacetyl chloride in the presence of a base to give a formula (I) compound where R1≠H; and b) optionally deprotecting the nitrogen atom carrying the R1≠H group to give a formula (I) compound where R1=H.

Step a):

The base used for this step is preferably a weak base such as NaHCO$_3$.

The amine of formula (II) can be obtained by reaction of a piperazine of following formula (III):

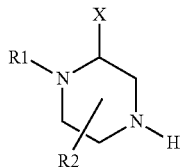

(III)

where X, R1 and R2 are as previously defined, R1 not representing a hydrogen atom, with an acid of following formula (IV):

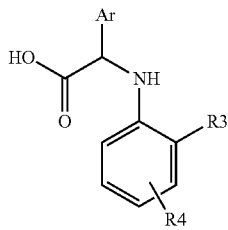

(IV)

where R3, R4 and Ar are as previously defined.

This reaction can be conducted under peptide coupling conditions well known to skilled persons.

Coupling is therefore preferably performed in the presence of a coupling agent such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), 2-(1H-benzotriazole-1-yl)-1,1,3,3-tetramethyluronium hexafluorophosphate (HBTU), 2-(1H-benzotriazole-1-yl)-1,1,3,3-tetramethyluronium tetrafluoroborate (TBTU) or O-(7-azobenzotriazol-1-yl)-1,1,3,3-tetramethyluronium hexafluorophosphate (HATU), optionally associated with a coupling auxiliary such as N-hydroxy succinimide (NHS), N-hydroxy benzotriazole (HOBt), 3,4-dihydro-3-hydroxy-4-oxo-1,2,3-benzotriazole (HOOBt), 1-hydroxy-7-azabenzotriazole (HAt) or N-hydroxysulfosuccinimide (sulfo NHS). Preferably it is HBTU.

A base such as diisopropyl-ethylamine (DIPEA) may also be present.

The piperazine of formula (III) is either obtained commercially or prepared following methods well known to persons skilled in the art.

The acid of formula (IV) can be prepared using the following successive steps:

i) reacting a ketoester of following formula (V):

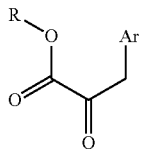

(V)

where Ar is as previously defined and R represents a (C$_1$-C$_6$)alkyl group e.g. ethyl, with an aniline of following formula (VI):

(VI)

where R3 and R4 are as previously defined, to give an imine of following formula (VII):

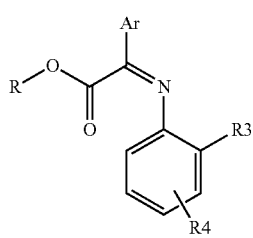

(VII)

where R, R3, R4 and Ar are as previously defined;

ii) reducing the imine of formula (VII) obtained at the preceding step to give an amine of following formula (VIII):

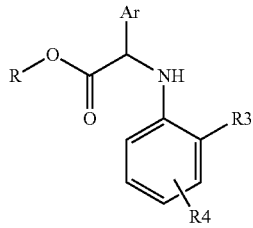

(VII)

where R, R3, R4 and Ar are as previously defined; and iii) saponifying the ester function of the formula (VIII) compound obtained at the preceding step to give the acid of formula (IV).

Step i) can be conducted in the presence of an acid such as paratoluene sulfonic acid (PTSA). The reaction can be performed in a polar solvent such as toluene. Preferably the reaction medium is heated under reflux using Dean-Stark apparatus to remove the water as and when it is formed during the reaction.

The ketoester (V) used for this reaction is either obtained commercially or prepared via Friedel-Crafts reaction using ethyl oxalyl chloride and the corresponding aromatic in the presence of a Lewis acid such as aluminium chloride AlCl$_3$.

The aniline (VI) used for this reaction is either obtained commercially or prepared using methods well known to skilled persons.

Reducing step ii) can be performed in the presence of a reducing agent well known to skilled persons such as sodium cyanoborohydride.

Saponification step iii) can be performed under conditions well known to skilled persons, in particular in the presence of a base such as NaOH, KOH or LiOH.

Step b):

This step is preferably conducted with a formula (I) compound in which R1=CO₂R6, such as CO₂tBu, via treatment with an acid such as HCl.

The compound thus obtained can be separated from the reaction medium using methods well known to skilled persons, e.g. by extraction, evaporation of the solvent or by precipitation and filtration.

The compound may also be purified if necessary using techniques well known to skilled persons, e.g. by recrystallization if the compound is crystalline, by distillation, by silica gel chromatography or high performance liquid chromatography (HPLC).

The method of the present invention to prepare compounds of the present invention where R1≠H is shown in the following reaction scheme:

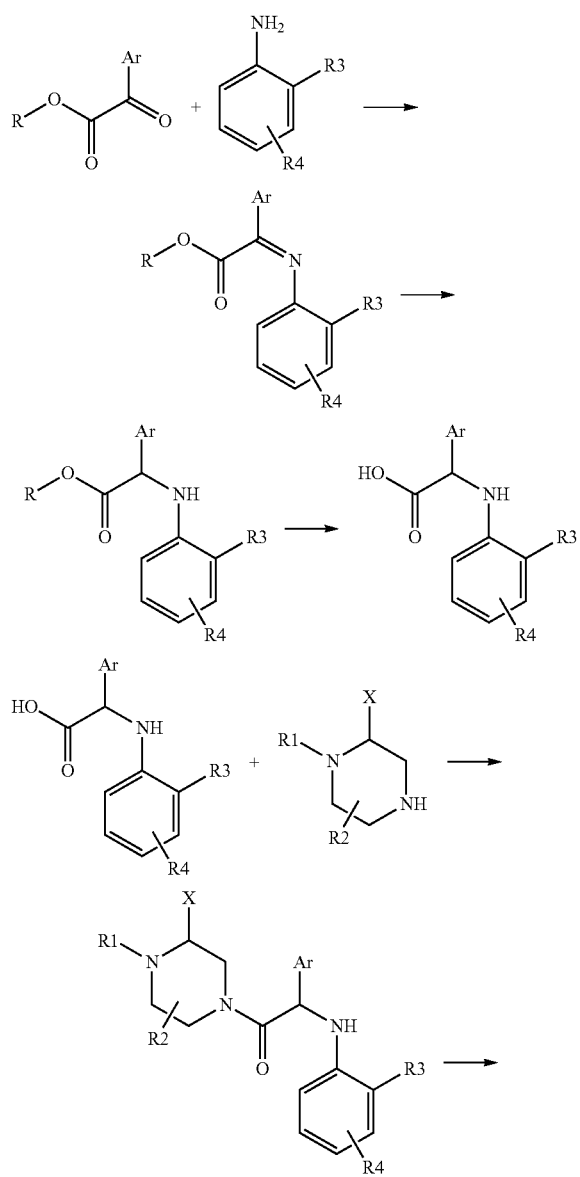

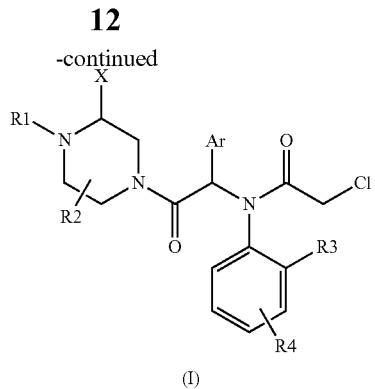

The following examples illustrate the invention but are not limiting thereof.

DETAILED DESCRIPTION OF THE INVENTION

Figure 1:
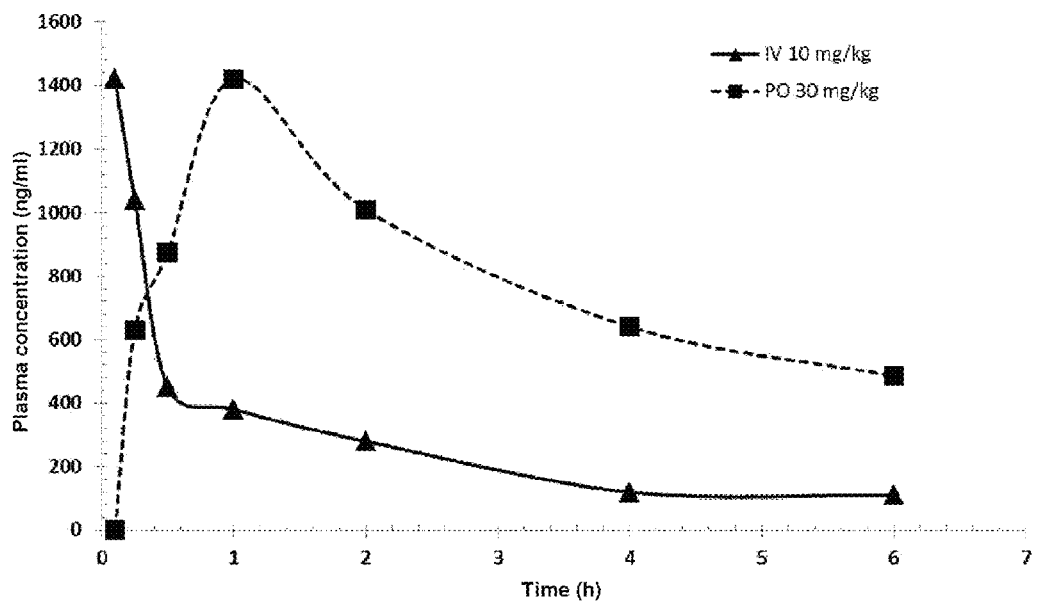
FIG. 1 gives the time-plasma concentration curves for a mouse given compound I-43 dia2 administered via intravenous route (IV) at a dose of 10 mg/kg or via oral route (PO) at a dose of 30 mg/kg.

The following examples are set forth as representative of certain aspects and advantages relating to the present disclosure. These examples are not to be construed as limiting the scope of the invention, as other equivalent embodiments will be apparent in view of the present disclosure and appended claims.

EXAMPLES

I—Synthesis of Compounds of the Invention

In the following section two different nomenclatures were adopted when the two diastereoisomers of a compound of the invention were separated:
  a/b each designating the particular structure of a single diastereoisomer;
  dia1/dia2 respectively designating the least polar and most polar diastereoisomer in the chromatographic system used.

The particular stereochemistry of each of the diastereoisomers was not determined. Therefore, it was impossible to allocate the particular structure a and b to each isolated diastereoisomer dia1 and dia2. This is why a double nomenclature is used.

The following abbreviations are used in this section:
TLC Thin Layer Chromatography
DCM Dichloromethane
DIEA Diisopropylethylamine
HBTU 2-(1H-Benzotriazole-1-yl)-1,1,3,3-tetramethyluronium hexafluorophosphate LCMS Liquid Chromatography coupled with Mass Spectrometer NMR Nuclear Magnetic Resonance RT Room temperature Examples I-1a and I-1b: Diastereoisomers of the tert-butyl ester of 4-[2-[(2-chloro-acetyl)-(4-phenoxy-phenyl)-amino]-2-(4-fluoro-phenyl)-acetyl]-(S)-2-isopropyl-piperazine-1-carboxylic acid

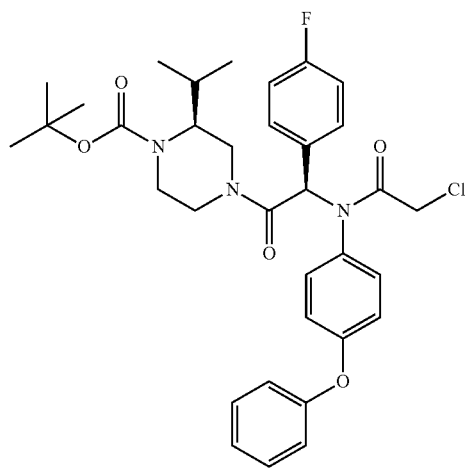

I-1a

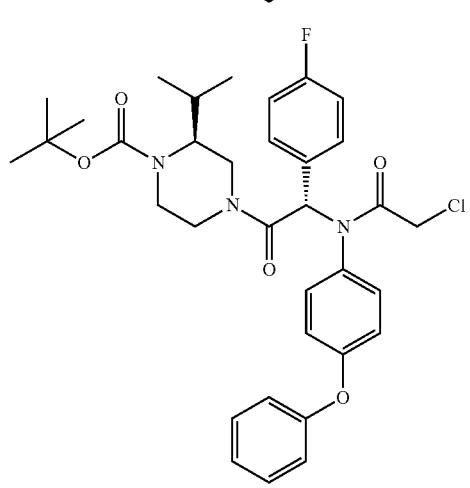

I-1b

Stage 1: Ethyl ester of (4-fluoro-phenyl)-oxo-acetic acid (1)

To a solution of aluminium chloride (21.13 g; 160 mmol) in DCM (200 mL) at 0° C. under argon, ethyl oxalyl chloride (17.9 mL; 160 mmol) was added dropwise for 10 min. The medium was left under agitation for 10 minutes. Fluorobenzene (14.7 mL; 160 mmol) diluted in 30 mL of DCM, was added dropwise at 0° C. The medium was left under agitation at room temperature for 12 hours. The medium was washed with water and the organic phase dried over $MgSO_4$. After evaporation, the recovered oil was purified by flash chromatography on silica gel eluting with cyclohexane-ethyl acetate 90:10.

A yellow oil was recovered (17.08 g; 54%).
$^1$H NMR (300 MHz, $CDCl_3$): δ 8.04-8.14 (m; 1.8H); 7.15-7.24 (m; 1.9H); 4.46 (q; J=7.2 Hz; 2.0H); 1.44 (t; J=7.2 Hz; 3.0H).

Stage 2: Ethyl ester of (4-fluoro-phenyl)-[(Z)-4-phenoxy-phenylimino]-acetic acid (2)

To a solution of 1 (3.92 g; 20 mmol) in toluene (25 mL) were successively added paratoluene sulfonic acid (200 mg; 1 mmol) and 4-phenoxyphenyl-aniline (3.70 g; 20 mmol) in the presence of a molecular sieve. The medium was placed under reflux in DeanStark apparatus for 20 hours. The medium was washed in water and the organic phase dried over $MgSO_4$. After evaporation, the recovered oil was purified by flash silica gel chromatography eluting with cyclohexane-ethyl acetate 90:10.

Recovery of a yellow oil (6.27 g; 86%).
LCMS [M+H]=364 ($C_{22}H_{18}FNO_3$)

Stage 3: Ethyl ester of (4-fluoro-phenyl)-(4-phenoxy-phenylamino)-acetic acid (3)

To a solution of 2 (6.27 g; 17.26 mmol) in methanol (75 mL) and acetic acid (7.5 mL), sodium cyanoborohydride (1.63 g; 26 mmol) was added. The medium was left under agitation for 1 hour at RT. The methanol was partly evaporated, the solution neutralized with $Na_2CO_3$ with the addition of water if necessary. The medium was extracted with DCM and the organic phase dried over $MgSO_4$. After evaporation, the recovered oil was purified by flash chromatography on silica gel eluting with cyclohexane-ethyl acetate 95:5.

Recovery of a yellow oil (5.91 g; 93%).
LCMS [M+H]=366 ($C_{22}H_{20}FNO_3$)
$^1$H NMR (300 MHz, $CDCl_3$): δ 7.45-7.54 (m; 1.9H); 7.23-7.31 (m; 1.9H); 6.97-7.11 (m; 2.9H); 6.81-6.94 (m; 3.9H); 6.54 (d; J=9.0 Hz; 2.0H); 5.01 (br; 1.0H); 4.90 (br; 0.9H); 4.10-4.32 (m; 2.0H); 1.23 (t; J=7.0 Hz; 3.0H).

Stage 4: (4-fluoro-phenyl)-(4-phenoxy-phenylamino)-acetic acid (4)

To a solution of 3 (8.04 g; 22 mmol) in 130 mL of acetonitrile was added 66 mL of a 1 M solution of LiOH (3 eq). The reaction medium was left under agitation for 2 to 3 hours, completion of the reaction being controlled by TLC (cyclohexane-ethyl acetate 60:40). The acetonitrile was partly evaporated, the medium acidified with a 1 M solution of HCl with the addition of 200 mL of water. The medium was filtered and the recovered solid washed three times in water and dried in vacuo in a drying oven in the presence of $P_2O_5$.

Recovery of a white powder (7.17 g; 97%).
LCMS [M+H]=338 ($C_{20}H_{16}FNO_3$)
$^1$H NMR (300 MHz, DMSO): δ 7.55 (dd; J=8.5 Hz; J=5.6 Hz; 2.1H); 7.28 (t; J=7.9 Hz; 2.1H); 7.20 (t; J=8.5 Hz; 2.1H); 6.99 (t; J=7.0 Hz; 1.1H); 6.74-6.90 (m; 4.0H; 6.62-6.70 (m; 2.0H); 5.10 (s 1.0H).

Stage 5: Tert-butyl ester of 4-[2-(4-fluoro-phenyl)-2-(4-phenoxy-phenylamino)-acetyl]-(S)-2-isopropyl-piperazine-1-carboxylic acid (5)

To a solution of 4 (7.17 g; 21.2 mmol) in DCM (150 mL) in the presence of one equivalent of DIEA (3.7 mL) was added a solution of Boc-alpha-(S)-isopropyl-piperazine hydrochloride (5.63 g; 21.26 mmol) in the presence of 1 eq of DIEA (3.7 mL) in 50 mL of DCM, followed by HBTU (8.06 g; 21.2 mmol). The medium was left under agitation for 12 hours. The medium was washed with water and the organic phase dried over MgSO$_4$. After evaporation the recovered oil was purified by flash chromatography on silica gel eluting with cyclohexane-ethyl acetate 80:20.

Recovery of a white foam (11.90 g; 100%).

LCMS [M+H]=548 (C$_{32}$H$_{38}$FN$_3$O$_4$)

Stage 6 Tert-butyl ester of 4-[2-[(2-chloro-acetyl)-(4-phenoxy-phenyl)-amino]-2-(4-fluoro-phenyl)-acetyl]-(S)-2-isopropyl-piperazine-1-carboxylic acid To a solution of 5 (11.86 g; 22.66 mmol) in 250 mL of DCM in the presence of NaHCO$_3$ (7.30 g; 87.0 mmol) the chloroacetyl chloride (3.45 mL; 43.3 mmol) was added. The medium was left under agitation for 12 hours. The medium was washed with water and the organic phase dried over MgSO$_4$. After evaporation the recovered oil was purified by flash chromatography on silica gel with cyclohexane-ethyl acetate gradient of 95-5' to 50-50 to obtain two diastereoisomers separately in the form of colourless foam:

Least Polar Diastereoisomer (I-1 Dia1)

(3.80 g; 28%)

LCMS [M+H]=625 (C$_{34}$H$_{39}$ClFN$_3$O$_5$)

$^1$H NMR (300 MHz, CDCl$_3$): δ 7.92-8.01 (m; 1.0H); 7.30-7.40 (m; 2.0H); 7.10-7.18 (m; 1.1H); 7.01-7.09 (m; 1.1H); 6.84-7.00 (m; 6.1H); 6.55-6.65 (m; 1.1H); 6.32-6.48 (m; 2.1H); 4.72 (d; J=13.5 Hz; 0.5H) 4.63 (d; J=13.5 Hz; 0.4H); 3.52-3.96 (m; 4.0H); 3.10-3.27 (m; 0.5H); 2.85-3.07 (m; 0.4H); 2.23-2.85 (m; 0.5H+0.7H+0.4H); 1.87-2.14 (m; 0.6H); 1.42 (s; 8.7H); 1.17 (d; J=6.6 Hz; 1.0H); 1.03 (d; J=6.6 Hz; 1.3H); 0.88 (d; J=6.6 Hz; 1.1H); 0.69 (d; J=6.6 Hz; 1.3H).

Most Polar Diastereoisomer (I-1 Dia2)

(3.29 g; 24%)

LCMS [M+H]=625 (C$_{34}$H$_{39}$ClFN$_3$O$_5$)

$^1$H NMR (300 MHz, CD$_2$Cl$_2$): δ 7.85-8.00 (m; 1.0H); 7.36 (t; J=7.6 Hz; 2.1H); 6.99-7.21 (m; 3.2H); 6.81-6.98 (m; 5.2H); 6.63 (br; 1.1H); 6.35-65.5 (m; 2.1H); 4.65 (d; J=13.1 Hz; 0.6H) 4.42 (d; J=13.1 Hz; 0.3H); 3.50-4.16 (m; 4.9H); 3.00-3.43 (m; 0.9H); 2.57-2.90 (m; 1.9H); 1.98-2.18 (m; 0.7H); 1.36-1.49 (m; 10.0H); 1.73 (d; J=6.5 Hz; 2.1H); 0.90 (d; J=6.5 Hz; 2.1H); 0.63 (d; J=6.5 Hz; 1.0H); 0.20 (d; J=6.5 Hz; 0.9H).

Examples I-2a and I-2b: Diastereoisomers of the tert-butyl ester of 4-[2-[(2-chloro-acetyl)-(4-phenoxy-phenyl)-amino]-2-(4-fluoro-phenyl)-acetyl]-(R)-2-isopropyl-piperazine-1-carboxylic acid I-2a

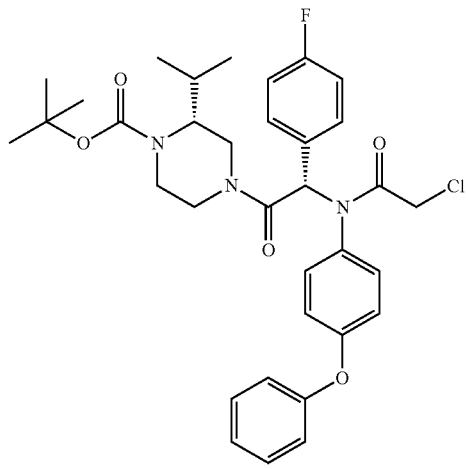

I-2b

Stage 1: Tert-butyl ester of 4-[2-(4-fluoro-phenyl)-2-(4-phenoxy-phenylamino)-acetyl]-(R)-2-isopropyl-piperazine-1-carboxylic acid (6)

To a solution of (4-fluoro-phenyl)-(4-phenoxy-phenylamino)-acetic acid 4 (253 mg; 0.75 mmol) in DCM (10 mL) in the presence of one equivalent of DIEA (131 µL) was added a solution of Boc-alpha-(R)-isopropyl-piperazine (171 mg; 0.75 mmol) in the presence of 1 eq of DIEA (131 µL) in 5 mL of DCM, followed by HBTU (285 mg; 0.75 mmol). The medium was left under agitation for 12 hours. The medium was washed with water and the organic phase dried over MgSO$_4$. After evaporation the recovered oil was purified by flash chromatography on silica gel eluting with cyclohexane-ethyl acetate 80:20.

Recovery of a white foam (369 mg; 90%).

LCMS [M+H]=548 (C$_{32}$H$_{38}$FN$_3$O$_4$)

Stage 2: Ter-butyl ester of 4-[-2-[(2-chloro-acetyl)-(4-phenoxy-phenyl)-amino]-2-(4-fluoro-phenyl)-acetyl]-(R)-2-isopropyl-piperazine-1-carboxylic acid Both diastereoisomers were prepared from 6 following the same operating mode as for the preparation in Example 1 (stage 6).

Separate recovery of the two diastereoisomers in the form of a colourless foam.

Least Polar Diastereoisomer (I-2 Dia1) (195 mg; 42%)

LCMS [M+H]=625 (C$_{34}$H$_{39}$ClFN$_3$O$_5$)

$^1$H NMR (300 MHz, CD$_2$Cl$_2$): δ 7.85-8.00 (m; 1.0H); 7.36 (t; J=7.6 Hz; 2.0H); 6.99-7.21 (m; 3.1H); 6.81-6.98 (m; 4.9H); 6.63 (br; 1.0H); 6.35-6.55 (m; 2.1H); 4.65 (d; J=13.0 Hz; 0.7H) 4.42 (d; J=13.0 Hz; 0.2H); 3.50-4.16 (m; 4.9H); 3.00-3.43 (m; 0.8H); 2.57-3.90 (m; 2.0H); 1.98-2.18 (m; 0.8H); 1.36-1.49 (m; 10.5H); 1.73 (d; J=6.5 Hz; 2.0H); 0.90 (d; J=6.5 Hz; 2.0H); 0.63 (d; J=6.5 Hz; 0.8H); 0.20 (d; J=6.5 Hz; 0.8H).

Most Polar Diastereoisomer (I-2 Dia2) (122 mg; 26%)

LCMS [M+H]=625 (C$_{34}$H$_{39}$ClFN$_3$O$_5$)

$^1$H NMR (300 MHz, CDCl$_3$): δ 7.92-8.01 (m; 1.0H); 7.30-7.40 (m; 2.0H); 7.10-7.18 (m; 1.0H); 7.01-7.09 (m; 1.1H); 6.84-7.00 (m; 6.0H); 6.55-6.65 (m; 1.1H); 6.32-6.48 (m; 2.1H); 4.72 (d; J=13.5 Hz; 0.4H) 4.63 (d; J=13.5 Hz; 0.3H); 3.52-3.96 (m; 4.7H); 3.10-3.27 (m; 0.7H); 2.85-3.07 (m; 0.5H); 2.23-2.85 (m; 0.5H+0.6H+0.8H); 1.87-2.14 (m;

0.9H); 1.42 (s; 8.6H); 1.17 (d; J=6.6 Hz; 1.4H); 1.03 (d; J=6.6 Hz; 2.1H); 0.88 (d; J=6.6 Hz; 2.1H); 0.69 (d; J=6.6 Hz; 1.6H).

Examples I-3a and I-3b: Hydrochloride of the diastereoisomers of 2-chloro-N-[1-(4-fluoro-phenyl)-2-((S)-3-isopropyl-piperazin-1-yl)-2-oxo-ethyl]-N-(4-phenoxy-phenyl)-acetamide

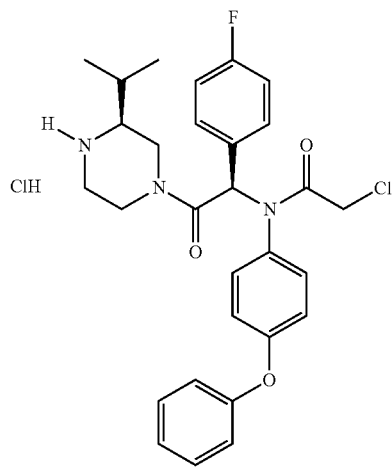

I-3a

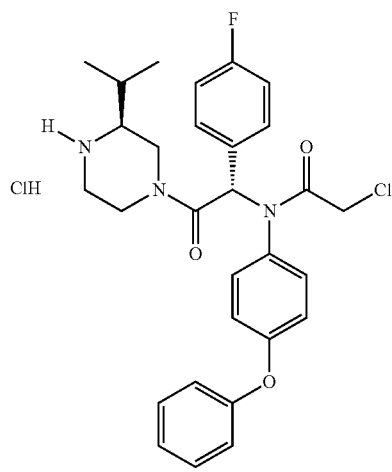

I-3b

To a solution of the I-1 dia2 diastereoisomer (3.24 g; 5.2 mmol) in 50 mL of DCM the HCl gas was added by bubbling. The reaction medium was left under agitation for 12 hours at RT. The DCM was evaporated and the residual oil precipitated in ether.

The example I-3 dia2 was obtained in the form of a white power after filtration: (2.53 g; 87%).

LCMS [M+H]=524 ($C_{29}H_{32}Cl_2FN_3O_3$)

$^1$H NMR (300 MHz, DMSO): δ 8.60-9.35 (m; 1.6H); 7.77 (br; 0.8H); 7.30-7.40 (m; 2.0H); 7.00-7.23 (m; 5.1H); 6.80-7.00 (m; 3.1H); 6.54-6.76 (m; 3.0H); 4.56 (d; J=13.3 Hz; 1.0H); 3.88-4.16 (m; 3.0H); 3.00-3.30 (m; 3.1H); 2.65-2.96 (m; 1.7H); 1.52-2.00 (m; 1.6H); 1.00 (t; J=7.4 Hz; 2.4H); 0.59 (dd; J=15.6 Hz; J=6.7 Hz; 3.5H)

Applying the same procedure starting from example I-1 dia1, example I-3 dia1 was obtained in the form of a white powder after filtration: (63 mg).

LCMS [M+H]=524 ($C_{29}H_{32}Cl_2FN_3O_3$)

$^1$H NMR (300 MHz, DMSO): δ 8.65-9.6 (br; 1.2H); 7.77 (br; 0.8H); 7.30-7.40 (m; 2.0H); 6.36-7.25 (m; 11.7H); 4.40-4.60 (m; 0.8H); 4.00-4.12 (m; 2.0H); 3.76-3.98 (m; 0.9H); 3.37-3.63 (m; 0.9H); 2.65-3.30 (m; 4.0H); 1.77-2.06 (m; 1.6H); 0.89-1.06 (m; 6.1H).

Examples I-4a and I-4b: Hydrochloride of the diastereoismers of 2-Chloro-N-[1-(4-fluoro-phenyl)-2-((R)-3-isopropyl-piperazin-1-yl)-2-oxo-ethyl]-N-(4-phenoxy-phenyl)-acetamide

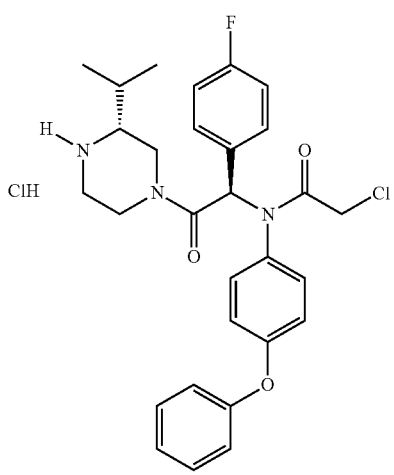

I-4a

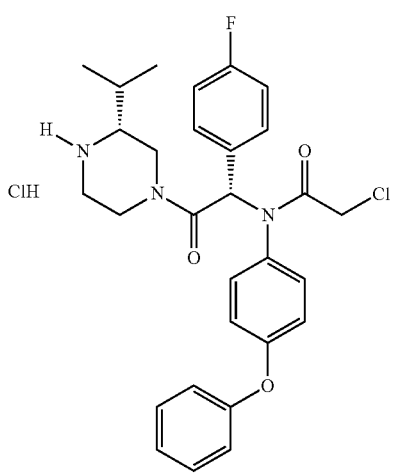

I-4b

The same protocol was followed as for Examples I-3a and I-3b starting from each of the diastereoisomers I-2a and I-2b. Starting from the First Diastereoisomer of Example I-2 (I-4 Dia1):

Recovery of a white powder after filtration: (95 mg)

LCMS [M+H]=524 ($C_{29}H_{32}Cl_2FN_3O_3$)

$^1$H NMR (300 MHz, DMSO): δ 8.65-9.6 (br; 1.3H); 7.77 (br; 0.4H); 7.30-7.40 (m; 2.0H); 6.36-7.25 (m; 11.8H); 4.40-4.60 (m; 0.9H); 4.00-4.12 (m; 2.0H); 3.76-3.98 (m; 1.0H); 3.37-3.63 (m; 1.0H); 2.65-3.30 (m; 3.8H); 1.77-2.06 (m; 1.8H); 0.89-1.06 (m; 6.1H).

Starting from the Second Diastereoisomer of Example I-2 (I-4 Dia2):

Recovery of a white powder after filtration: (95 mg)
LCMS [M+H]=524 ($C_{29}H_{32}Cl_2FN_3O_3$)
$^1$H NMR (300 MHz, DMSO): δ 8.60-9.35 (m; 1.7H); 7.77 (br; 0.9H); 7.30-7.40 (m; 2.0H); 7.00-7.23 (m; 5.0H); 6.80-7.00 (m; 3.0H); 6.54-6.76 (m; 2.9H); 4.56 (d; J=13.3 Hz; 1.0H); 3.88-4.16 (m; 3.0H); 3.00-3.30 (m; 3.1H); 2.65-2.96 (m; 1.7H); 1.52-2.06 (m; 1.9H); 1.00 (t; J=7.2 Hz; 2.4H); 0.59 (dd; J=15.4 Hz; J=6.7 Hz; 3.3H).

Examples I-5a and I-5b: Diastereoisomers of the tert-butyl ester of 4-[-2-[(2-chloro-acetyl)-(2-methyl-4-phenoxy-phenyl)-amino]-2-(4-fluoro-phenyl)-acetyl]-(S)-2-isopropyl-piperazine-1-carboxylic acid

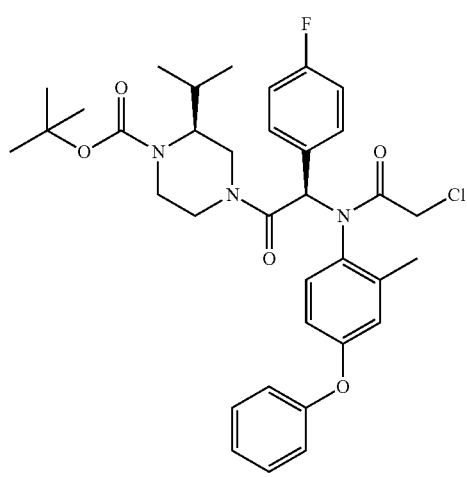

I-5a

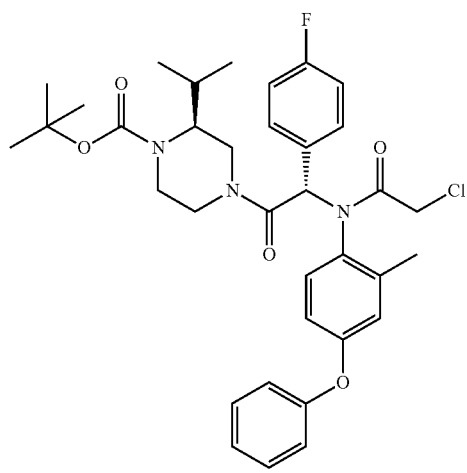

I-5b

Stage 1: Tert-butyl ester of 4-[2-(4-fluoro-phenyl)-2-(2-methyl-4-phenoxy-phenylamino)-acetyl]-(S)-2-isopropyl-piperazine-1-carboxylic acid (8)

To a solution of (4-fluoro-phenyl)-(2-methyl-4-phenoxy-phenylamino)-acetic acid (9.29 g; 26.4 mmol) in DCM (150 mL) in the presence of one equivalent of DIEA (4.6 mL) was added a solution of Boc-alpha-(S)-isopropyl-piperazine hydrochloride (7.00 g; 26.4 mmol) in the presence of 1 eq of DIEA (4.6 mL) in 50 mL of DCM, followed by HBTU (10.00 g; 26.4 mmol). The medium was left under agitation for 12 hours. The medium was washed with water and the organic phase dried over MgSO$_4$. After evaporation the recovered oil was purified by flash chromatography on silica gel eluting with cyclohexane-ethyl acetate 80:20.

Recovery of a white foam (14.13 g; 95%).
LCMS [M+H]=562 ($C_{33}H_{40}FN_3O_4$)

Stage 2: Tert-butyl ester of 4-[-2-[(2-chloro-acetyl)-(2-methyl-4-phenoxy-phenyl)-amino]-2-(4-fluoro-phenyl)-acetyl]-(S)-2-isopropyl-piperazine-1-carboxylic acid To a solution of 8 (14.13 g; 25.1 mmol) in 250 mL of DCM in the presence of NaHCO$_3$ (8.40 g; 100.0 mmol) was added chloroacetyl chloride (4.00 mL; 50.0 mmol). The medium was left under agitation for 12 hours. The medium was washed with water and the organic phase dried over MgSO$_4$. After evaporation the recovered oil was purified by flash chromatography on silica gel eluting with cyclohexane-ethyl acetate 90:10 gradually up to 50:50.

Recovery of both diastereoisomers in the form of a colourless foam:
Least Polar Diastereoisomer (I-5 Dia1) (3.83 g; 24%)
LCMS [M+H]=639 ($C_{35}H_{41}ClFN_3O_5$)
$^1$H NMR (300 MHz, CD$_2$Cl$_2$): δ 7.94-8.57 (m; 1.0H); 7.35 (t; J=7.9 Hz; 2.0H); 7.07-7.27 (m; 3.0H); 6.74-6.95 (m; 5.0H); 6.58 (br d; J=2.6 Hz; 1.1H); 6.51 (br s; 0.2H); 6.41 (s; 0.8H); 6.31 (br s; 0.3H); 4.62 (d; J=13.5 Hz; 0.7H) 4.39 (d; J=13.5 Hz; 0.3H); 3.53-4.05 (m; 4.8H); 3.04-3.46 (m; 0.8H); 2.41-2.96 (m; 2.1H); 2.04-2.23 (m; 0.8H); 1.82-1.95 (m; 2.2H); 1.43 (br s; 10.1H); 1.07 (d; J=6.5 Hz; 2.1H); 0.90 (d; J=6.5 Hz; 2.3H); 0.63 (d; J=6.5 Hz; 1.0H); 0.29 (d; J=6.5 Hz; 0.8H).
Most Polar Diastereoisomer (I-5 Dia2) (4.40 g; 27%)
LCMS [M+H]=639 ($C_{35}H_{41}ClFN_3O_5$)
$^1$H NMR (300 MHz, CDCl$_3$): δ 8.00-8.10 (m; 1.0H); 7.30-7.40 (m; 2.1H); 6.98-7.18 (m; 3.2H); 6.73-6.90 (m; 5.3H); 6.52-6.58 (m; 1.0H); 6.34-6.39 (m; 1.0H); 4.71 (d; J=13.5 Hz; 0.7H); 4.49 (d; J=13.5 Hz; 0.4H); 3.50-4.00 (m; 4.7H); 3.10-3.30 (m; 0.7H); 2.86-3.07 (m; 0.4H); 2.54-2.85 (m; 1.5H); 2.30-2.47 (m; 0.4H); 1.80-1.87 (m; 2.8H); 1.54-1.60 (m; 2.5H); 1.42 (br s; 8.8H); 1.19 (d; J=6.6 Hz; 1.1H); 1.00 (d; J=6.6 Hz; 1.5H); 0.88 (d; J=6.6 Hz; 1.2H); 0.64 (d; J=6.6 Hz; 1.5H).

Examples I-6a and I-6b: Diastereoisomers of the tert-butyl ester of 4-[-2-[(2-chloro-acetyl)-(4-phenoxy-phenyl)-amino]-2-(4-fluoro-phenyl)-acetyl]-(R)-2-isopropyl-piperazine-1-carboxylic acid

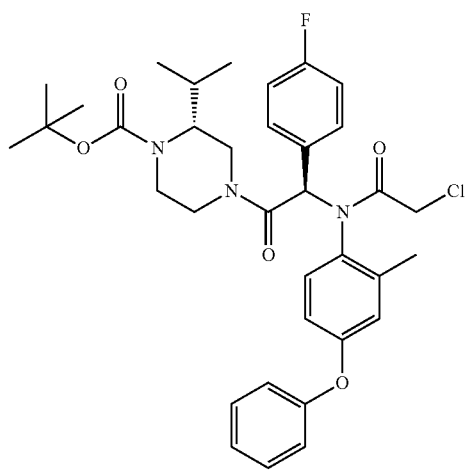

I-6a

I-6b

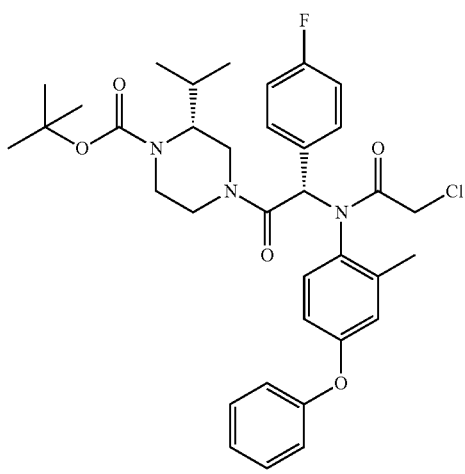

These two diastereoisomers were prepared in the same manner as in the preceding example in the form of colourless foam:
Least Polar Diastereoisomer (I-6 Dia1) (97 m; 30%)
  LCMS [M+H]=639 ($C_{35}H_{41}ClFN_3O_5$)
  $^1$H NMR (300 MHz, $CD_2Cl_2$): δ 7.94-8.57 (m; 0.9H); 7.35 (t; J=7.9 Hz; 1.9H); 7.05-7.25 (m; 3.1H); 6.72-6.93 (m; 5.0H); 6.58 (br d; J=2.6 Hz; 1.1H); 6.41 (s; 0.8H); 6.31 (br s; 0.3H); 4.63 (d; J=13.5 Hz; 0.8H) 4.40 (d; J=13.5 Hz; 0.3H); 3.51-4.06 (m; 4.8H); 3.03-3.45 (m; 1.0H); 2.41-2.96 (m; 1.6H); 2.02-2.21 (m; 0.8H); 1.82-1.95 (m; 2.1H); 1.43 (br s; 10.1H); 1.07 (d; J=6.5 Hz; 2.1H); 0.90 (d; J=6.5 Hz; 2.3H); 0.63 (d; J=6.5 Hz; 1.0H); 0.29 (d; J=6.5 Hz; 0.8H).
Most Polar Diastereoisomer (I-6 Dia2) (90 mg; 28%)
  LCMS [M+H]=639 ($C_{35}H_{41}ClFN_3O_5$)
  $^1$H NMR (300 MHz, $CDCl_3$): δ 8.00-8.10 (m; 1.0H); 7.30-7.40 (m; 2.1H); 6.98-7.18 (m; 3.1H); 6.73-6.90 (m; 5.1H); 6.52-6.58 (m; 1.0H); 6.34-6.39 (m; 1.0H); 4.70 (d; J=13.5 Hz; 0.7H); 4.49 (d; J=13.5 Hz; 0.4H); 3.50-4.00 (m; 4.8H); 3.10-3.30 (m; 0.7H); 2.86-3.07 (m; 0.4H); 2.54-2.85 (m; 1.5H); 2.30-2.47 (m; 0.4H); 1.80-1.87 (m; 2.8H); 1.54-1.60 (m; 2.6H); 1.42 (br s; 8.6H); 1.20 (d; J=6.6 Hz; 1.1H); 1.01 (d; J=6.6 Hz; 1.5H); 0.89 (d; J=6.6 Hz; 1.2H); 0.64 (d; J=6.6 Hz; 1.5H).

Examples I-7a and I-7b: Hydrochloride of the diastereoisomers of 2-chloro-N-[-1-(4-fluoro-phenyl)-2-((S)-3-isopropyl-piperazin-1-yl)-2-oxo-ethyl]-N-(2-methyl-4-phenoxy-phenyl)-acetamide I-7a

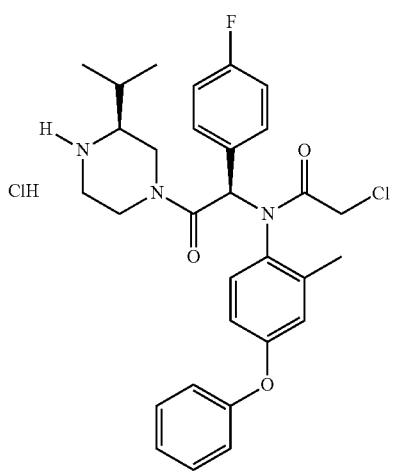

I-7b

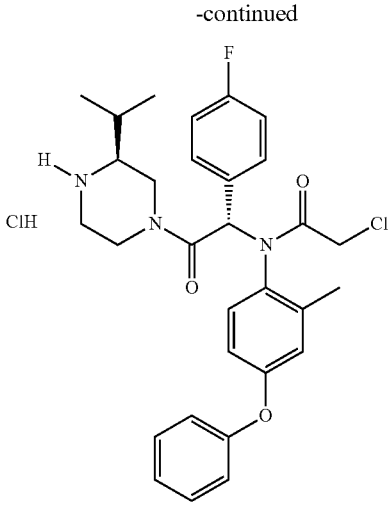

To a solution of one of the diastereoisomers I-5a and I-5b in 50 mL of DCM the HCl gas was added by bubbling. The reaction medium was left under agitation for 12 hours at RT. The DCM was evaporated and the residual oil precipitated in ethyl ether.
Starting from the First Diastereoisomer of Example I-5 (I-7 Dia1):
  Recovery of a white powder after filtration: (26 mg)
  LCMS [M+H]=538 ($C_{30}H_{34}Cl_2FN_3O_3$)
  $^1$H NMR (300 MHz, DMSO): δ 8.79-9.33 (m; 1.3H); 7.83 (t; J=9.0 Hz; 1.0H); 7.24-7.40 (m; 4.0H); 6.97-7.15 (m; 3.1H); 6.73-6.89 (m; 3.2H); 6.64 (d; J=2.7 Hz; 0.9H); 6.51-6.59 (m; 1.0H); 4.40-4.55 (br m; 1.1H); 3.86-4.09 (m; 3.6H); 3.45-3.60 (m; 0.7H); 2.78-3.05 (m; 2.8H); 1.79-2.00 (m; 4.5H); 1.61-1.77 (m; 0.7H); 0.97 (d; J=6.7 Hz; 6.0H).
Starting from the Second Diastereoisomer of Example I-5 (I-7 Dia2):
  Recovery of a white powder after filtration: (2.62 g)
  LCMS [M+H]=538 ($C_{30}H_{34}Cl_2FN_3O_3$)
  $^1$H NMR (300 MHz, DMSO): δ 8.78-9.51 (m; 1.9H); 7.82 (t; J=8.9 Hz; 0.9H); 7.20-7.41 (m; 4.0H); 6.97-7.16 (m; 3.1H); 6.71-6.90 (m; 3.1H); 6.61-6.70 (m; 1.9H); 4.46-4.60 (br m; 1.0H); 3.85-4.15 (m; 3.1H); 3.00-3.30 (m; 3.0H); 2.57-2.96 (m; 1.8H); 1.43-1.98 (m; 4.3H); 1.00 (dd; J=8.8 Hz; J=7.0 Hz; 2.7H); 0.71 (d; J=6.8 Hz; 1.6H); 0.65 (d; J=6.8 Hz; 1.5H).

Example I-8: Hydrochloride of 2-chloro-N-[-1-(4-fluoro-phenyl)-2-((R)-3-isopropyl-piperazin-1-yl)-2-oxo-ethyl]-N-(2-methyl-4-phenoxy-phenyl)-acetamide I-8a

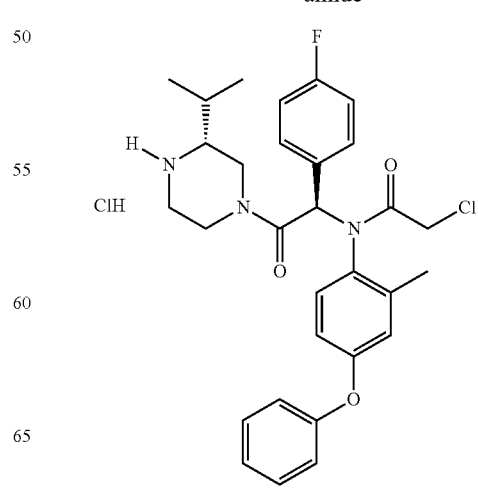

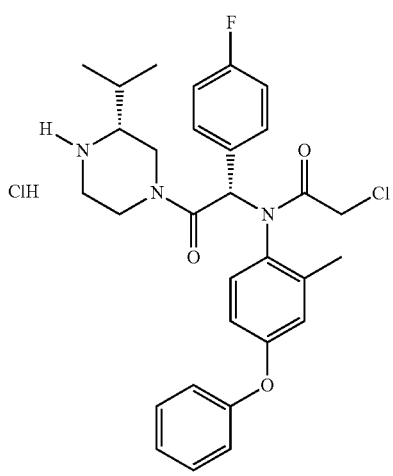

I-8b

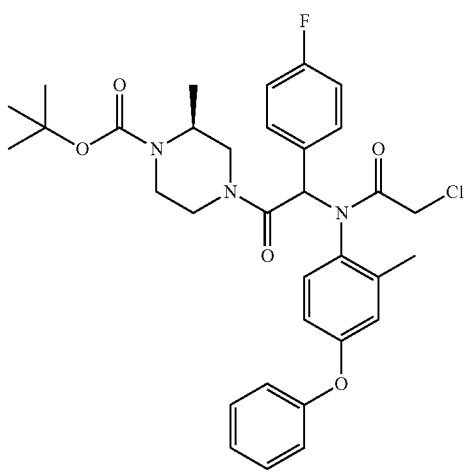

I-9

The same protocol as in the preceding example was followed starting from each of the diastereoisomers of Example I-6.

Starting from the First Diastereoisomer of Example I-6 (I-8 Dia1):

Recovery of a white powder after filtration: (34 mg; 56%)

LCMS [M+H]=538 ($C_{30}H_{34}Cl_2FN_3O_3$)

$^1$H NMR (300 MHz, DMSO): δ 8.79-9.33 (m; 1.3H); 7.83 (t; J=9.0 Hz; 0.9H); 7.24-7.40 (m; 4.0H); 6.97-7.15 (m; 3.1H); 6.73-6.89 (m; 3.1H); 6.64 (d; J=2.7 Hz; 1.0H); 6.51-6.59 (m; 1.0H); 4.41-4.56 (br m; 1.1H); 3.86-4.09 (m; 3.4H); 3.45-3.60 (m; 0.7H); 2.78-3.05 (m; 2.8H); 1.79-2.00 (m; 4.4H); 1.61-1.77 (m; 0.8H); 0.97 (d; J=6.7 Hz; 6.0H).

Starting from the Second Diastereoisomer of Example 16 (I-8 Dia2):

Recovery of a white powder after filtration: (30 mg; 54%)

LCMS [M+H]=538 ($C_{30}H_{34}Cl_2FN_3O_3$)

$^1$H NMR (300 MHz, DMSO): δ 8.78-9.51 (m; 1.5H); 7.82 (t; J=8.9 Hz; 1.0H); 7.20-7.41 (m; 4.0H); 6.97-7.16 (m; 3.1H); 6.71-6.90 (m; 3.2H); 6.61-6.70 (m; 1.9H); 4.46-4.60 (br m; 1.0H); 3.85-4.15 (m; 3.1H); 3.00-3.30 (m; 2.9H); 2.57-2.96 (m; 1.8H); 1.43-1.98 (m; 4.3H); 1.00 (dd; J=8.8 Hz; J=7.0 Hz; 2.7H); 0.71 (d; J=6.8 Hz; 1.6H); 0.65 (d; J=6.8 Hz; 1.5H).

Using the same operating modes and the same separation modes by silica chromatography as above, the following examples were prepared from diversely substituted anilines and piperazines. They were isolated either in the form of a mixture of two or four diastereoisomers (one example number for the same chemical structure) or in the form of separate diastereoisomers. In this latter case the nomenclature a/b was used to designate each of the diastereoisomers.

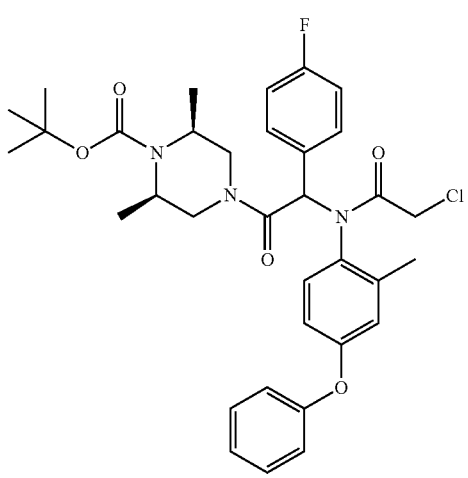

I-10

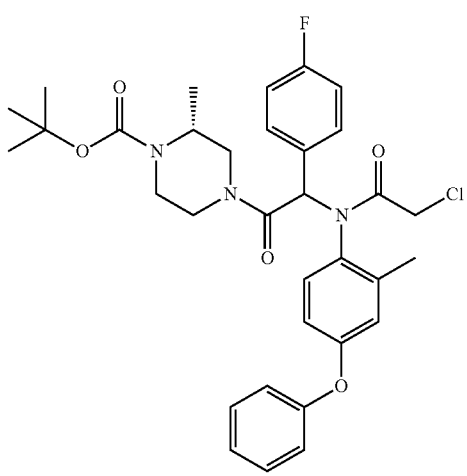

I-11

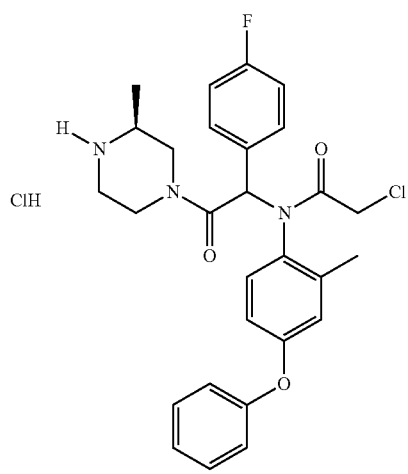
I-12
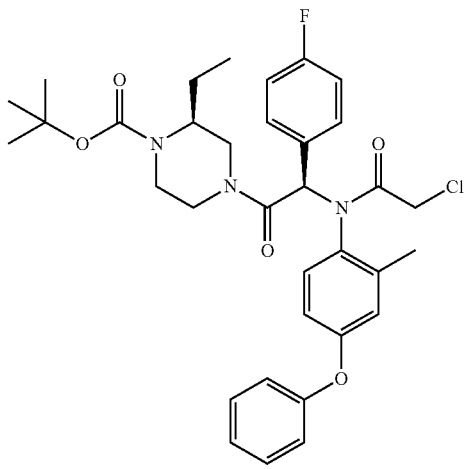
I-15a
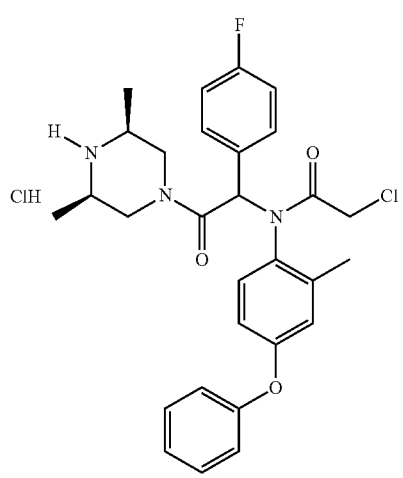
I-13
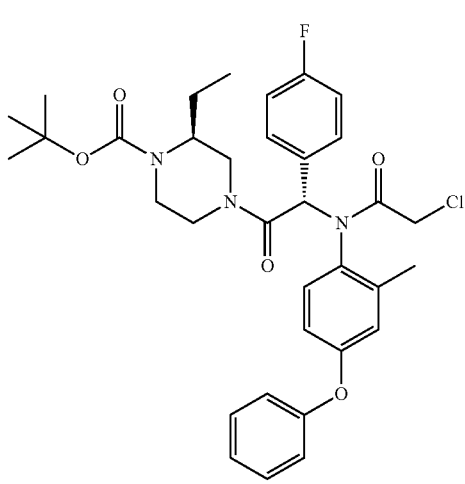
I-15b
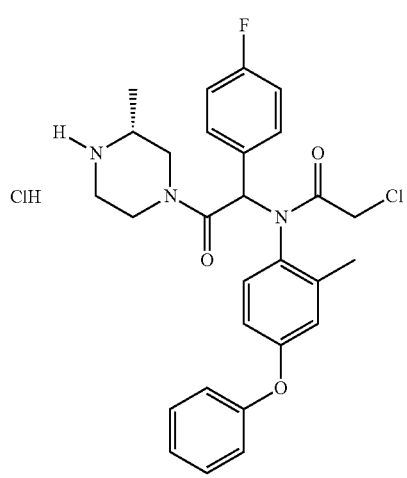
I-14
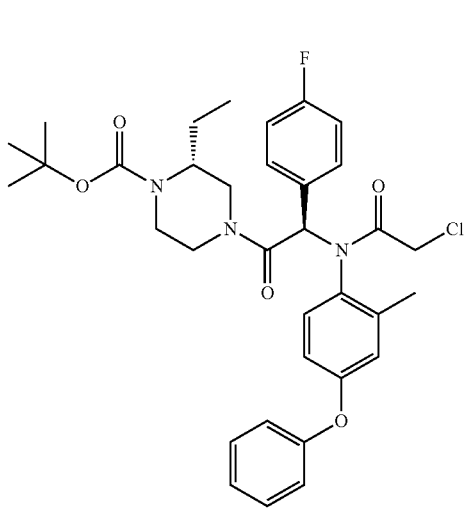
I-16a -continued
I-16b
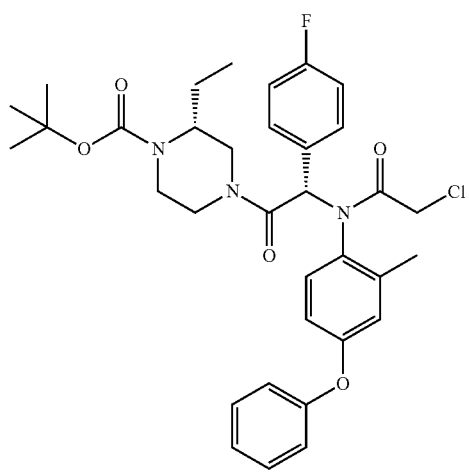
I-18a
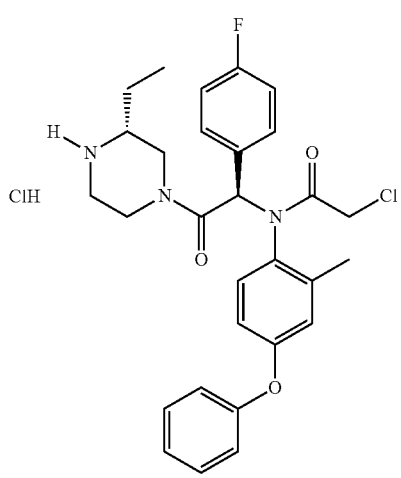
I-17a
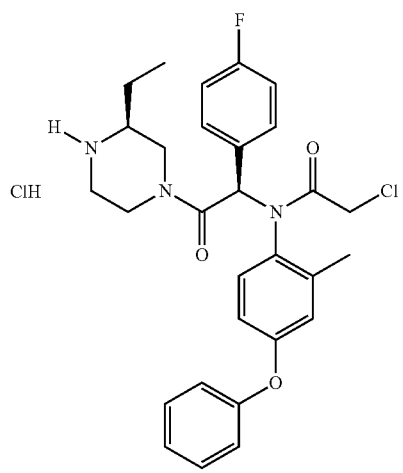
I-18b
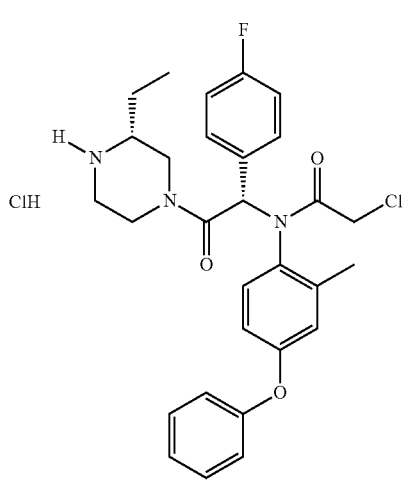
I-17b
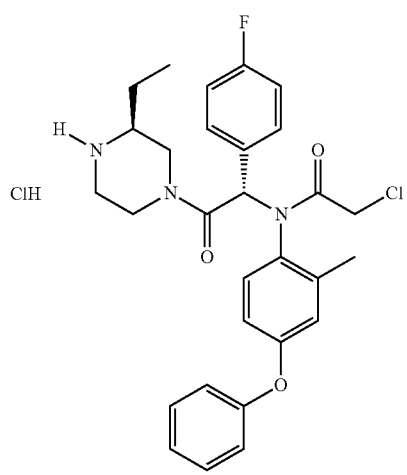
I-19a
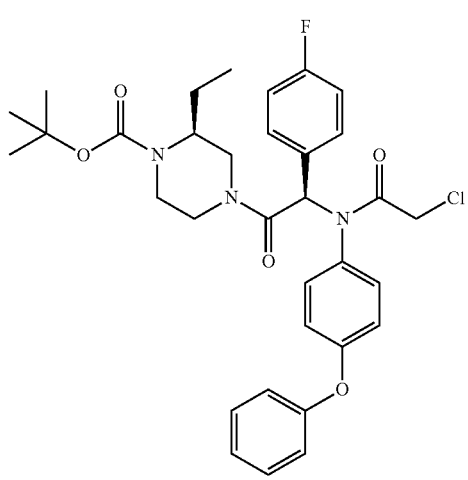

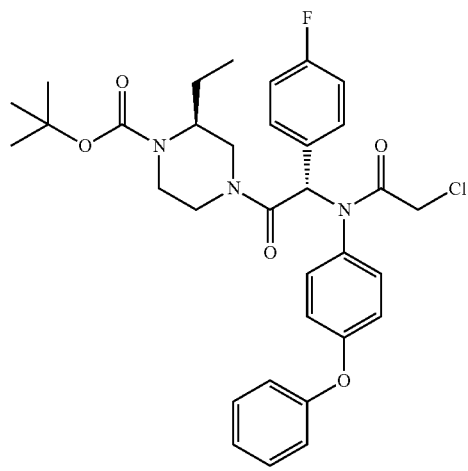
I-19b
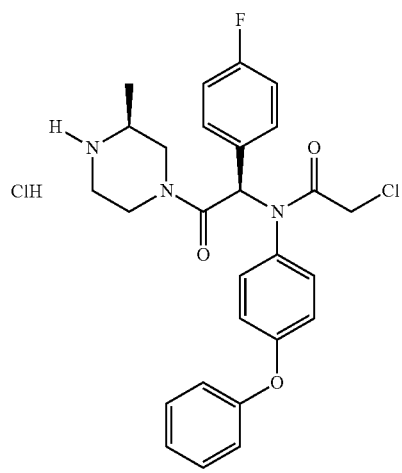
I-21a
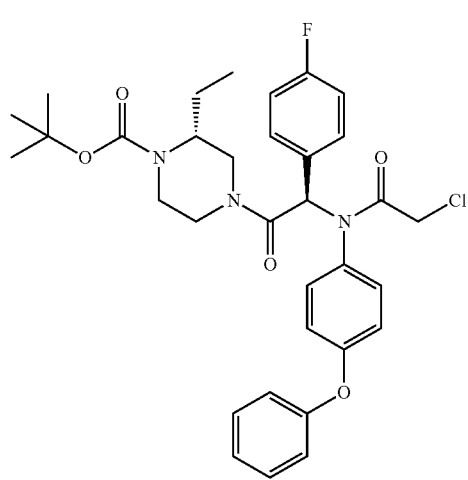
I-20a
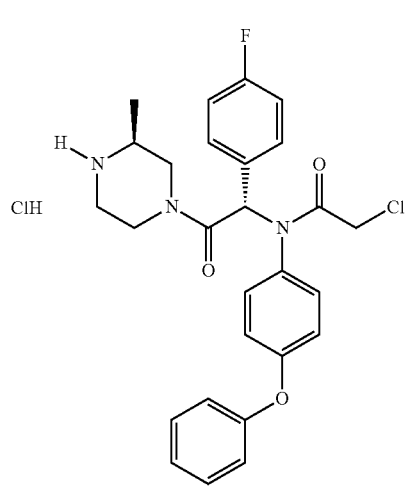
I-21b
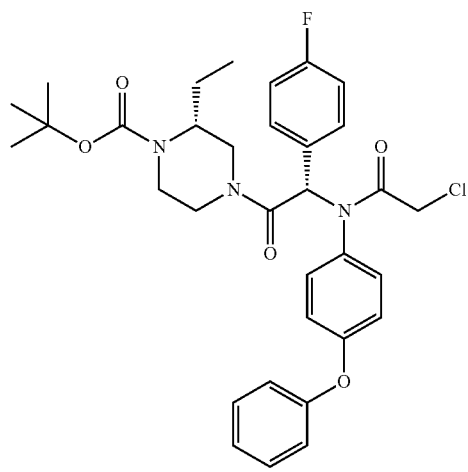
I-20b
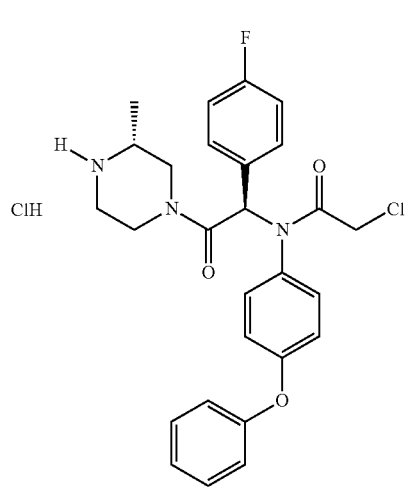
I-22a

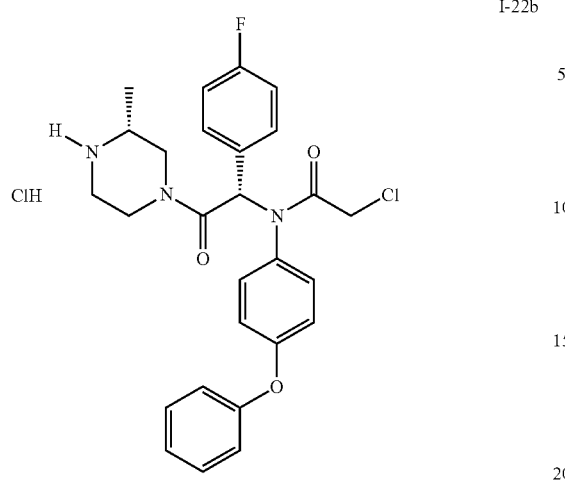
I-22b
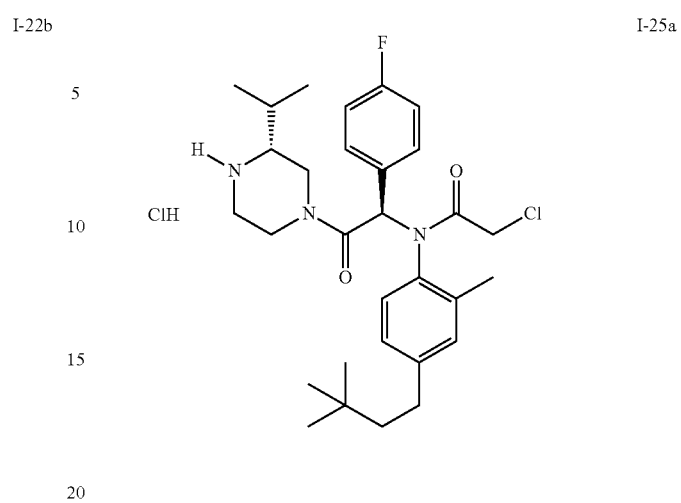
I-25a
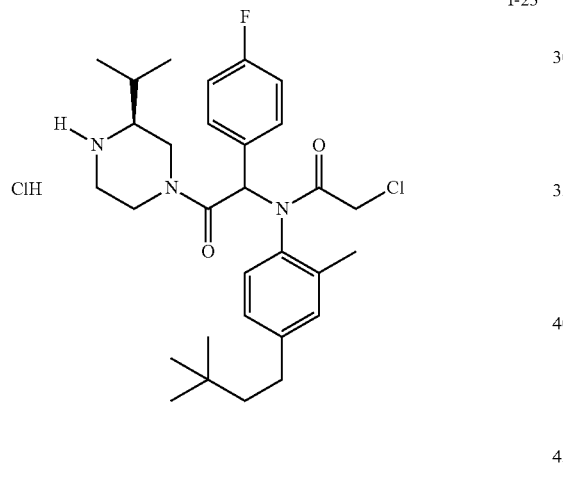
I-23
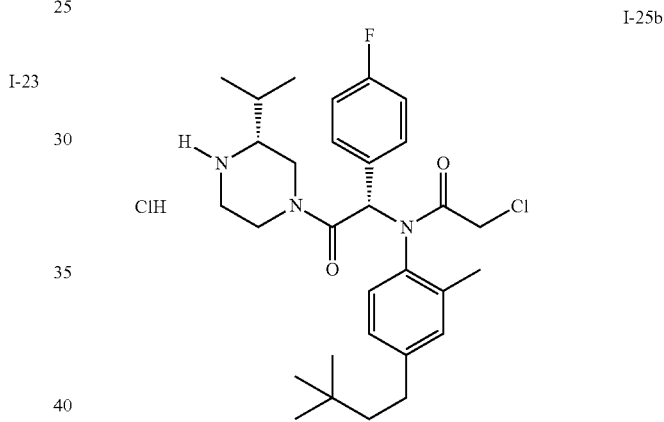
I-25b
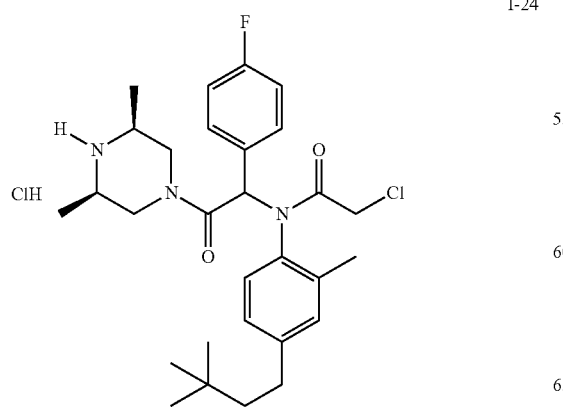
I-24
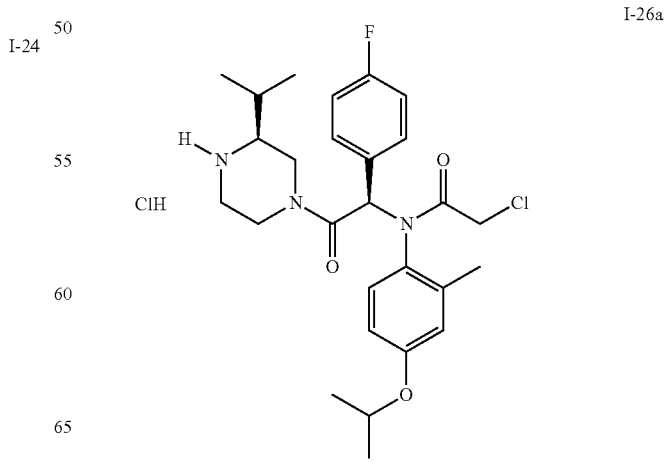
I-26a

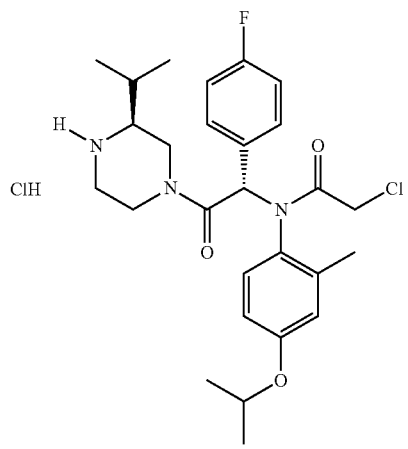
I-26b
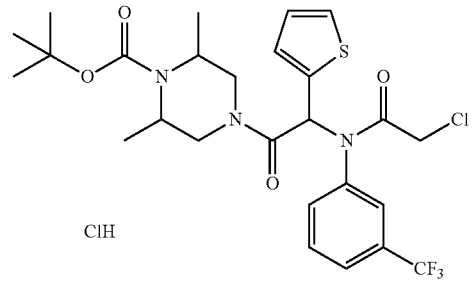
I-28
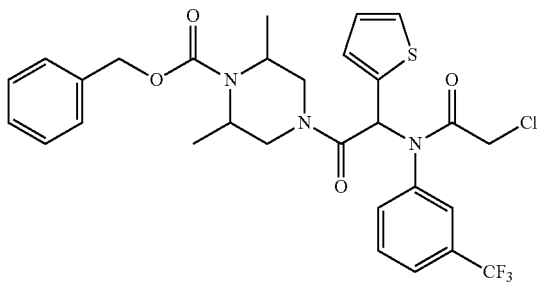
I-29
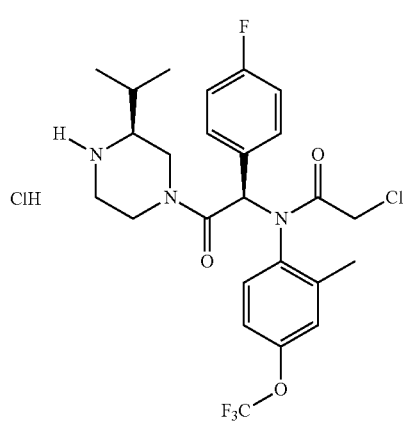
I-27a
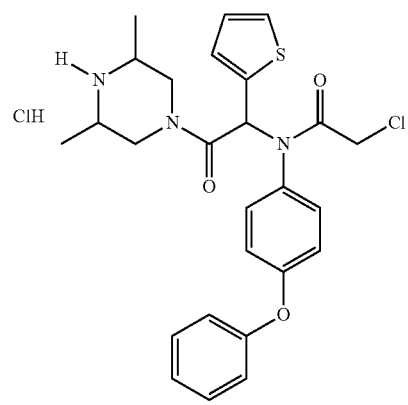
I-30
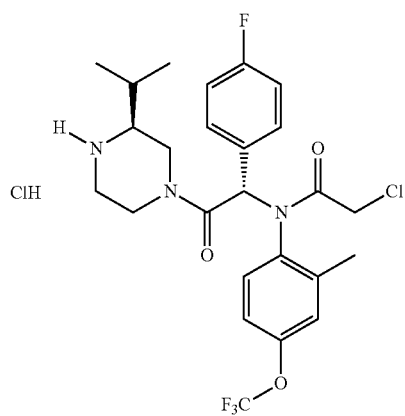
I-27b
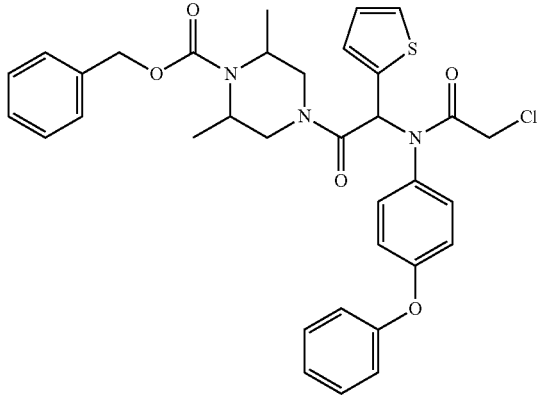
I-31
The following examples were obtained by replacing the ethyl ester of (4-fluoro-phenyl)-oxo-acetic acid by ethyl thiophene-2-glyoxylate and following the same operating modes as previously.

I-32 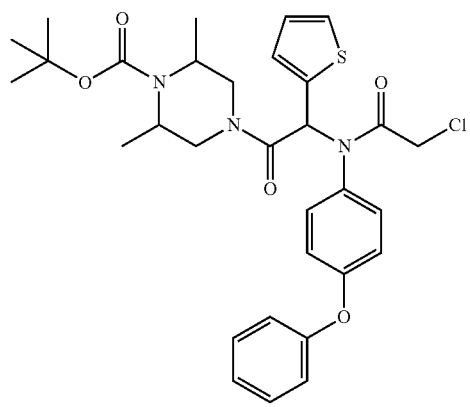
I-33 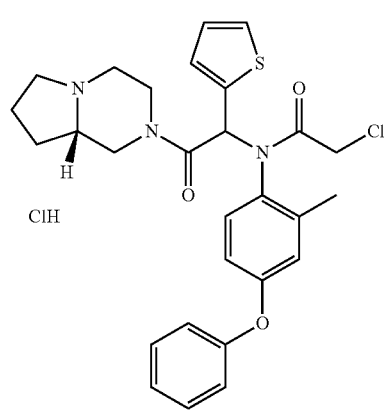
I-34 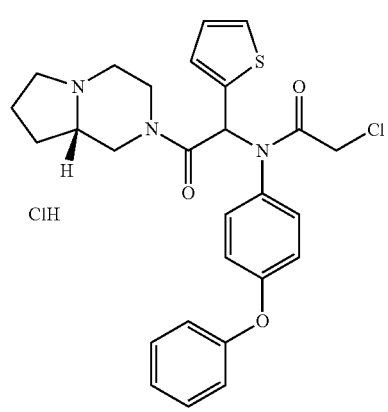
I-35 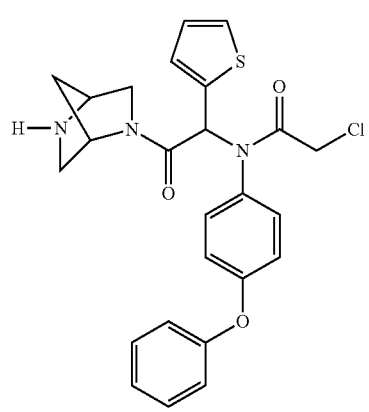
I-36 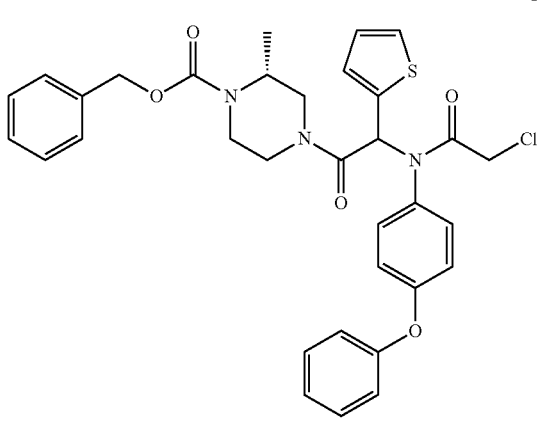
I-37 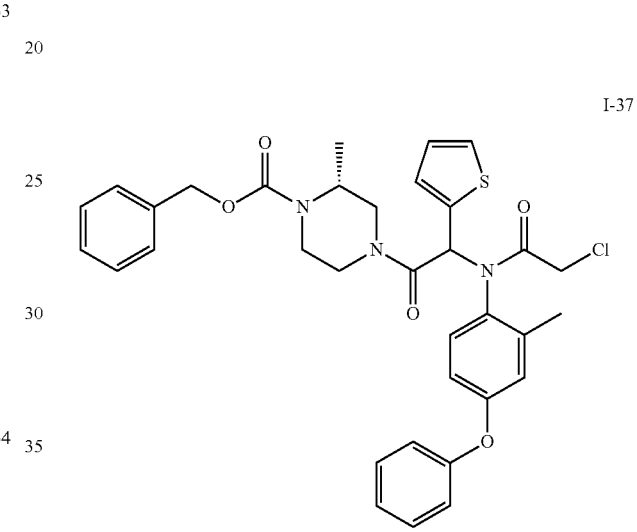
I-38 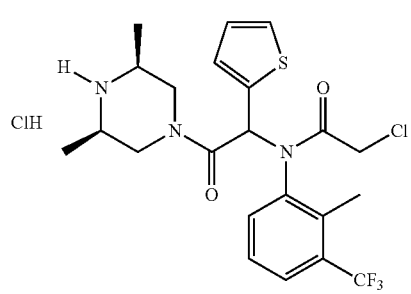
I-39 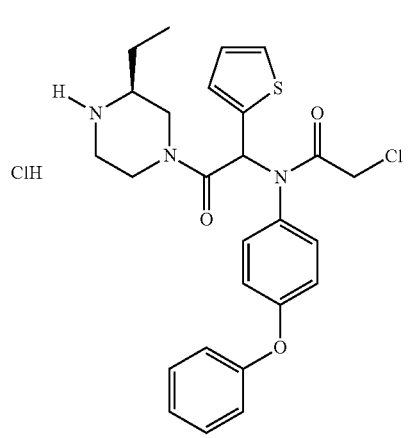

I-40a
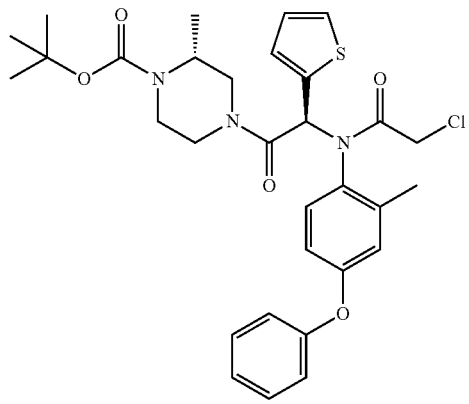
I-40b
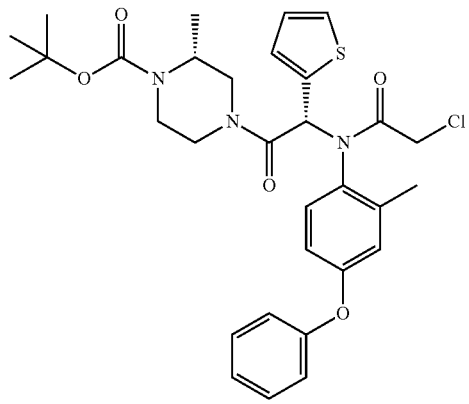
I-41a
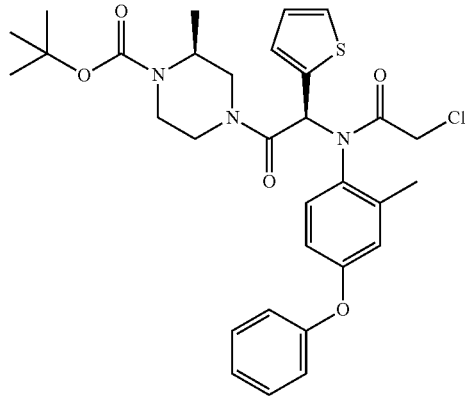
I-41b
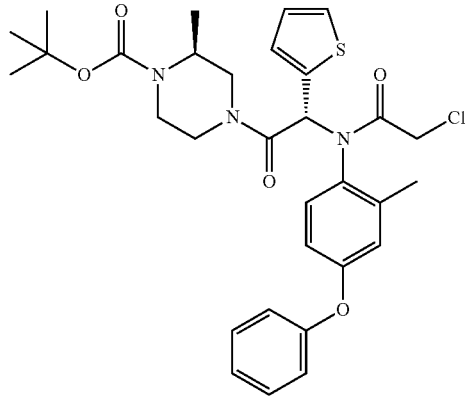
I-42a
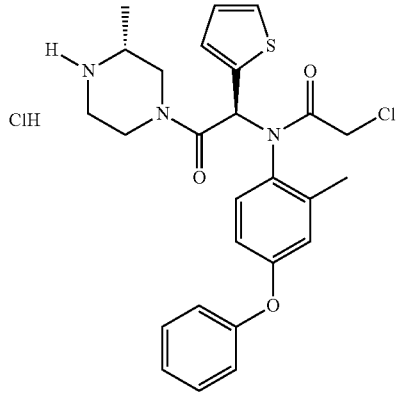
I-42b
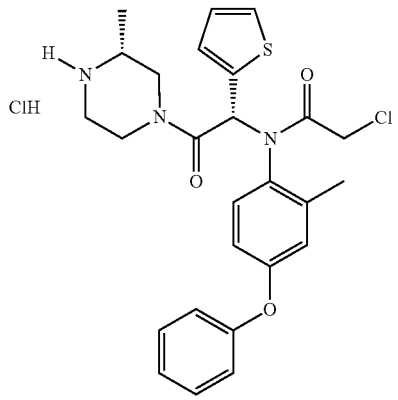
I-43a
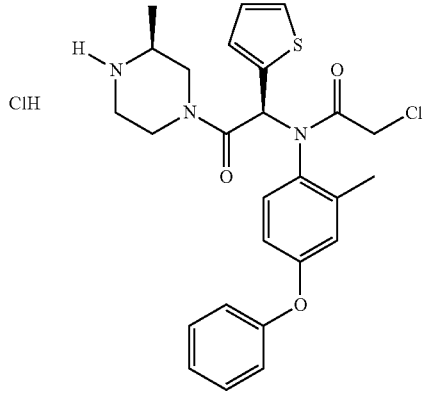
I-43b
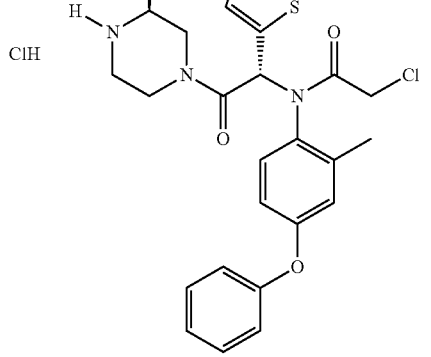

I-44
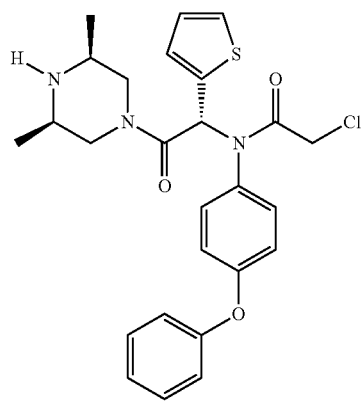
I-45
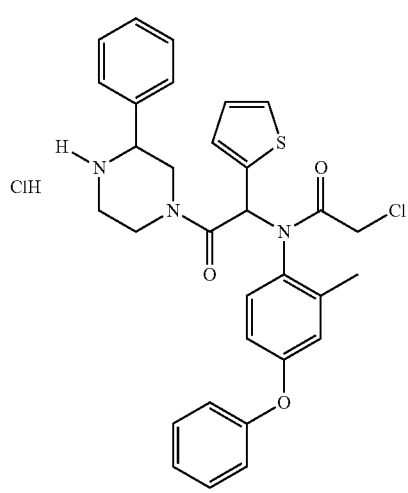
I-46a
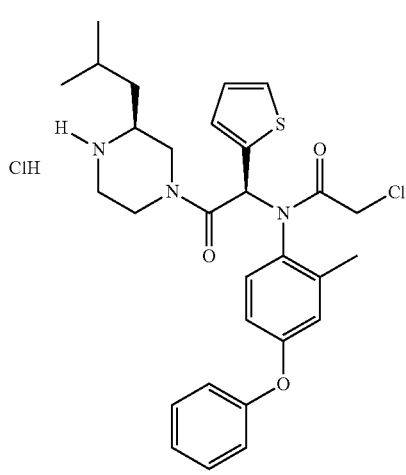
I-46b
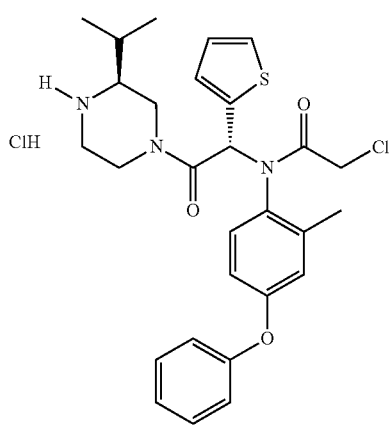
I-47a
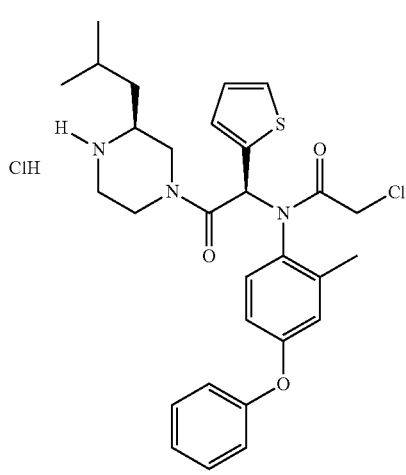
I-47b
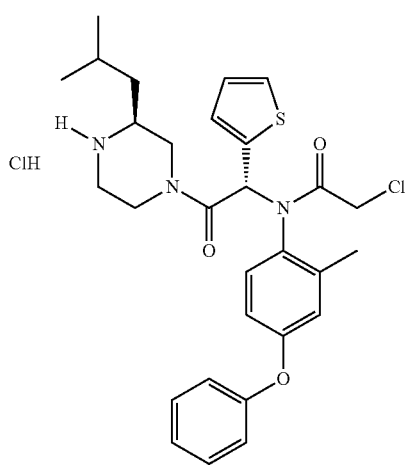

I-48
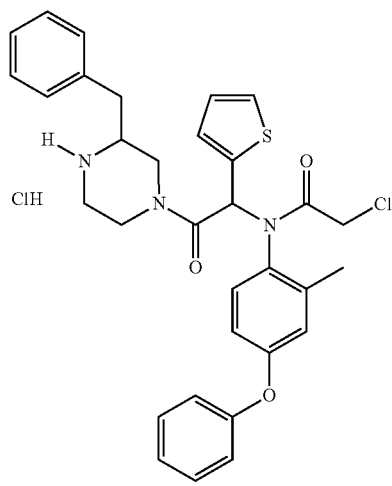
I-49
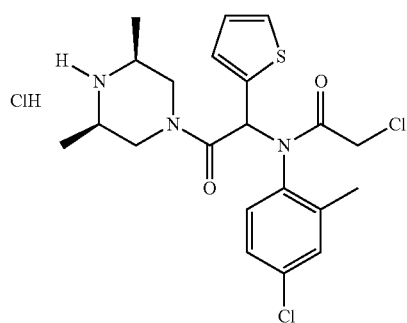
I-50a
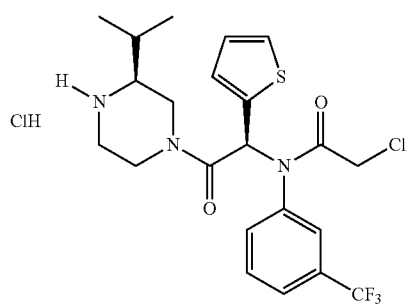
I-50b
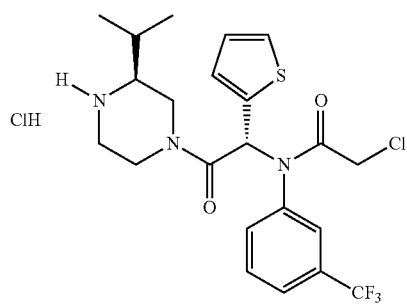
I-51a
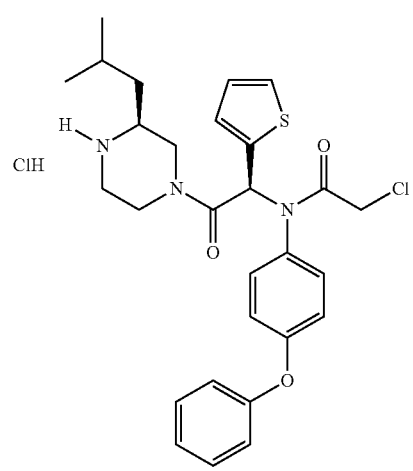
I-51b
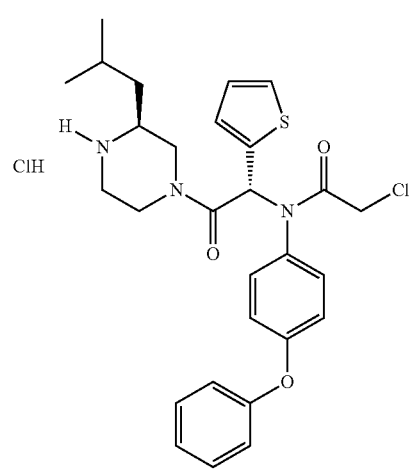
I-52a
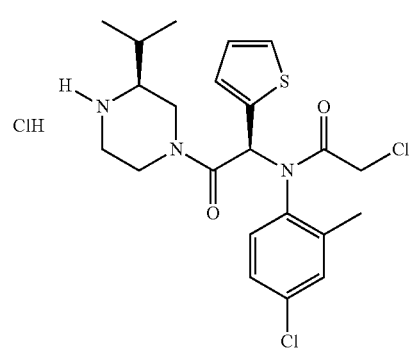
I-52b
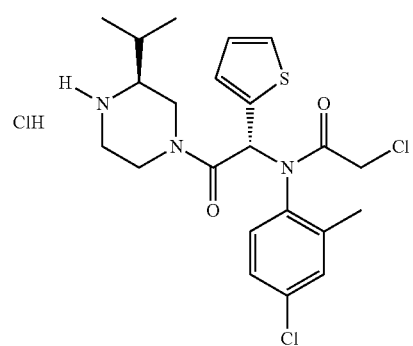

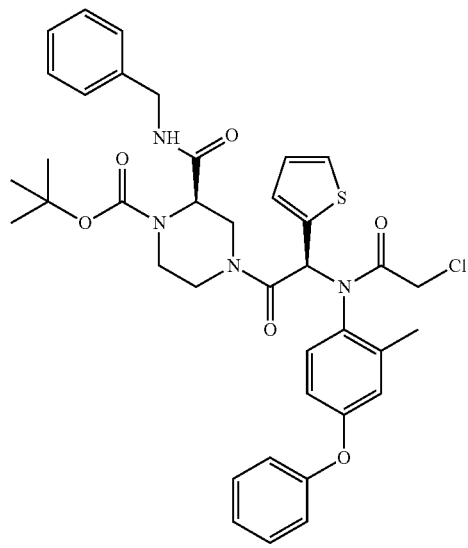
I-53a
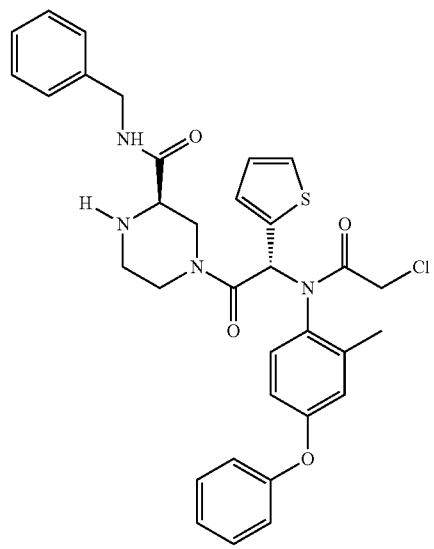
I-54b
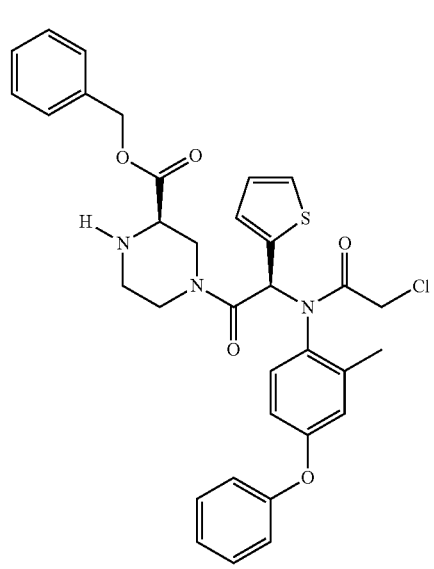
I-55a
I-53b
I-54a
I-55b
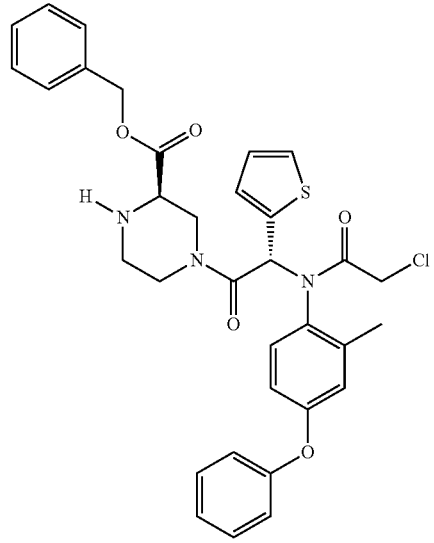

I-56a
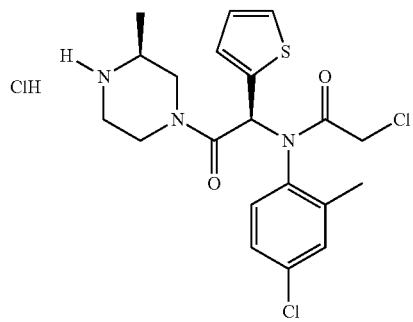
I-56b
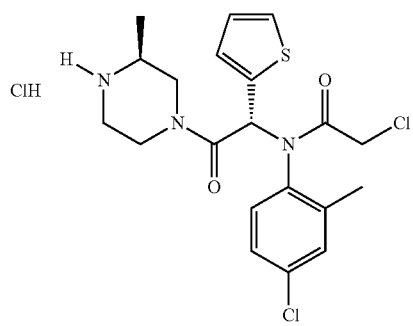
I-57
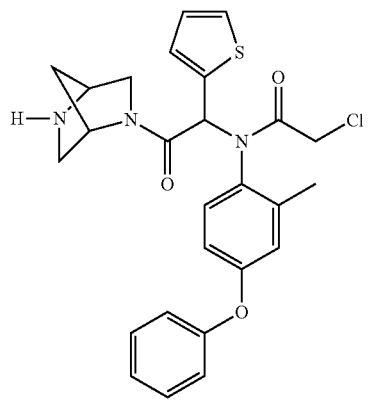
I-58
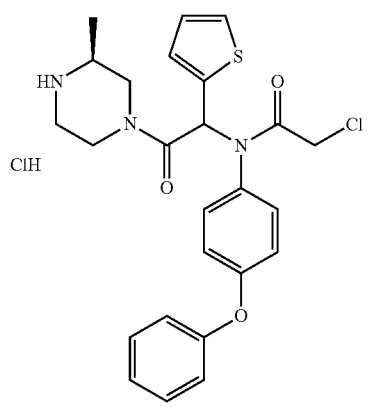
I-59
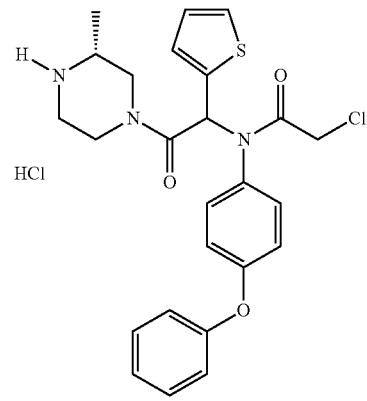
I-60
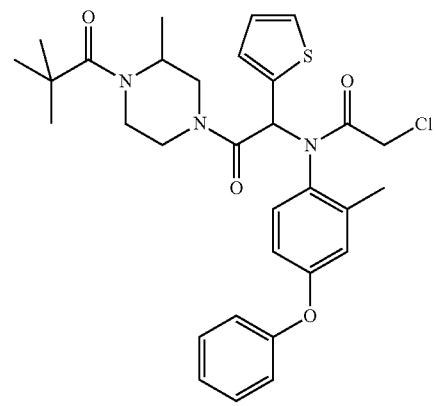
I-61
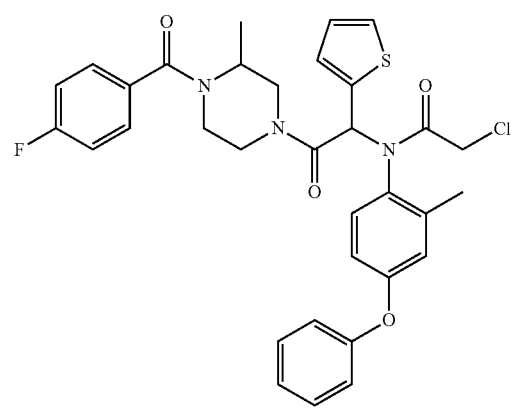
I-62
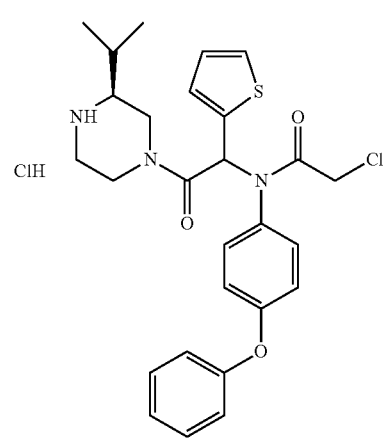

I-63

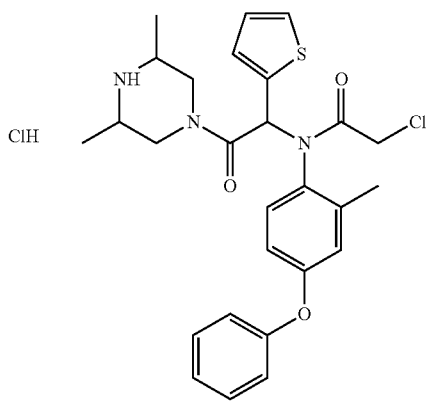

II—Pharmacological Study of the Compounds of the Present Invention

1) Cytotoxicity Tests

Assay with Various Compounds According to the Invention on MCF-7, MCF-7/Adr, HL-60, HL-60/R10, HT29, Mia Paca2, Panc-1 and SK-OV-3 cell lines:

The effects of the compounds of the invention on the proliferation of cancer cells were studied on different human cancer cell lines of different tissue origin (MCF-7: breast cancer, MCF-7/adr adriamycin-resistant breast cancer, HL-60: acute promyelocytic leukaemia, HL-60/R10: doxorubicin-resistant acute promyelocytic leukaemia, HT29: colon adenocarcinoma, Mia Paca2: pancreatic tumour, Panc-1: pancreatic exocrine tumour, SK-OV-3: cisplatin- and adriamycin resistant ovarian cancer). The cancer cells used for this study were incubated at 37° C. in the presence of one of the compounds of the invention added to the culture medium at different concentrations.

The cancer cell lines were obtained from ATCC (American Type Culture Collection) for MCF-7, from Hôpital de la Pitié Salpetrière for MCF-7/adr and from Oncodesign (Dijon, France) for HL-60, HL-60/R10, HT29, MiaPaCa2, Panc-1 and SK-OV-3. They were cultured in RPMI 1640 medium containing 2 mM L-Glutamine supplemented with 10% foetal calf serum (Lonza; Verviers, Belgium). All the cell lines were held in culture at 37° C. in a humid atmosphere containing 5% $CO_2$. Cell proliferation was assessed using the ViaLight® Plus Assay Kit (Lonza; Verviers, Belgium) following the manufacturer's instructions. The cells were seeded in 96-well culture plates compatible with luminescence read-off (white plates with transparent bottom) in a proportion of 5 000 to 10 000 cells per well in 100 µl of culture medium. After a pre-incubation time of 24 hours at 37° C., the compounds of the invention dissolved in dimethylsulfoxide (DMSO) were individually added to each well in a proportion of 0.5 µl per well. After 72 hours' incubation at 37° C. in a humid atmosphere containing 5% $CO_2$, 50 µl of lysis buffer were added to each well and 15 minutes later 100 µl of ATP measuring agent were added. The plates were read under a luminometer to evaluate cell viability. The data obtained was processed by computer to obtain the $EC_{50}$ value i.e. the concentration value of each of the compounds which induces 50% cell viability compared with a control value (0.5% DMSO alone).

The results obtained are given in following Tables 1 and 2.

TABLE 1

Results obtained with cell lines HL-60, HL60/R10, MCF-7 and MCF-7/adr ($EC_{50}$ expressed in nM)

| Example No | $EC_{50}$ (nM) | | | |
|---|---|---|---|---|
| | HL-60 | HL60/R10 | MCF-7 | MCF-7/adr |
| I-1 dia1 | 1799 | −219 | −2500 | 338 |
| I-1 dia2 | 824 | 23 | 1304 | 39 |
| I-2 dia1 | 728 | 40 | 2091 | 49 |
| I-2 dia2 | 2061 | 472 | 2500 | 645 |
| I-3 dia1 | 1311 | 15 | 927 | 55 |
| I-3 dia2 | 504 | 2 | 301 | 9 |
| I-4 dia1 | 648 | 4 | 315 | 13 |
| I-4 dia2 | 1321 | 62 | 863 | 166 |
| I-7 dia1 | 2500 | 604 | 2500 | 618 |
| I-7 dia2 | 1938 | 26 | 1954 | 98 |
| I-8 dia1 | 2029 | 54 | 1740 | 148 |
| I-8 dia2 | 1737 | 312 | 2410 | 477 |
| I-9 | 771 | 99 | 2500 | 108 |
| I-10 | 641 | 131 | 2500 | 151 |
| I-11 | 939 | 68 | 2500 | 102 |
| I-12 | 2321 | 82 | 1787 | 421 |
| I-13 | 1989 | 88 | 2500 | 532 |
| I-14 | 1848 | 95 | 2500 | 232 |
| I-16 dia1 | 1478 | 450 | 2500 | 527 |
| I-16 dia2 | 1913 | 317 | 2500 | 443 |
| I-17 dia1 | 2313 | 353 | 2500 | 898 |
| I-17 dia2 | 1604 | 49 | 1994 | 152 |
| I-18 dia1 | 1596 | 140 | 2500 | 485 |
| I-18 dia2 | 352 | 44 | 591 | 152 |
| I-19 dia1 | 516 | 97 | 2500 | 128 |
| I-19 dia2 | 453 | 24 | 2500 | 35 |
| I-20 dia1 | 196 | 80 | 1571 | 73 |
| I-20 dia2 | 1478 | 139 | 2500 | 165 |
| I-21 dia1 | 2447 | 13 | 1950 | 93 |
| I-21 dia2 | 630 | 8 | 869 | 10 |
| I-22 dia1 | 1995 | 17 | 569 | 131 |
| I-22 dia2 | 1149 | 18 | 430 | 34 |
| I-23 | 559 | 12 | nd | nd |
| I-24 | 626 | 15 | nd | nd |
| I-25 dia1 | 1122 | 43 | nd | nd |
| I-25 dia2 | 819 | 103 | nd | nd |
| I-26 dia1 | 2447 | 13 | 1950 | 93 |
| I-26 dia2 | 630 | 8 | 869 | 10 |
| I-27 dia1 | 1995 | 17 | 569 | 131 |
| I-27 dia2 | 1149 | 18 | 430 | 34 |
| I-28 | 623 | 206 | nd | nd |
| I-29 | 939 | 38 | 1032 | 54 |
| I-30 | 202 | 10 | 1006 | 44 |
| I-31 | 766 | 64 | 2500 | 89 |
| I-32 | 175 | 78 | 2500 | 58 |
| I-33 | 2500 | 157 | 2500 | 394 |
| I-34 | 1123 | 30 | 1775 | 100 |
| I-35 | 300 | 249 | 632 | 863 |
| I-36 | 372 | 28 | 2500 | 24 |
| I-37 | 967 | 154 | 2500 | 156 |
| I-38 | 2500 | 189 | 2500 | 851 |
| I-39 | 1814 | 9 | 776 | 52 |
| I-40 dia1 | 2129 | 248 | 2500 | 371 |
| I-40 dia2 | 2500 | 487 | 2500 | 827 |
| I-43 dia2 | 1886 | 20 | 1424 | 126 |
| I-44 | 215 | 7 | nd | nd |
| I-45 | 2136 | 17 | nd | nd |
| I-46 dia1 | 2500 | 318 | 2500 | 544 |
| I-46 dia2 | 449 | 10 | 1184 | 58 |
| I-47 dia1 | 936 | 54 | nd | nd |
| I-47 dia2 | 849 | 8 | nd | nd |
| I-48 | 1991 | 10 | nd | nd |
| I-49 | 1166 | 321 | nd | nd |
| I-50 dia1 | 2102 | 259 | nd | Nd |
| I-50 dia2 | 841 | 8 | nd | nd |
| I-51 dia1 | 145 | 96 | nd | nd |
| I-51 dia2 | 3 | 1 | nd | nd |
| I-52 dia1 | 2500 | 194 | nd | nd |
| I-52 dia2 | 223 | 24 | nd | nd |

TABLE 1-continued

Results obtained with cell lines HL-60, HL60/R10, MCF-7 and MCF-7/adr (EC$_{50}$ expressed in nM)

| Example No | EC$_{50}$ (nM) | | | |
|---|---|---|---|---|
| | HL-60 | HL60/R10 | MCF-7 | MCF-7/adr |
| I-53 dia1 | 1981 | 645 | 2064 | 462 |
| I-53 dia2 | 547 | 305 | nd | nd |
| I-58 | 1058 | 11 | 870 | 88 |
| I-59 | 956 | 16 | 745 | 106 | nd = non-determined

TABLE 2

Results obtained with other cell lines (EC$_{50}$ expressed in nM)

| Example No | EC$_{50}$ (nM) | | | |
|---|---|---|---|---|
| | HT29 | Mia PaCa2 | Panc-1 | SK-OV-3 |
| I-3 dia2 | 1 | 2 | 1 | 1 |
| I-7 dia2 | 8 | 13 | 5 | 7 |
| I-43 dia2 | 10 | 18 | 7 | 9 |
| I-46 dia2 | 6 | 10 | 4 | 6 |
| I-50 dia2 | 9 | 2200 | 9 | 11 |

Following Tables 3 and 4 illustrate the gain in cytotoxic activity on the resistant HL60/R10 line, obtained with the compounds having a piperazine substituted at alpha position of nitrogen 4 of the piperazine compared with a non-substituted piperazine and/or substituted at another position of the piperazine. The best cytotoxic activity is obtained with the absolute configuration (S) of this substitution.

TABLE 3

Results obtained with different substitutions of piperazine

| Example | EC$_{50}$ (nM) | |
|---|---|---|
| | HL-60 | HL-60/R10 |
| Comparative example | 1627 | 226 |
| I-12 | 2321 | 82 |
| I-14 | 1989 | 88 |
| I-13 | 1848 | 95 |

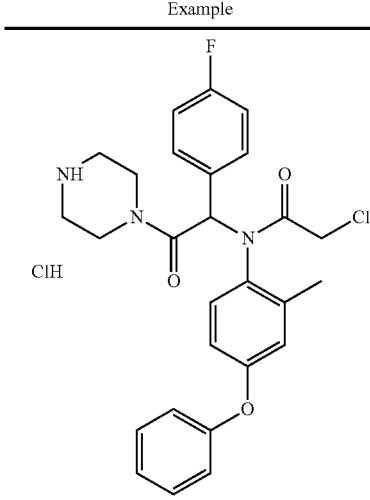

TABLE 4

Results obtained with different substitutions of piperazine

| Example | EC₅₀ (nM) HL-60 | EC₅₀ (nM) HL-60/R10 |
|---|---|---|
| Comparative example (structure) | 579 | 21 |
| I-58 | 1058 | 11 |
| Comparative example (structure) | 662 | 65 |
| I-59 | 966 | 16 |
| Comparative example (structure) | 311 | 38 |

Assay with Compound I-43b on the NCI 60 Tumor Cell Lines:

Compound I-43b has been tested in the NCI 60 cell line panel. This screen utilizes 60 different human tumor cell lines, representing leukemia, melanoma, lung cancer, colon cancer, CNS cancer, ovarian cancer, breast cancer, prostate cancer and renal cancer.

The 60 human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 h prior to addition of the tested drug.

After 24 h, two plates of each cell line are fixed in situ with TCA, to represent a measurement of the cell population for each cell line at the time of drug addition (Tz). Compound I-43b is solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Aliquots of 100 μl of these different drug dilutions are added to the appropriate microtiter wells already containing 100 µl of medium, resulting in the required final drug concentrations.

Following drug addition, the plates are incubated for an additional 48 h at 37° C., 5% $CO_2$, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero (Tz), control growth (C), and test growth in the presence of drug at the five concentration levels (Ti)], the percentage growth is calculated at each of the drug concentrations levels. Percentage growth inhibition is calculated as:

[(Ti−Tz)/(C−Tz)]×100 for concentrations for which Ti>/=Tz

[(Ti−Tz)/Tz]×100 for concentrations for which Ti<Tz.

Three dose response parameters are calculated for each experimental agent. Growth inhibition of 50% (GI50) is calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from [(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested.

Figure 3:
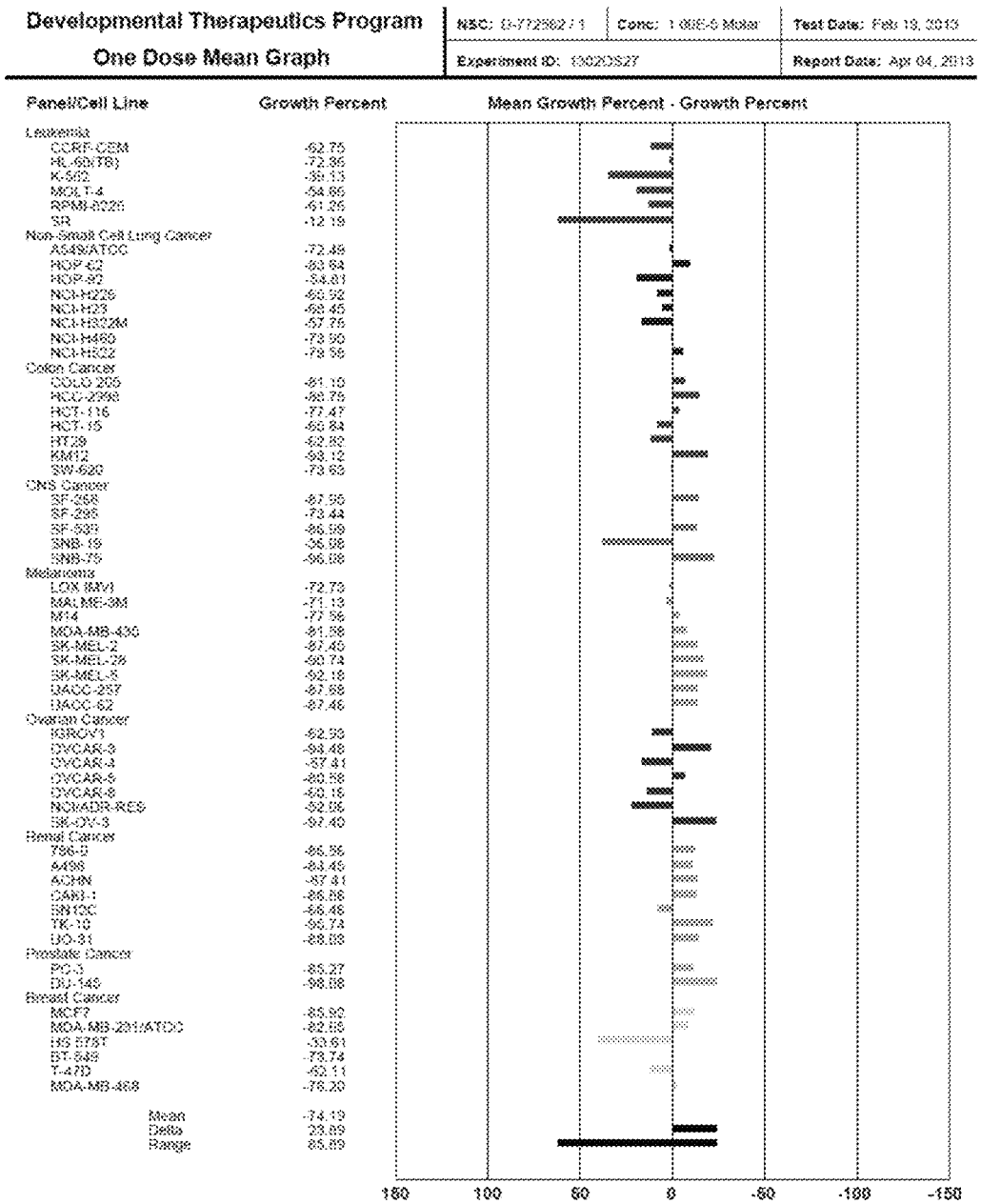
FIG. 3 presents the mean growth percent of the NCI 60 cell lines in the presence of compound I-43b at a concentration of 10 M.

The output from the single dose screen is reported as a mean graph on FIG. 3. Compound I-43b shows selective growth inhibition on all these tumor cell lines at the concentration of 10 µM. This screen is unique in that the complexity of a 60 cell line dose response produced by compound I-43b results in a biological response pattern which can be utilized in pattern recognition algorithms (COMPARE program. See: http://dtp.cancer.gov/docs/compare/compare.html). Using these algorithms, it has been possible to determine that the response pattern of compound I-43b is unique and not similar to that of any of the standard prototype compounds included in the NCI database.

Figure 4A:
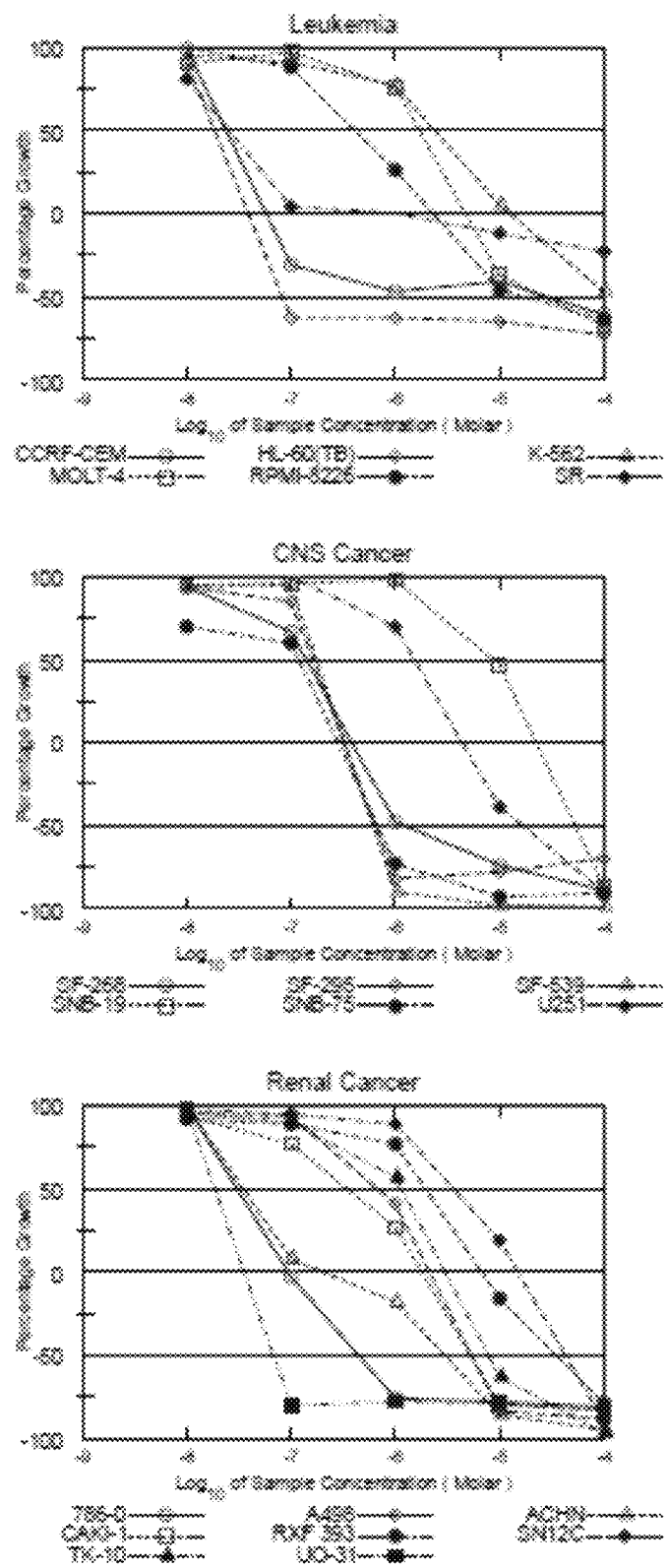
FIGS. 4A, 4B and 4C represent the percentage growth of the NCI 60 cell lines in the presence of compound I-43b at five different concentrations.
Figure 4B:
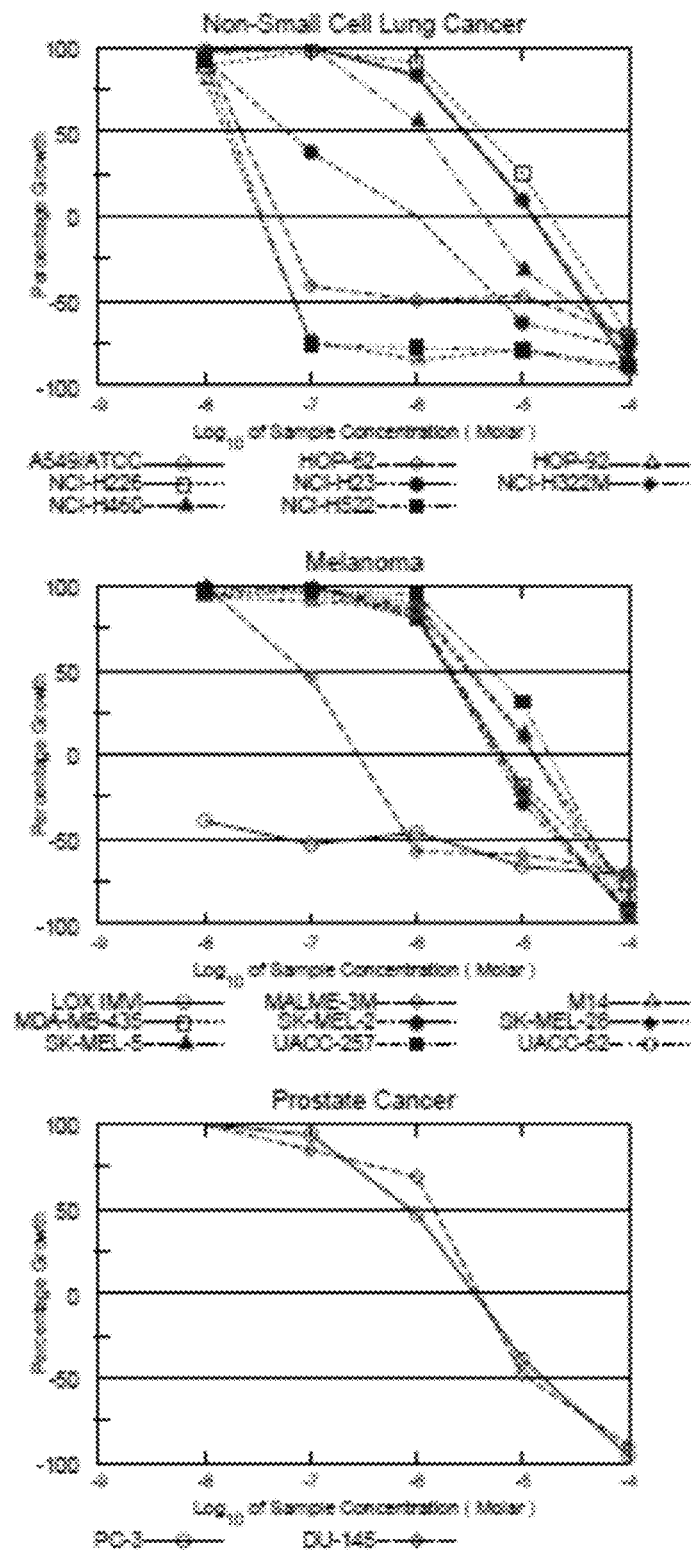
Figure 4C:
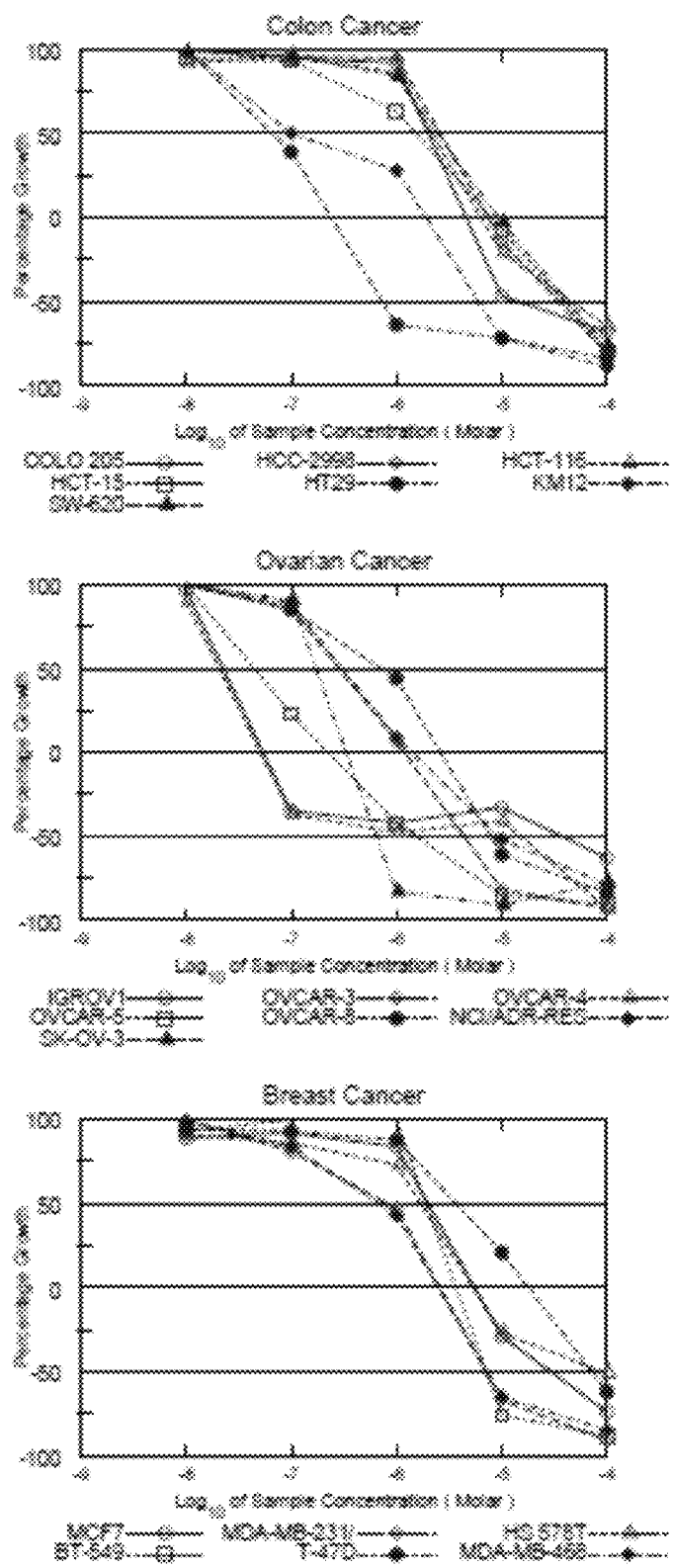

In addition, Compound I-43b has been evaluated against the 60 cell panel at five concentration levels to determine the concentration inhibiting 50% of cell proliferation of each cell line. The results are presented on FIGS. 4A, 4B and 4C (with X axis: $Log_{10}$ sample concentration (Molar)-Y axis: Percentage Growth).

Figure 2:
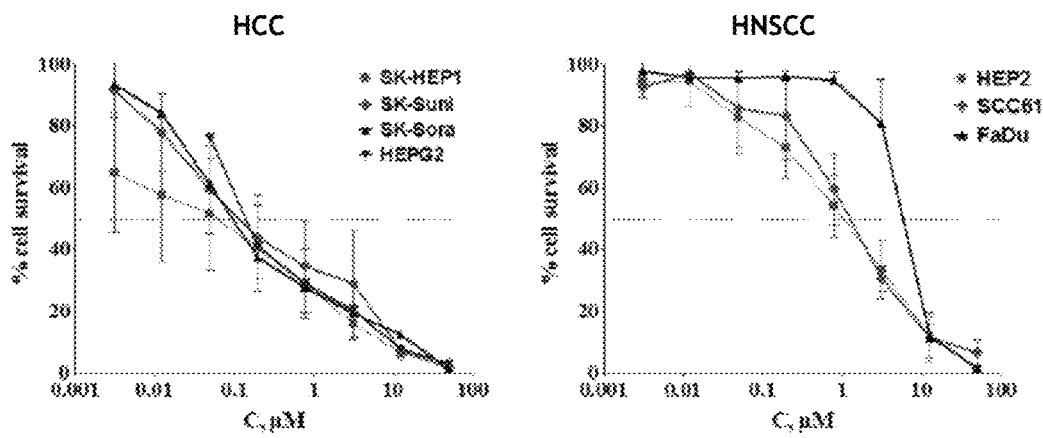
FIG. 2 presents the results of cell proliferation inhibition of 3 human cancer cell lines established from head & neck (HNSCC) and 4 human cancer cell lines established from hepatocarcinoma (HCC) by compound I-43b.

Assay with Compound I-43b on HNSCC and HCC:

Compound I-43b has been tested in 3 human cancer cell lines established from Head & Neck (HNSCC) and in 4 human cancer cell lines established hepatocarcinoma (HCC). In all cases, compound I-43b inhibited cell proliferation in a concentration dependent manner (see results on FIG. 2). Cell proliferation has been evaluated using the MTT assay after 72 hours of treatment.

2) Determination of Aqueous Solubility

Aqueous solubility is a major physicochemical parameter for improving the ADME properties (Absorption, Distribution, Metabolism and Excretion) in a molecule (Drug-like properties: concepts, structure design and methods, Edward Harvel Kerns, Li Di; Academic Press, 2008).

The aqueous solubility of each compound was measured at pH 7.4. It was measured using HPLC on the supernatants obtained by centrifugation after saturation of the media with excess compound after an agitation time of 24 h and at a temperature of 20° C. The preparation and treatment of the samples was robotized.

Table 5 shows the gain in aqueous solubility obtained for a compound of the invention I-58 compared with a non-substituted piperazine or substituted at another position.

TABLE 5

Aqueous solubility obtained with different piperazine substitutions.

| Example | Solubility (µg/mL) |
|---|---|
| Comparative example | 68 |
| I-58 | 203 |

TABLE 5-continued

Aqueous solubility obtained with different piperazine substitutions.

| Example | Solubility (µg/mL) |
|---|---|
| 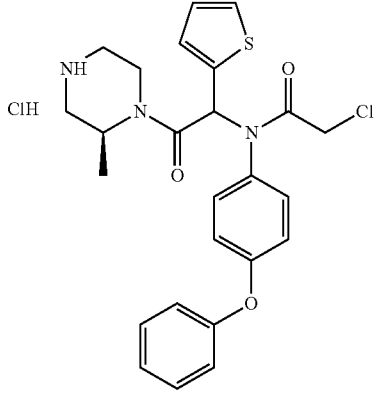<br>Comparative example | 105 |
| 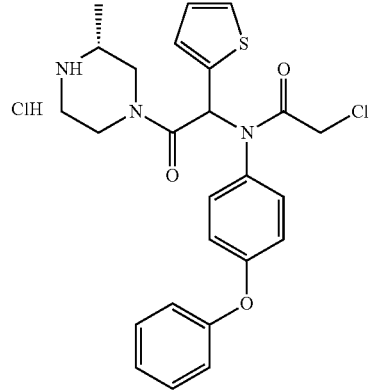<br>I-59 | 152 |
| 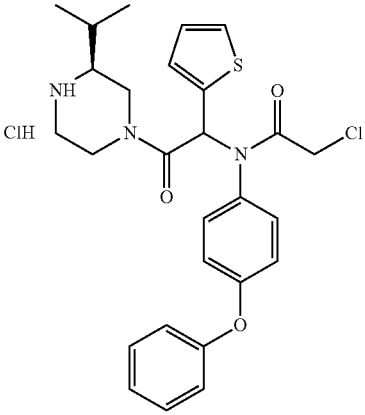<br>I-62 | 50 |

3) Pharmacokinetic Parameters in Mice

The pharmacokinetic behaviour of compounds is a prerequisite for reasonable use thereof in in vivo experimentation. The compounds were given in DMSO solution via intravenous route (IV) or oral route (PO) to balb/c mice. Blood samples were taken at times ranging from 5 minutes to 6 hours, the plasmas were collected and the concentration of the compounds in each sample was assayed by LC/MS/MS. The data obtained allowed the plotting of time-concentration curves and determination of fundamental parameters such as plasma half-life of the compound (T½), area under curve at a given time (AUCt) and the maximum concentration obtained (Cmax). Table 6 shows the gain contributed by piperazine substitution on the pharmacokinetic parameters of the compounds administered via intravenous route at a dose of 10 mg/kg.

FIG. 1 gives the time-plasma concentration curves in a mouse after administration of I-43 dia2 via IV and PO route. Compound I-43 dia2 therefore shows good bioavailability in a mouse, in particular via oral route.

TABLE 6

Pharmacokinetic parameters obtained with various piperazine substitutions.

| Example | Cmax (ng/mL) | AUCt (ng/mL*h) | AUCinf (ng/mL*h) | t½ (h) |
|---|---|---|---|---|
| 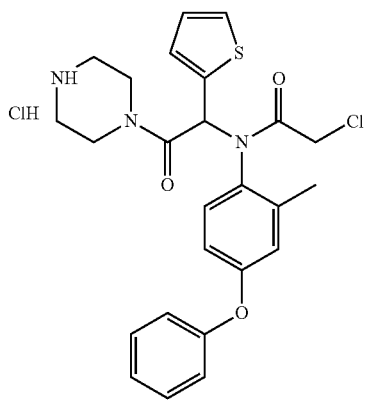<br>Comparative example | 1469.50 | 1278.25 | 1321.68 | 1.38 |

TABLE 6-continued

Pharmacokinetic parameters obtained with various piperazine substitutions.

| Example | Cmax (ng/mL) | AUCt (ng/mL*h) | AUCinf (ng/mL*h) | t½ (h) |
|---|---|---|---|---|
| 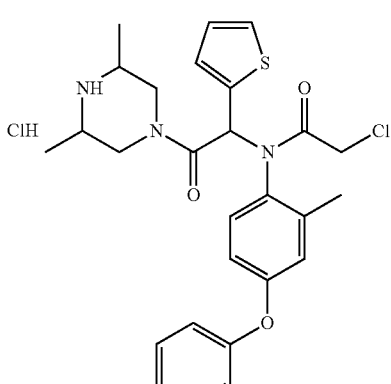 I-63 | 3797.6 | 3287.08 | 3837.61 | 2.64 |
| 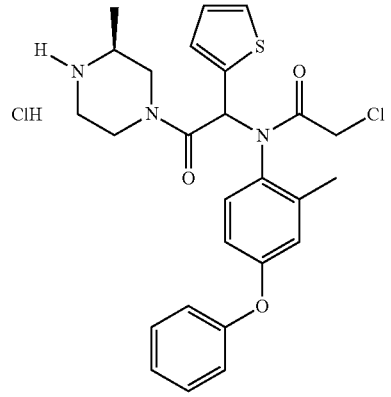 I-43 dia 2 | 1424.37 | 1677.94 | 2057.38 | 2.47 |

What is claimed is:

1. A method for the treatment of cancer comprising the administration to a person in need thereof of an efficient amount of a compound of following general formula (I):

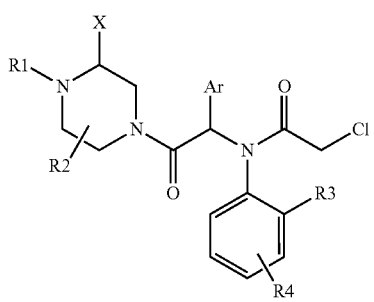

or a pharmaceutically acceptable salt thereof, a stereoisomer or a mixture of stereoisomers in any proportion,
where:
X is a $(C_1-C_6)$alkyl, phenyl, benzyl, C(O)OR5 or C(O)NHR5 group;

R1 is a hydrogen atom or a C(O)H, C(O)R6 or C(O)OR6 group;

R2 is a hydrogen atom or a $(C_1-C_6)$alkyl group;

or R2 together with R1 or X forms a saturated hydrocarbon chain to form a 5- or 6-membered ring;

R3 is a hydrogen or halogen atom or a $(C_1-C_6)$alkyl or $(C_1-C_6)$alkoxy group;

R4 is a hydrogen or halogen atom, CN, $NO_2$, or a $(C_1-C_6)$alkyl, $(C_1-C_6)$alkoxy, aryloxy, benzyloxy or heteroaryloxy group, the said group optionally being substituted by one or more halogen atoms;

Ar is a thiophenyl group or a phenyl group optionally substituted by one or more halogen atoms; and R5 and R6 independently of one another are a $(C_1-C_6)$ alkyl, aryl-$(C_1-C_6)$alkyl or aryl group, the said group optionally being substituted by one or more halogen atoms, wherein the cancer is selected from the group consisting of melanoma, lung cancer, CNS cancer, prostate cancer, renal cancer, head and neck cancer, and hepatocarcinoma.

2. The method according to claim 1, wherein the compound has the following formula (I-bis):

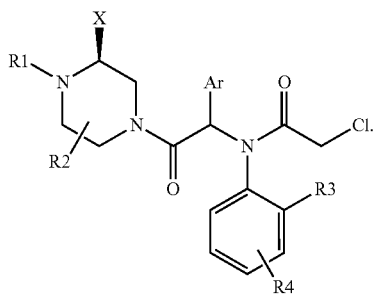
(I-bis)

3. The method according to claim 1, wherein Ar is a thiophenyl group or a phenyl group substituted by one or more fluorine atoms.

4. The method according to claim 3, wherein Ar is a thiophenyl group or a 4-fluoro-phenyl group.

5. The method according to claim 1, wherein R4 is a hydrogen or halogen atom or a ($C_1$-$C_6$)alkyl, ($C_1$-$C_6$)alkoxy or aryloxy group, the said group optionally being substituted by one or more halogen atoms.

6. The method according to claim 1, wherein R3 is a hydrogen atom or a ($C_1$-$C_6$)alkyl group.

7. The method according to claim 1, wherein X is a ($C_1$-$C_6$)alkyl, phenyl or benzyl group; R1 and R2 are a hydrogen atom; R3 is a hydrogen atom or a ($C_1$-$C_6$)alkyl group; R4 is a halogen atom or a ($C_1$-$C_6$)alkyl, ($C_1$-$C_6$) alkoxy, aryloxy or benzyloxy group, the said group optionally being substituted by one or more halogen atoms; Ar is a thiophenyl group or a phenyl group optionally substituted by a fluorine atom; and R5 and R6 independently of one another are a ($C_1$-$C_6$)alkyl, aryl-($C_1$-$C_6$)alkyl or aryl group, the said group optionally being substituted by one or more fluorine atoms.

8. The method according to claim 1, wherein the compound is selected from among:

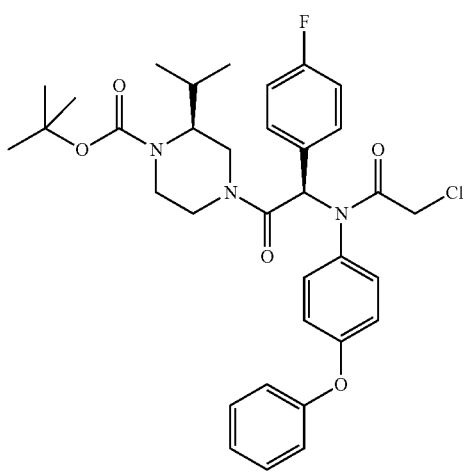
I-1a

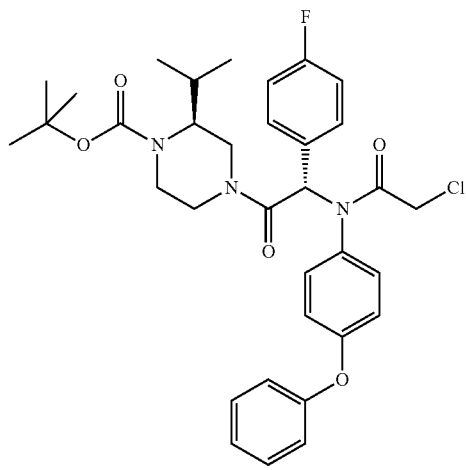
I-1b

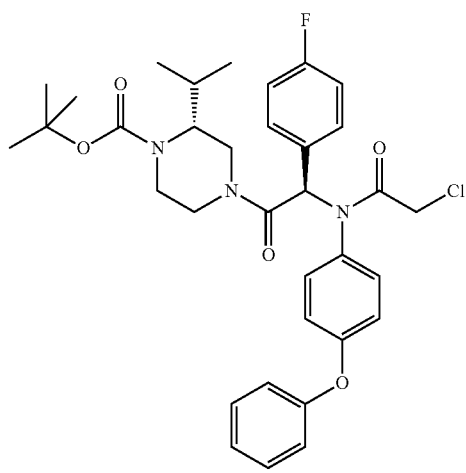
I-2a

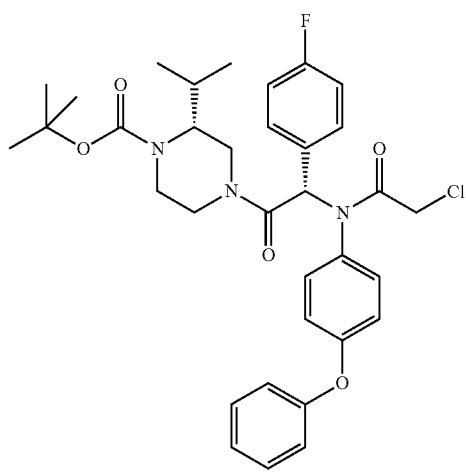
I-2b

-continued
I-3a
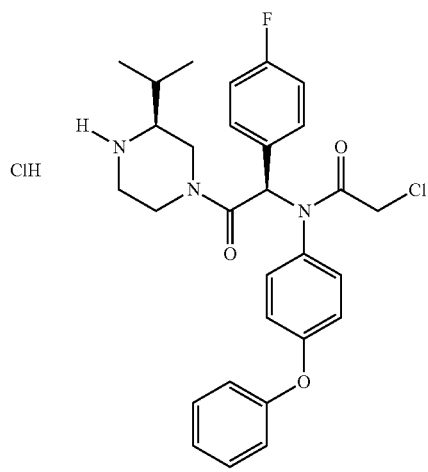
I-4b
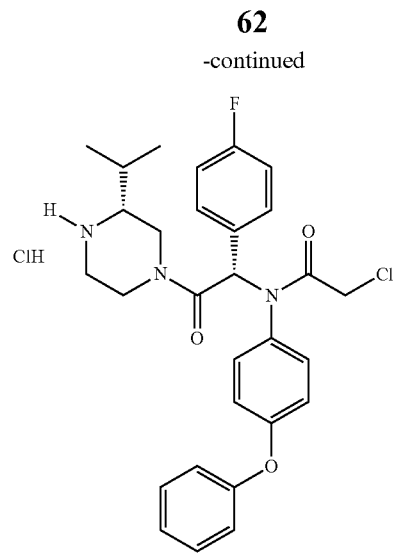
I-3b
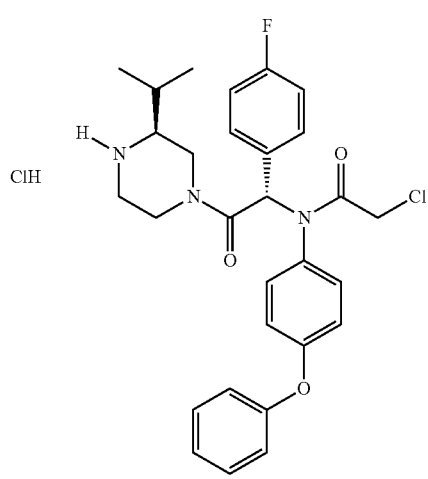
I-5a
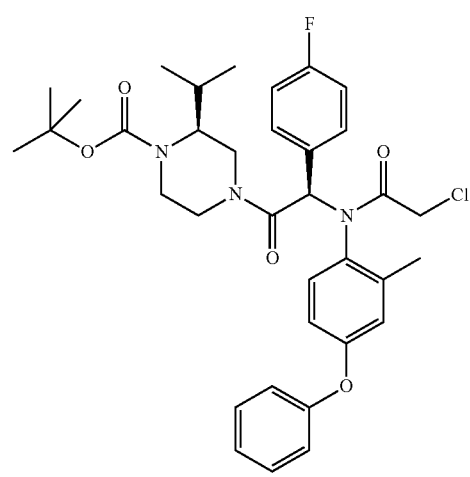
I-4a
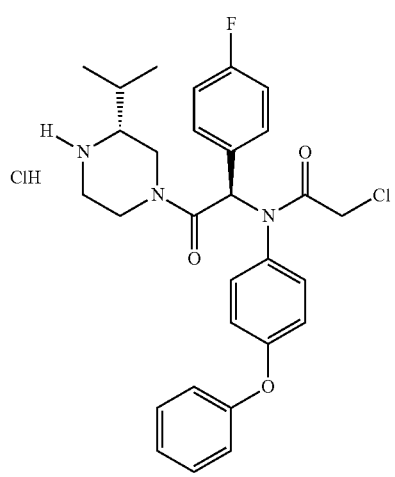
I-5b
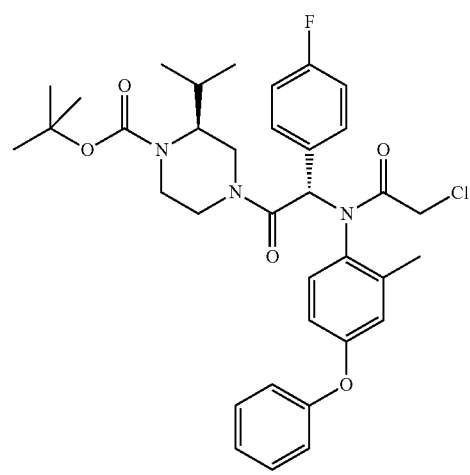

I-6a
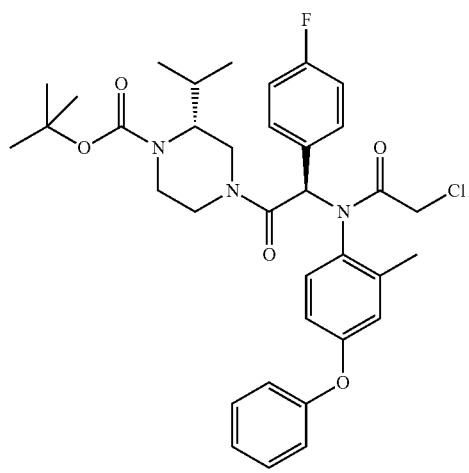
I-7b
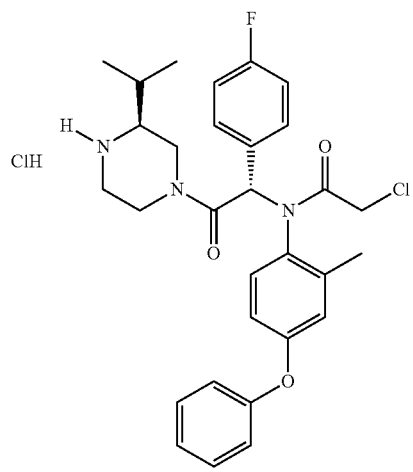
I-6b
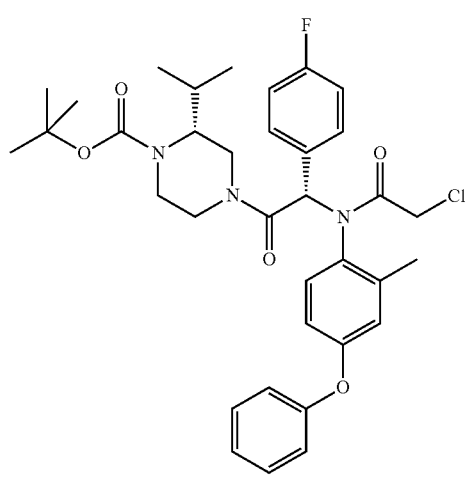
I-8a
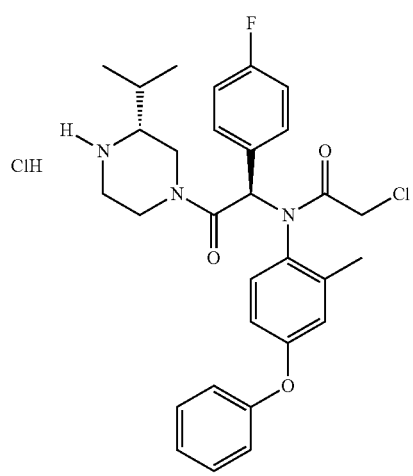
I-7a
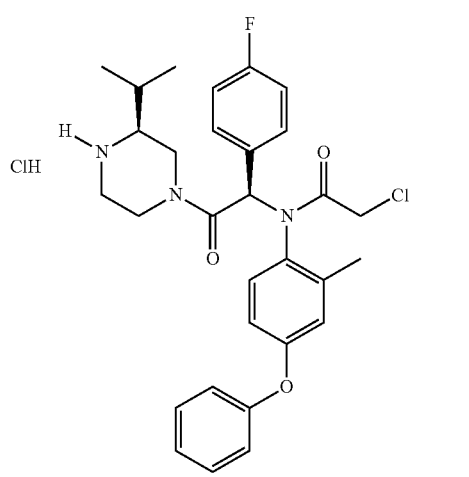
I-8b
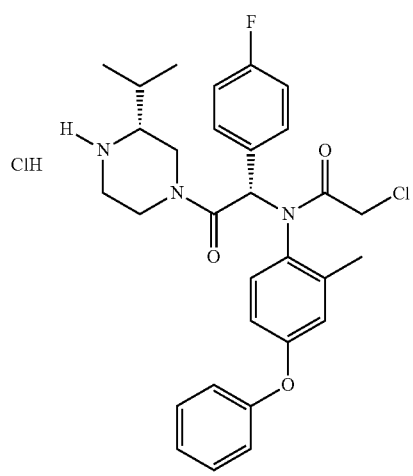

I-9
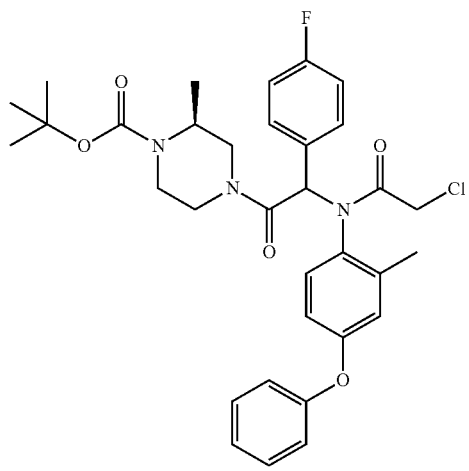
I-10
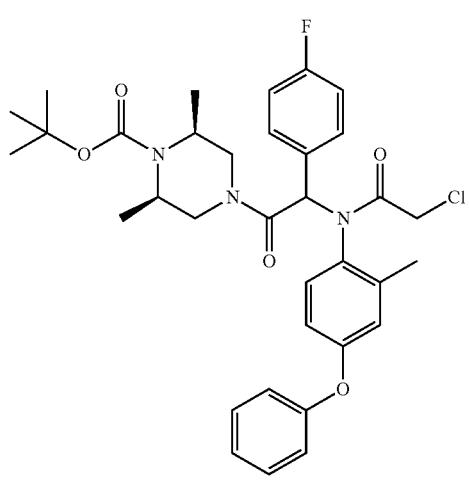
I-11
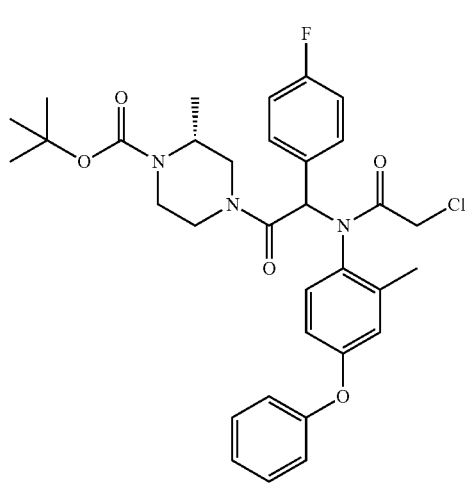
I-12
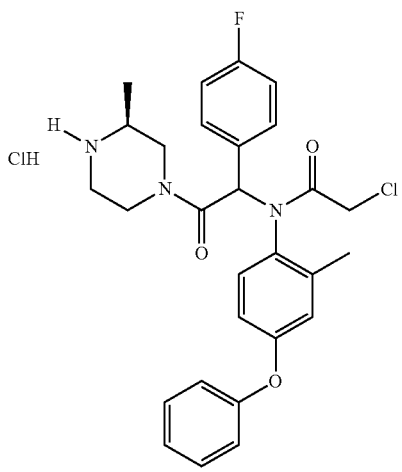
I-13
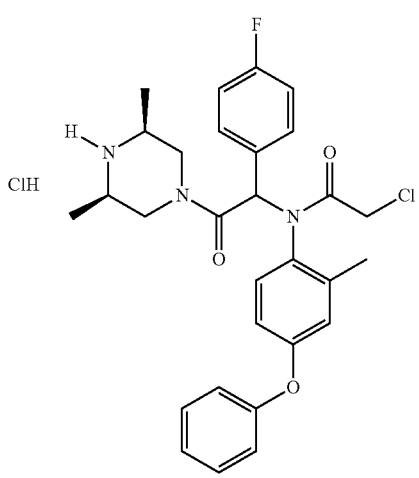
I-14
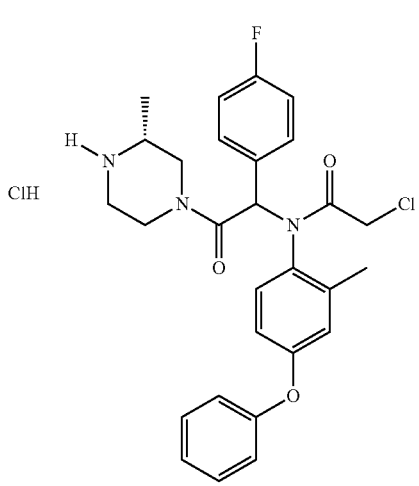

I-15a
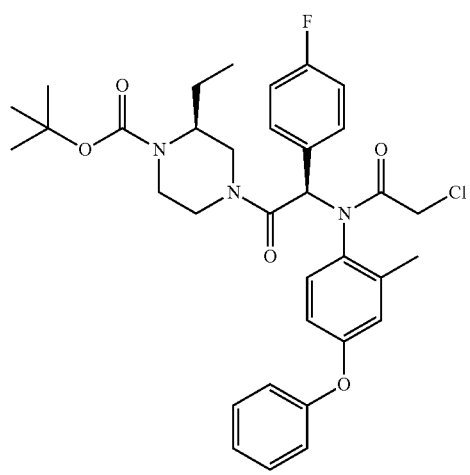
I-16b
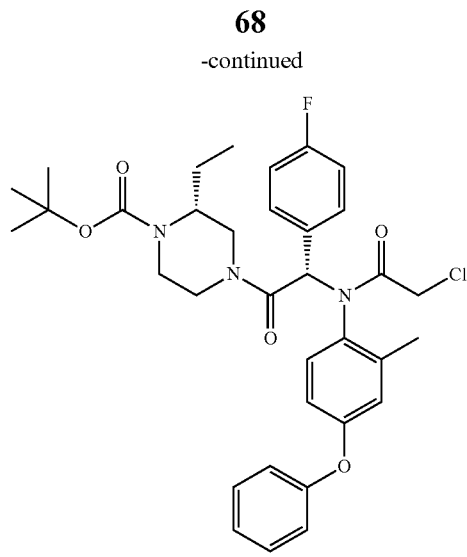
I-15b
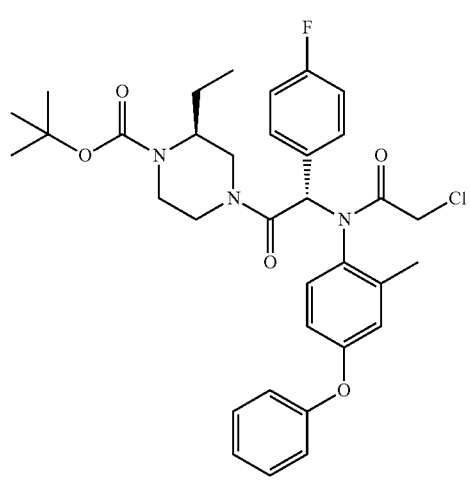
I-17a
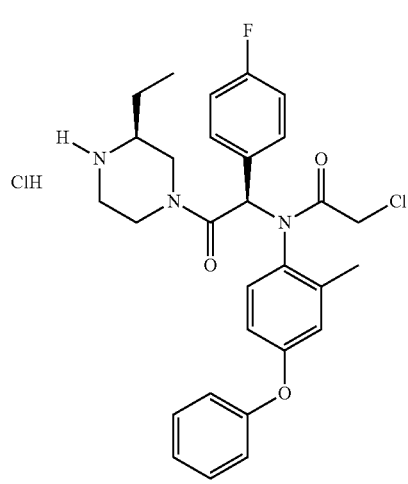
I-16a
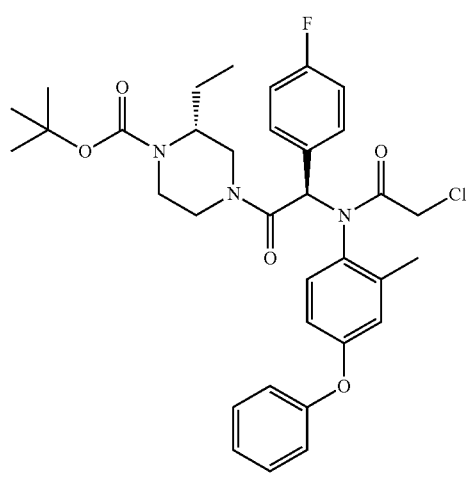
I-17b
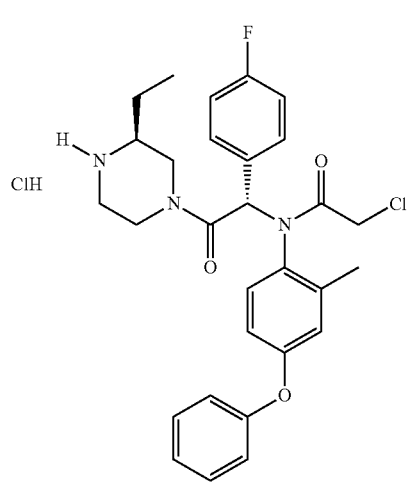

I-18a
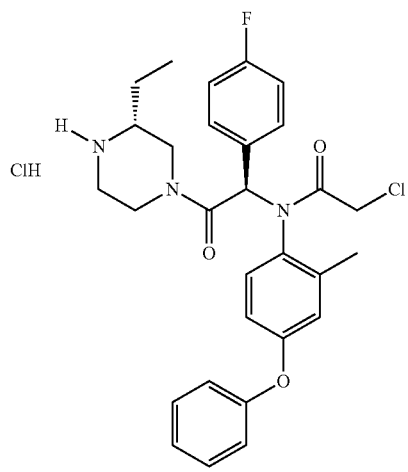
I-18b
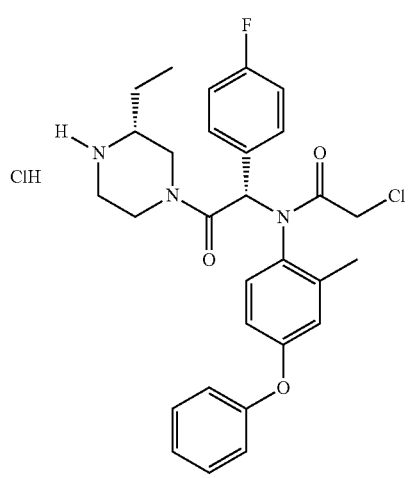
I-19a
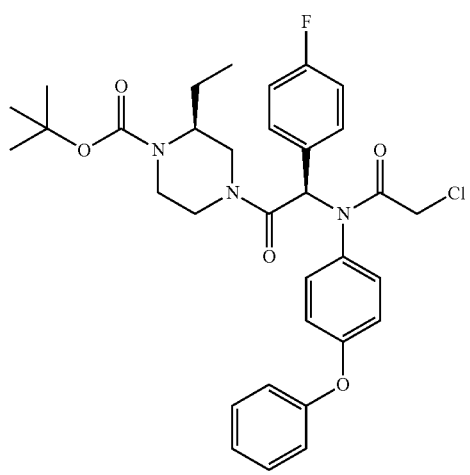
I-19b
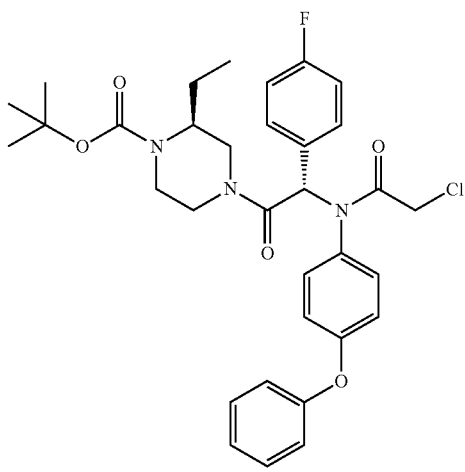
I-20a
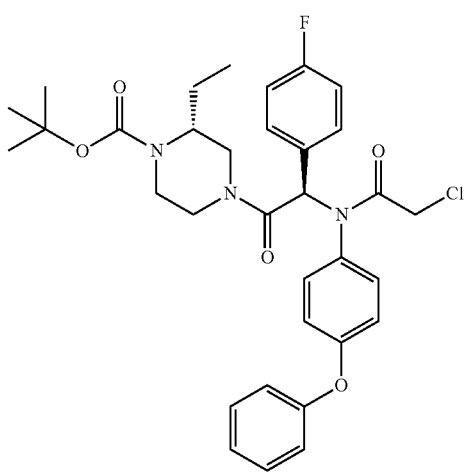
I-20b
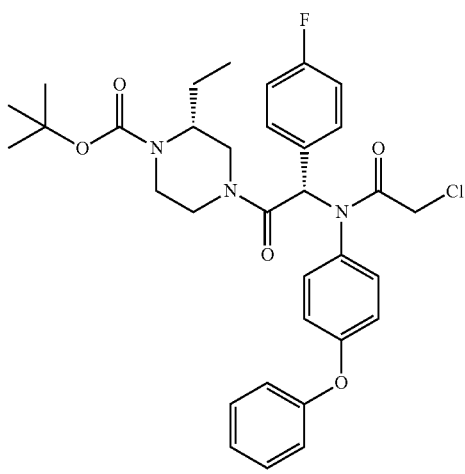

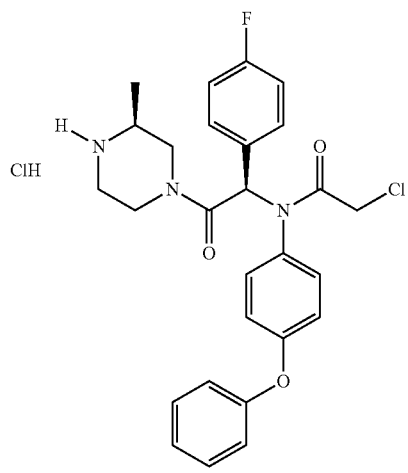
I-21a
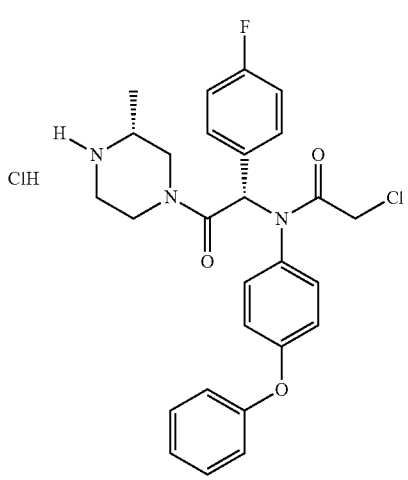
I-22b
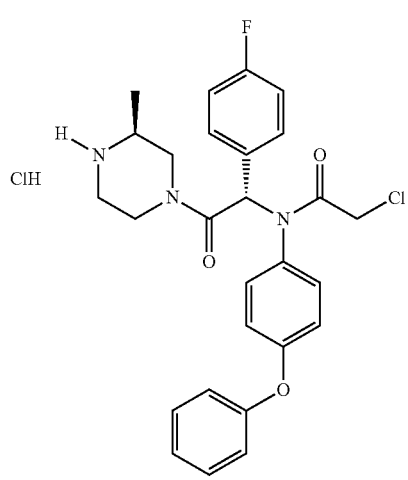
I-21b
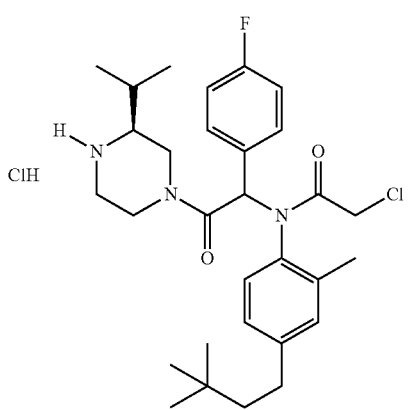
I-23
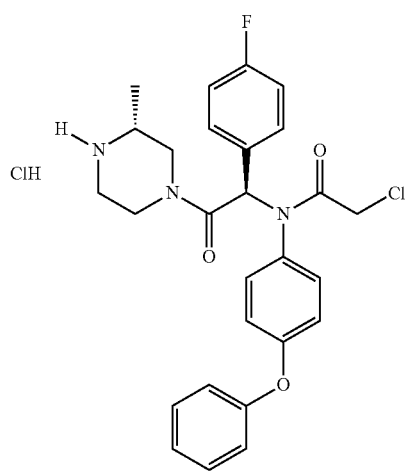
I-22a
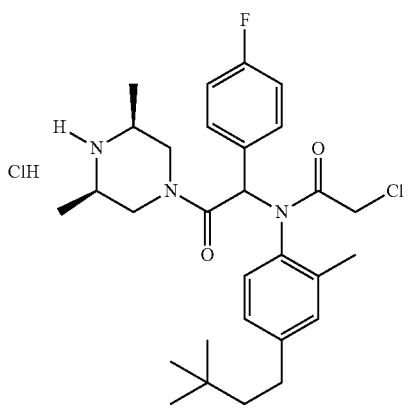
I-24

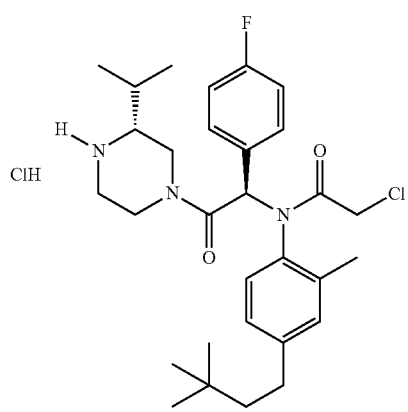
I-25a
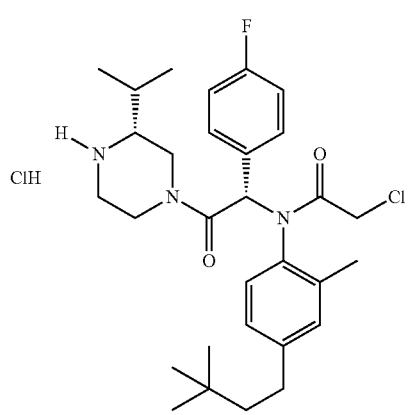
I-25b
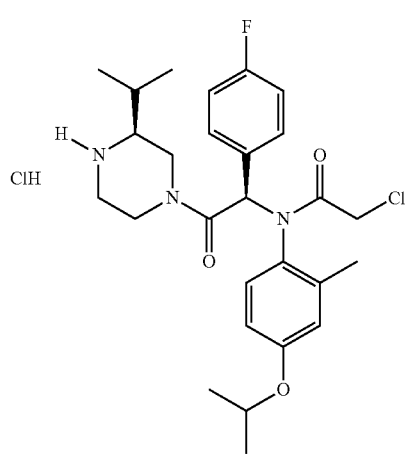
I-26a
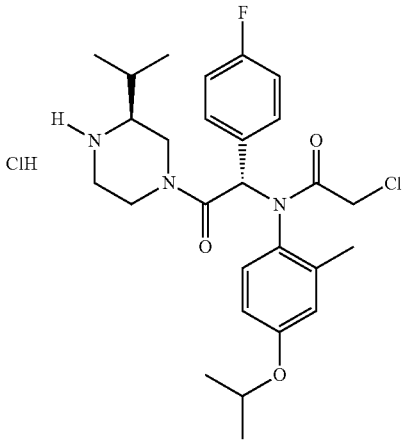
I-26b
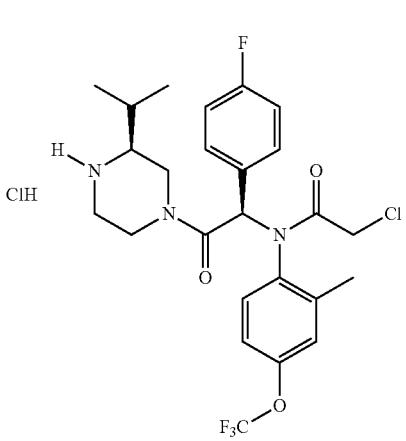
I-27a
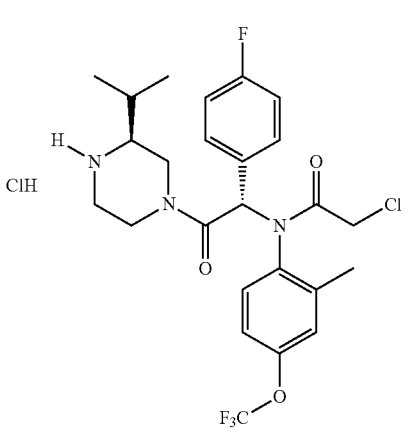
I-27b
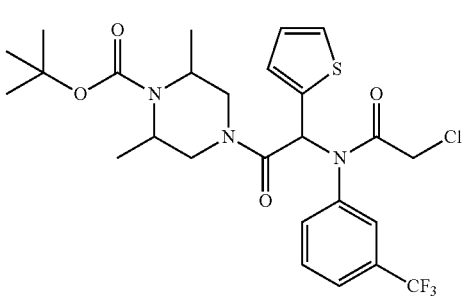
I-28

I-29
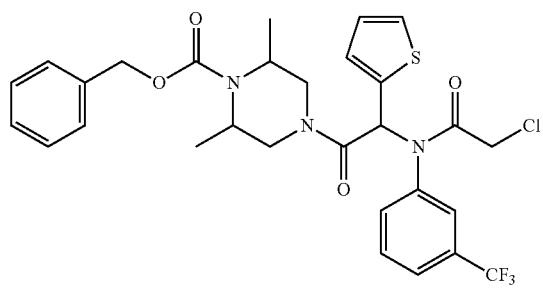
I-30
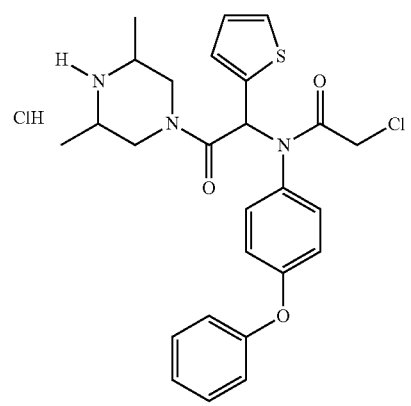
I-31
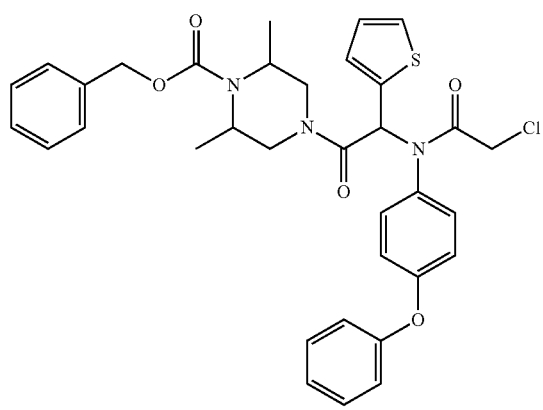
I-32
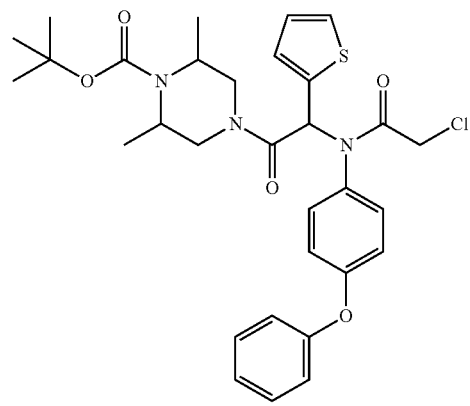
I-33
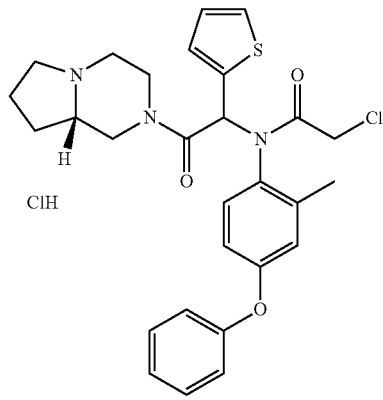
I-34
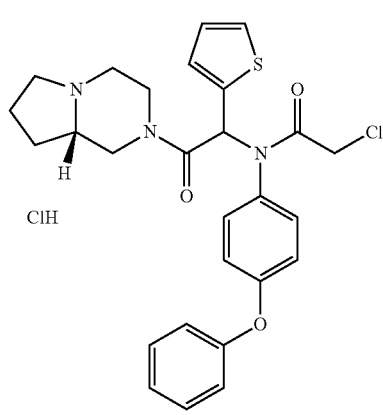
I-35
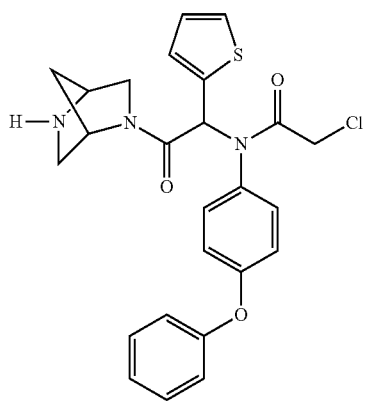
I-36
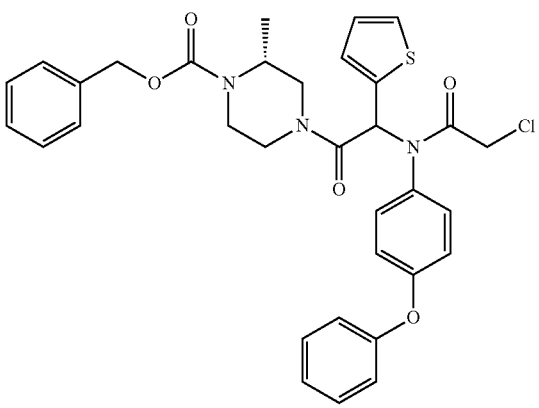

I-37
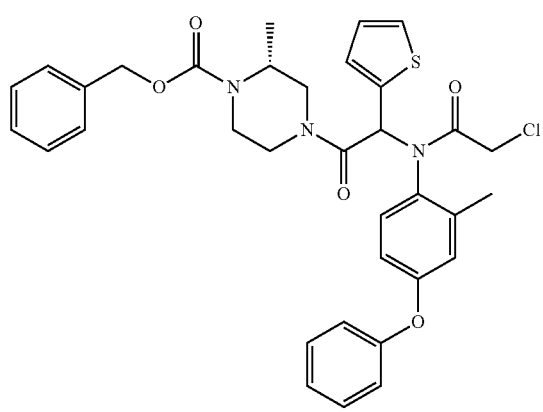
I-38
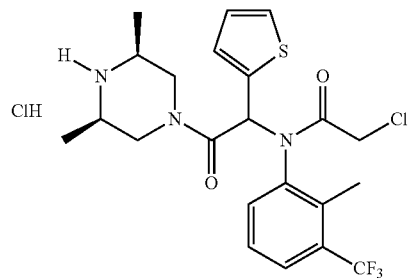
I-39
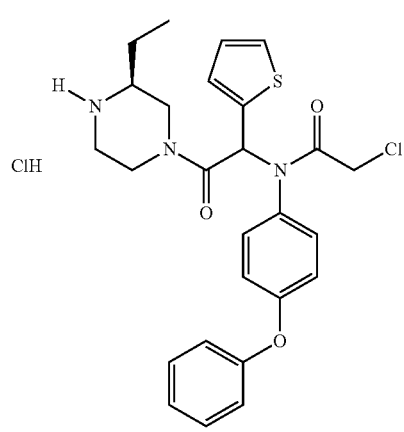
I-40a
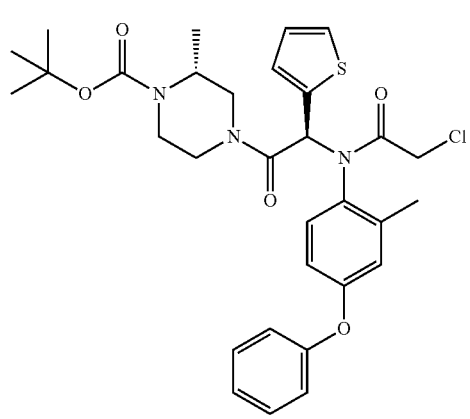
I-40b
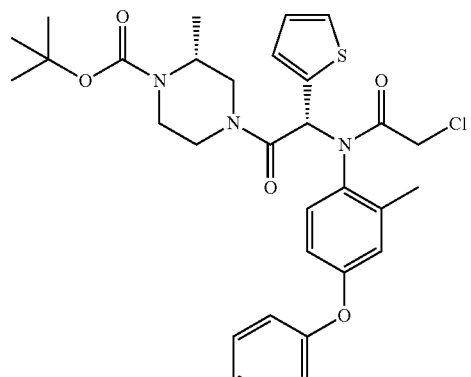
I-41a
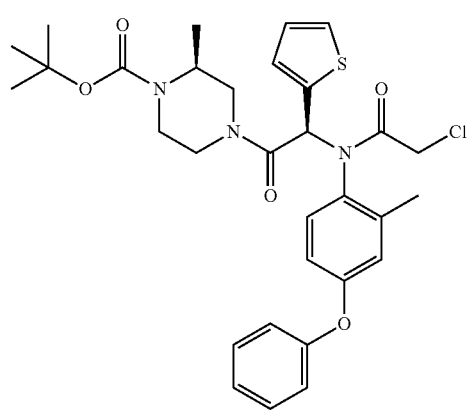
I-41b
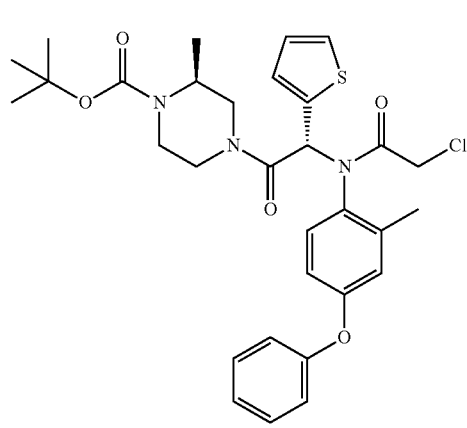
I-42a
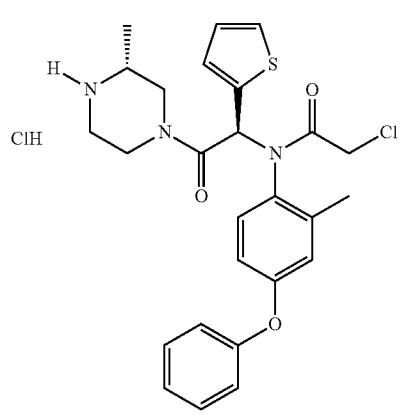

I-42b
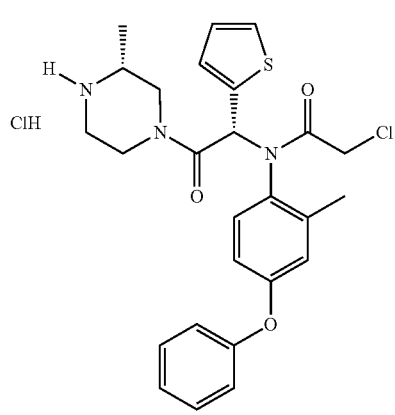
I-43a
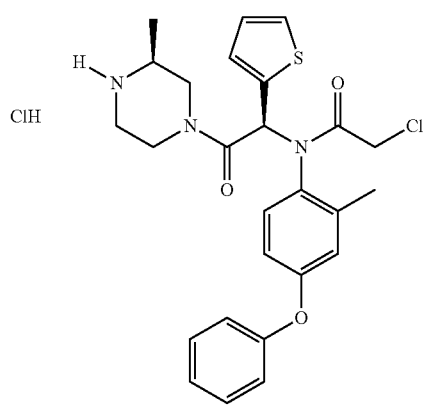
I-43b
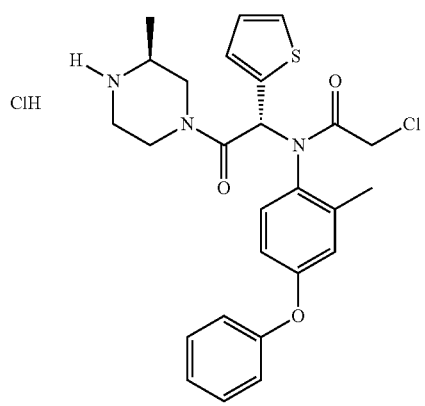
I-44
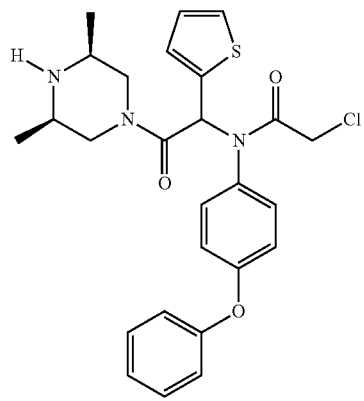
I-45
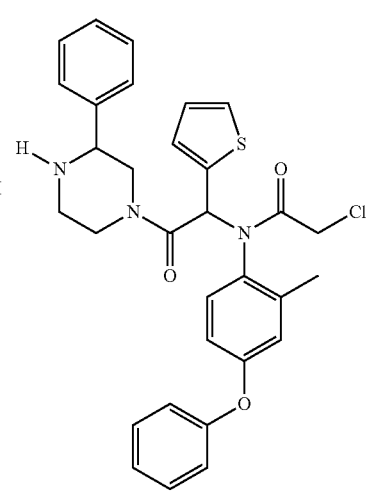
I-46a
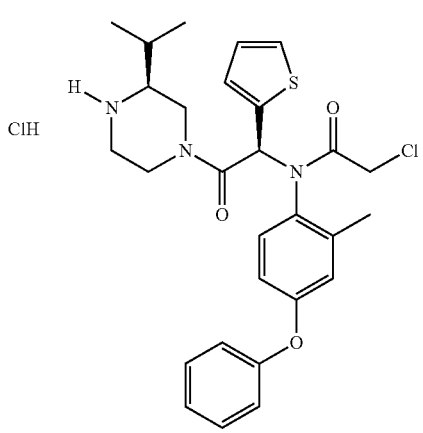
I-46b
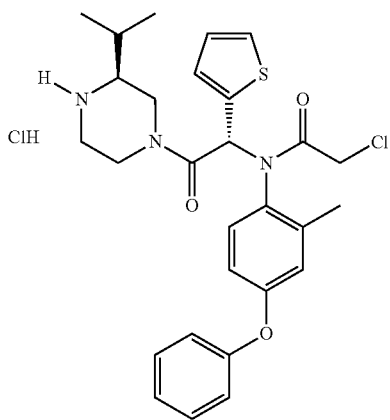

-continued
I-47a
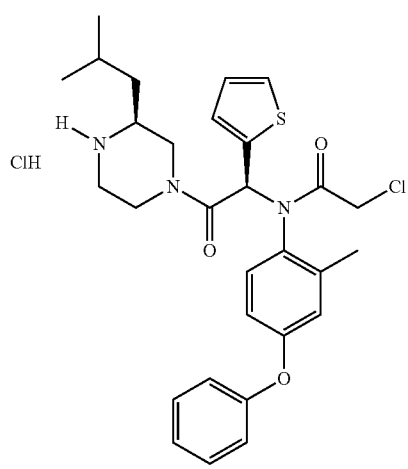
I-47b
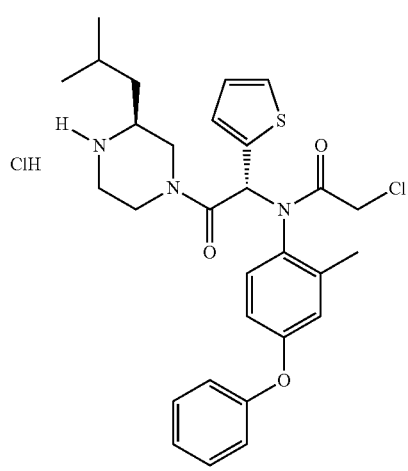
I-48
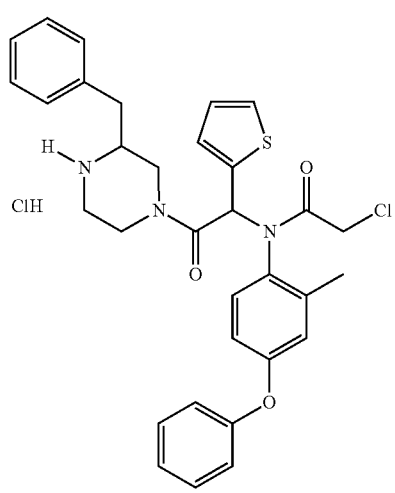
-continued
I-49
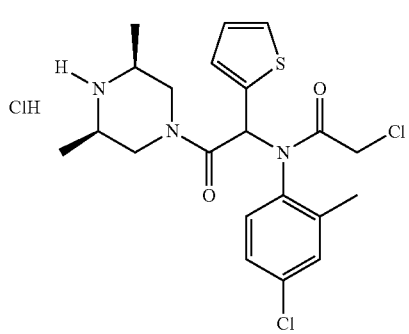
I-50a
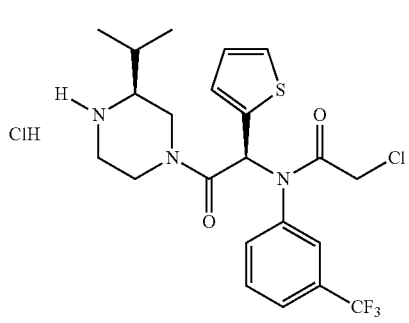
I-50b
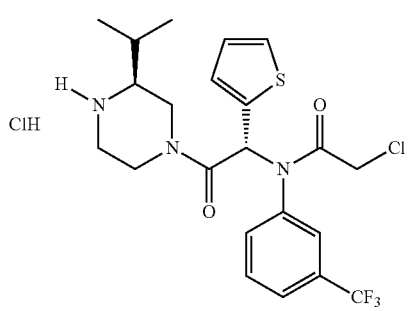
I-51a
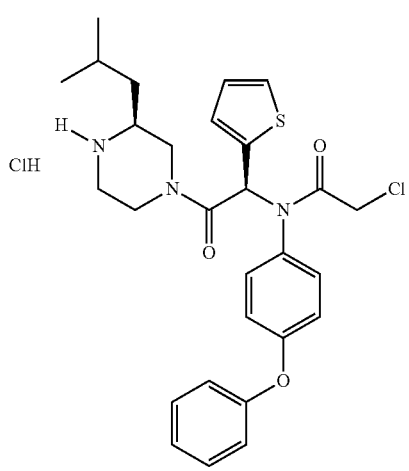

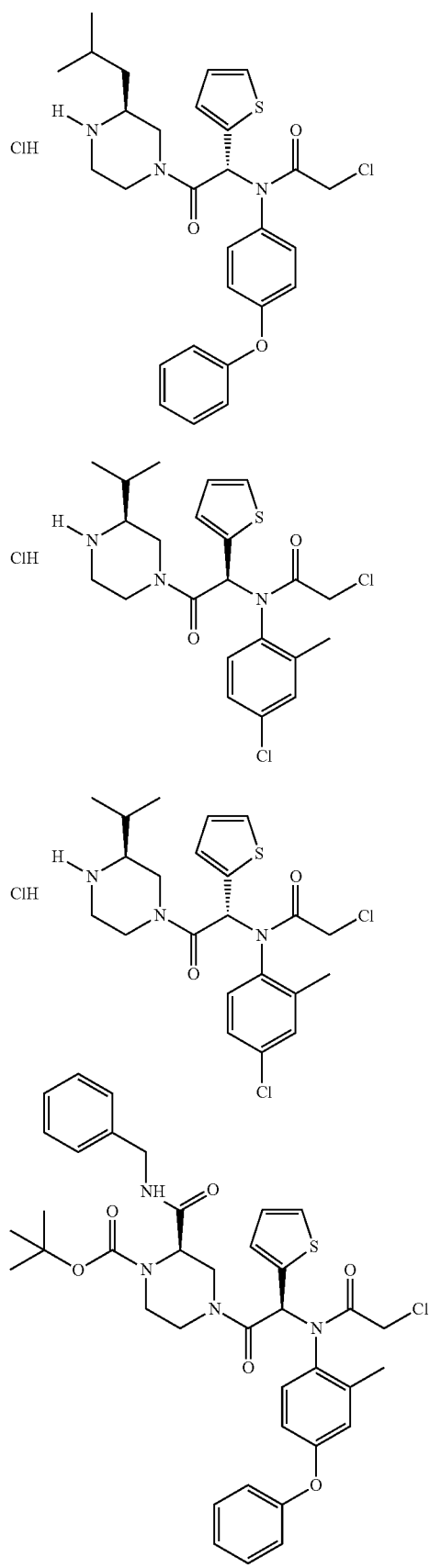
I-51b
I-52a
I-52b
I-53a
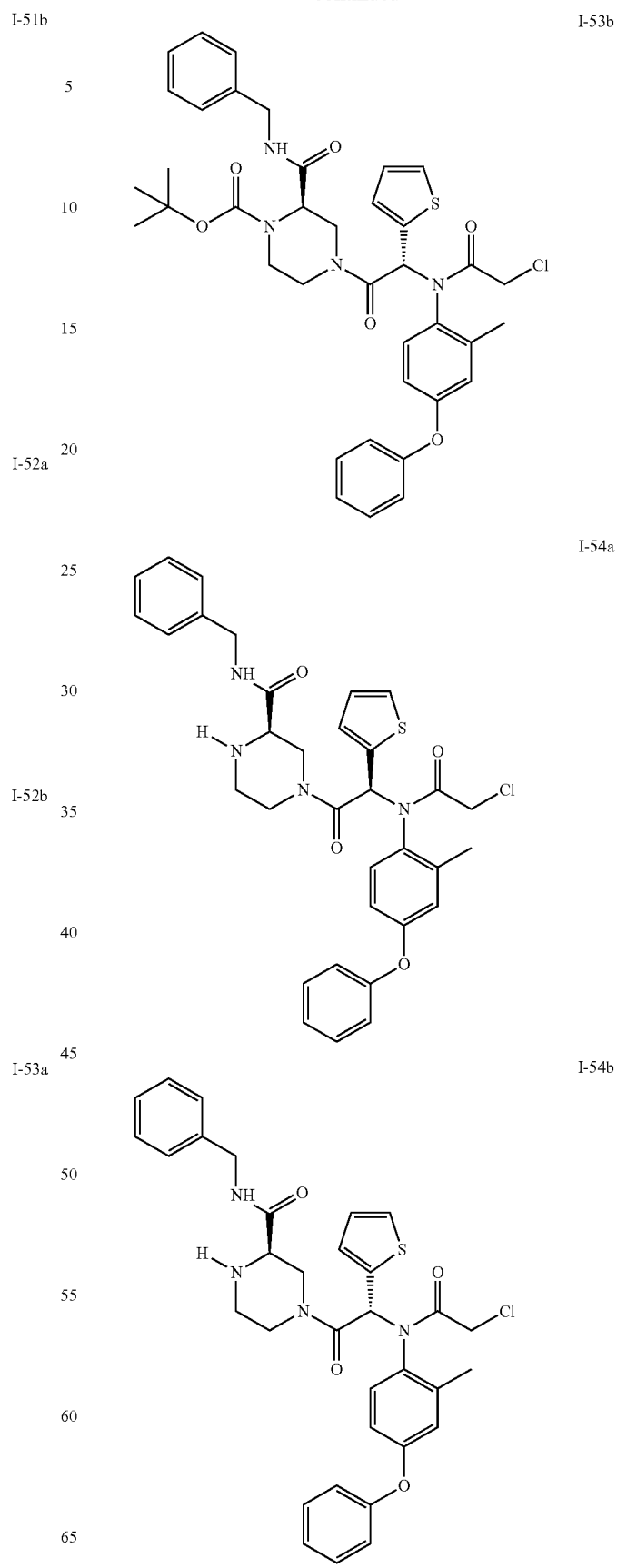
I-53b
I-54a
I-54b

I-55a
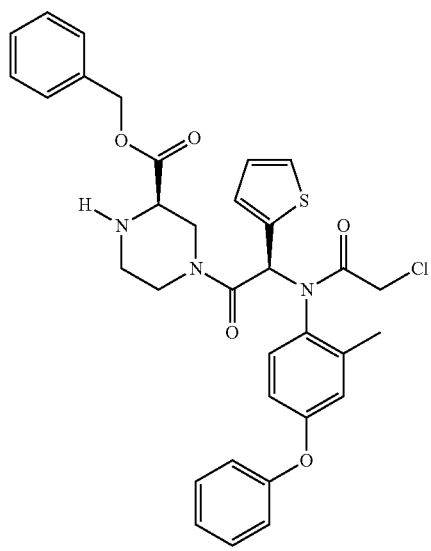
I-55b
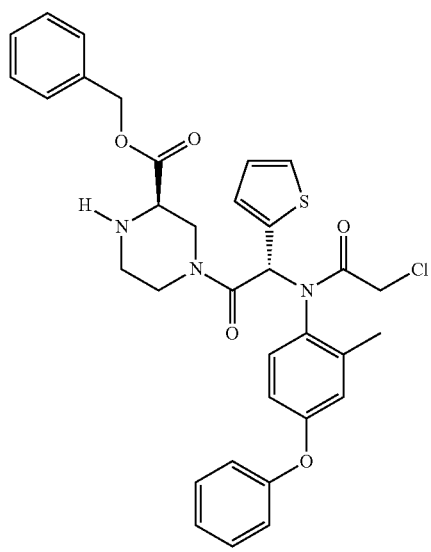
I-56a
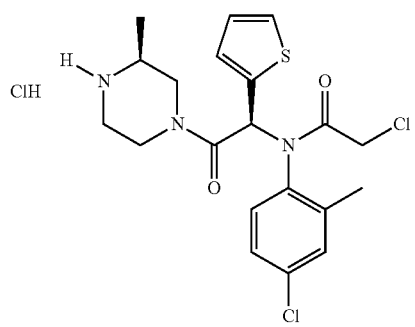
I-56b
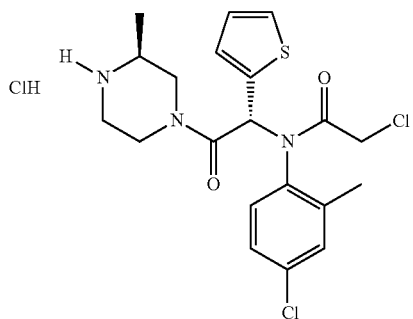
I-57
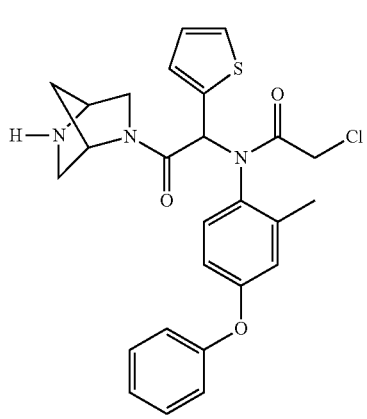
I-58
I-59
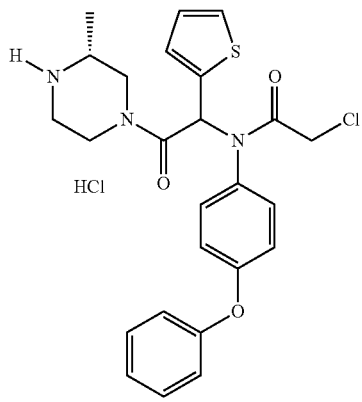

-continued

I-60

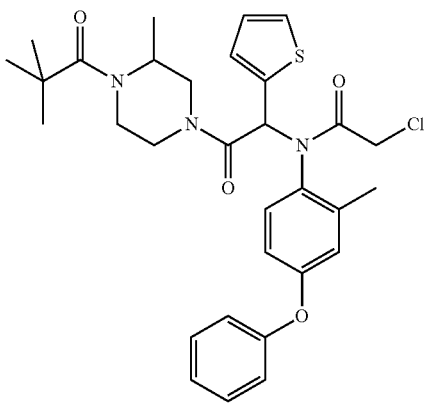

I-61

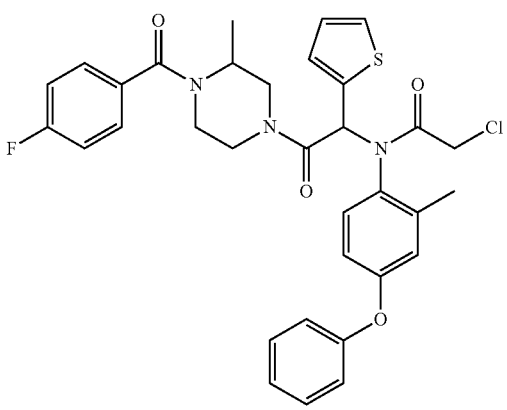

I-62

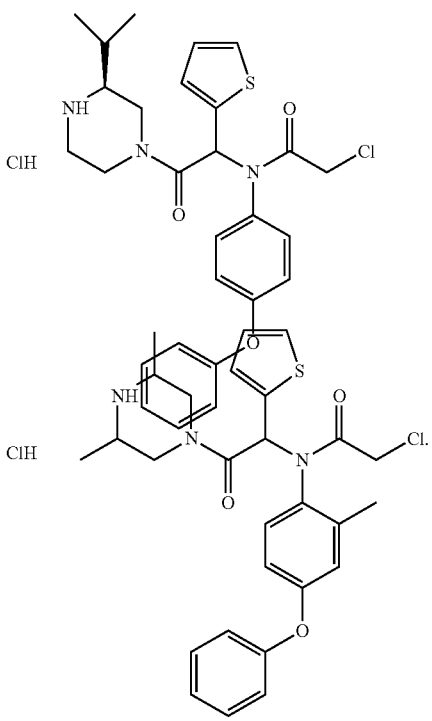

I-63

9. The method according to claim 1, wherein the cancer is a chemotherapy-resistant cancer.

10. A method for the treatment of cancer comprising the administration to a person in need thereof of an efficient amount of a pharmaceutical composition comprising at least one compound of general formula (I) according to claim 1 in association with one or more pharmaceutically acceptable excipients,
wherein the cancer is selected from the group consisting of melanoma, lung cancer, CNS cancer, prostate cancer, renal cancer, head and neck cancer and hepatocarcinoma.

11. The method according to claim 10, wherein the pharmaceutical composition comprises at least one other active ingredient.

12. The method according to claim 11, wherein the at least one other active ingredient is an anticancer agent.

13. The method according to claim 12, wherein the at least one other active ingredient is chosen from among cisplatin and its derivatives; taxanes, paclitaxel and docetaxel; vinca alkaloids; purine analogues s; topoisomerase I inhibitors; topoisomerase II inhibitors; anti-tumour nucleoside derivatives; alkylating agents; derivatives of anti-tumour anthracyclines; molecules targeting the IGF-I receptor; tetracarcin derivatives; corticosteroids; antibodies; antagonists or selective modulators of oestrogen receptors; aromatase inhibitors; differentiating agents; DNA methyl-transferase inhibitors; antifolates; antibiotics; antimetabolites; apoptosis-inducing agents and anti-angiogenic agents of Bcl-2 inhibitors; agents binding to tubulin; kinase inhibitors; farnesyl transferase inhibitors; histone-deacetylase inhibitors; inhibitors of the ubiquitin-proteasome system; and telomerase inhibitors.

14. The method according to claim 13, wherein the cisplatin derivatives are chosen among carboplatin and oxalyplatin; the taxanes are chosen among taxol, taxotere, paclitaxel and docetaxel; the vinca alkaloids are chosen among vinblastine, vincristine and vinorelbine; the purine analogues are chosen among mercaptopurine, thioguanine, pentostatin and 2-chlorodeoxyadenosine; the topoisomerase I inhibitors are chosen among camptothecin compounds; the topoisomerase II inhibitors are chosen among epipodophyllotoxin, podophyllotoxin and the derivatives thereof; the anti-tumour nucleoside derivatives are chosen among 5-fluorouracil, leucovorin, gemcitabine and capecitabine; the alkylating agents are chosen among nitrogen mustards, nitroso-ureas, alkylsulfonates, ethylenimines, methylmelamines and tetrazines; the derivatives of anti-tumour anthracyclines are chosen among daunorubicin, adriamycin, doxil, idarubicin and mitoxantrone; the molecule targeting the IGF-I receptor is picropodophyllin; the tetracarcin derivative is tetrocarcin A; the corticosteroid is prednisone; the antibodies are chosen among trastuzumab (anti-HER2 antibody), rituximab (anti-CD20 antibody), gemtuzamab, cetuximab, pertuzumab and bevacizumab; the antagonists or selective modulators of oestrogen receptors are chosen among tamoxifen, fulvestrant, toremifene, droloxifene, faslodex and raloxifene; the aromatase inhibitors are chosen among exemestane, anastrozole, letrozole and vorozole; the differentiating agents are chosen among retinoids and agents blocking the metabolism of retinoic acid; the DNA methyltransferase inhibitors are chosen among azacytidine and decitabine; the antifolate is permetrexed disodium; the antibiotics are chosen among antinomycin D, bleomycin, mitomycin C, actinomycin D, carminomycin, daunomycin and plicamycin; the antimetabolites are chosen among chlofarabine, aminopterin, cytosine arabinoside, floxuridine and methotrexate; the apoptosis-inducing agents and anti-angiogenic agents of Bcl-2 inhibitors are chosen among 2-methoxycarbonylamino-4-methylsulfanyl-butyric acid, 4-(4,9-dioxo-4,9-dihydronaphtho[2,3-d]thiazol-2-ylamino)- phenyl-ester, 4-[4-[(4'-Chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl] benzamide, gossypol, 2-amino-6-bromo-α-cyano-3-(ethoxycarbonyl)-4H-1-benzopyran-4-acetic acid, ethyl ester, N-[4-[[2-(1,1-Dimethylethyl)phenyl]sulfonyl]phenyl]-2,3,4-trihydroxy-5-[[2-(1-methylethyl)phenyl]methyl] benzamide and decanoic acid; the agents binding to tubulin are chosen among combrestatin, colchicine derivatives and nocodazole; the kinase inhibitors are chosen among flavoperidol, imatinib mesylate, erlotinib and gefitinib; the farnesyl transferase inhibitor is tipifarnib; the histone-deacetylase inhibitors are chosen among sodium butyrate, suberoylanilide hydroxamic acid, depsipeptide, dacinostat, N-hydroxy-2-(4-(naphthalen-2-ylsulfonyl)piperazin-1-yl)pyrimidine-5-carboxamide, quisinostat and trichostatin A; the inhibitors of the ubiquitin-proteasome system are chosen among bortezomib, bortezomib and yondelis; and the telomerase inhibitor is telomestatin.

15. The method according to claim 14, wherein the camptothecin compounds are chosen among irinotecan and topotecan; the podophyllotoxin derivatives are chosen among etoposide and teniposide; the nitrogen mustards are chosen among cyclophosphamide, mechlorethamine, chlorambucil and melphalan; the nitroso-ureas are chosen among carmustin, lomustin and streptozocin; the alkylsulfonate is busulfan; the ethylenimines and methylmelamines are chosen among thiotepa and hexamethylmelamine; the tetrazine is dacarbazine; the retinoids are chosen among retinoic acid and vitamin D; and the agent blocking the metabolism of retinoic acid is Isoretinoin.

16. A method for the treatment of cancer comprising the administration to a person in need thereof of an efficient amount of a pharmaceutical composition comprising:
  (i) at least one formula (I) compound according to claim 1; and
  (ii) at least one other active ingredient,
  as combination products for simultaneous, separate or time-staggered use thereof,
  wherein the cancer selected from the group consisting of melanoma, lung cancer, CNS cancer, prostate cancer, renal cancer, head and neck cancer and hepatocarcinoma.

17. The method according to claim 16, wherein the at least one other active ingredient is an anticancer agent.

18. The method according to claim 17, wherein the at least one other active ingredient is selected from among cisplatin and the derivatives thereof; taxanes; vinca alkaloids; purine analogues; topoisomerase I inhibitors; topoisomerase II inhibitors; anti-tumour nucleoside derivatives; alkylating agents; derivatives of anti-tumour anthracyclines; molecules targeting the IGF-I receptor; tetracarcin derivatives; corticosteroids; antibodies; antagonists or selective modulators of oestrogen receptors; aromatase inhibitors; differentiating agents; DNA methyl-transferase inhibitors; antifolates; antibiotics; antimetabolites; apoptosis-inducing agents and anti-angiogenic agents of Bcl-2 inhibitors; agents binding to tubulin; kinase inhibitors; farnesyl transferase inhibitors; histone-deacetylase inhibitors; inhibitors of the ubiquitin-proteasome system s; and telomerase inhibitors.

19. The method according to claim 18, wherein the cisplatin derivatives are chosen among carboplatin and oxalyplatin; the taxanes are chosen among taxol, taxotere, paclitaxel and docetaxel; the vinca alkaloids are chosen among vinblastine, vincristine and vinorelbine; the purine analogues are chosen among mercaptopurine, thioguanine, pentostatin and 2-chlorodeoxyadenosine; the topoisomerase I inhibitors are chosen among camptothecin compounds; the topoisomerase II inhibitors are chosen among epipodophyllotoxin, podophyllotoxin and the derivatives thereof; the anti-tumour nucleoside derivatives are chosen among 5-fluorouracil, leucovorin, gemcitabine and capecitabine; the alkylating agents are chosen among nitrogen mustards, nitroso-ureas, alkylsulfonates, ethylenimines, methylmelamines and tetrazines; the derivatives of anti-tumour anthracyclines are chosen among daunorubicin, adriamycin, doxil, idarubicin and mitoxantrone; the molecule targeting the IGF-I receptor is picropodophyllin; the tetracarcin derivative is tetrocarcin A; the corticosteroid is prednisone; the antibodies are chosen among trastuzumab (anti-HER2 antibody), rituximab (anti-CD20 antibody), gemtuzamab, cetuximab, pertuzumab and bevacizumab; the antagonists or selective modulators of oestrogen receptors are chosen among tamoxifen, fulvestrant, toremifene, droloxifene, faslodex and raloxifene; the aromatase inhibitors are chosen among exemestane, anastrozole, letrozole and vorozole; the differentiating agents are chosen among retinoids and agents blocking the metabolism of retinoic acid; the DNA methyl-transferase inhibitors are chosen among azacytidine and decitabine; the antifolate is permetrexed disodium; the antibiotics are chosen among antinomycin D, bleomycin, mitomycin C, actinomycin D, carminomycin, daunomycin and plicamycin; the antimetabolites are chosen among chlofarabine, aminopterin, cytosine arabinoside, floxuridine and methotrexate; the apoptosis-inducing agents and anti-angiogenic agents of Bcl-2 inhibitors are chosen among 2-methoxycarbonylamino-4-methylsulfanyl-butyric acid, 4-(4,9-dioxo-4,9-dihydronaphtho[2,3-d]thiazol-2-ylamino)-phenyl-ester, 4-[4-[(4 '-Chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl] benzamide, gossypol, 2-amino-6-bromo-α-cyano-3-(ethoxycarbonyl)-4H-1-benzopyran-4-acetic acid, ethyl ester, N-[4-[[2-(1,1-Dimethylethyl)phenyl]sulfonyl]phenyl]-2,3,4-trihydroxy-5-[[2-(1-methylethyl)phenyl]methyl] benzamide and decanoic acid; the agents binding to tubulin are chosen among combrestatin, colchicine derivatives and nocodazole; the kinase inhibitors are chosen among flavoperidol, imatinib mesylate, erlotinib and gefitinib; the farnesyl transferase inhibitor is tipifarnib; the histone-deacetylase inhibitors are chosen among sodium butyrate, suberoylanilide hydroxamic acid, depsipeptide, dacinostat, N-hydroxy-2-(4-(naphthalen-2-ylsulfonyl)piperazin-1-yl)pyrimidine-5-carboxamide, quisinostat and trichostatin A; the inhibitors of the ubiquitin-proteasome system are chosen among bortezomib, bortezomib and yondelis; and the telomerase inhibitor is telomestatin.

20. The method according to claim 19, wherein the camptothecin compounds are chosen among irinotecan and topotecan; the podophyllotoxin derivatives are chosen among etoposide and teniposide; the nitrogen mustards are chosen among cyclophosphamide, mechlorethamine, chlorambucil and melphalan; the nitroso-ureas are chosen among carmustin, lomustin and streptozocin; the alkylsulfonate is busulfan; the ethylenimines and methylmelamines are chosen among thiotepa and hexamethylmelamine; the tetrazine is dacarbazine; the retinoids are chosen among retinoic acid and vitamin D; and the agent blocking the metabolism of retinoic acid is Isoretinoin.

* * * * *

UNITED STATES PATENT AND TRADEMARK OFFICE
CERTIFICATE OF CORRECTION

PATENT NO. : 9,877,962 B2  
APPLICATION NO. : 15/135994  
DATED : January 30, 2018  
INVENTOR(S) : Carniato et al.

Page 1 of 1

It is certified that error appears in the above-identified patent and that said Letters Patent is hereby corrected as shown below:

In the Specification

Column 12, Line 31:
Delete "10 M" and insert --10 μM--

Column 23, Line 46:
Delete "Example 16" and insert --Examples 1-6--

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*